United States Patent
Quinn et al.

(10) Patent No.: US 7,618,946 B2
(45) Date of Patent: Nov. 17, 2009

(54) ANALGESIC COMPOUNDS, EXTRACTS CONTAINING SAME AND METHODS OF PREPARATION

(75) Inventors: Ronald Quinn, Queensland (AU); Clive Mills, Dublin (IE)

(73) Assignees: Griffith University (AU); Jarlmadangah Buru Aboriginal Corporation (AU)

( * ) Notice: Subject to any disclaimer, the term of this patent is extended or adjusted under 35 U.S.C. 154(b) by 53 days.

(21) Appl. No.: 10/580,805

(22) PCT Filed: Nov. 26, 2004

(86) PCT No.: PCT/AU2004/001660

§ 371 (c)(1), (2), (4) Date: Mar. 16, 2007

(87) PCT Pub. No.: WO2005/051969

PCT Pub. Date: Jun. 9, 2005

(65) Prior Publication Data

US 2007/0270375 A1    Nov. 22, 2007

(30) Foreign Application Priority Data

Nov. 27, 2003    (AU) .............................. 2003906558

(51) Int. Cl.
*A61K 31/7012*    (2006.01)
*A61K 31/7016*    (2006.01)
*A61K 31/702*    (2006.01)
*A61K 31/704*    (2006.01)
*C07H 15/256*    (2006.01)

(52) U.S. Cl. .......................... 514/33; 536/4.4; 536/18.1
(58) Field of Classification Search ........................ None
See application file for complete search history.

(56) References Cited

U.S. PATENT DOCUMENTS 7,262,285 B2 *    8/2007    Chan et al. .................. 536/18.1

OTHER PUBLICATIONS

Pal et. al. (Abstract; Phytochemistry, 1994, 35(5), 1315-1318.*
The Merck Manual of Diagnosis and Therapy, Seventeenth Edition, Published by Merck Research Laboratories (1999) Beers and Berkow, eds., pp. 1373, 1374, and 1511.*
Woolf et al., "Neuropathic pain: aetiology, symptoms, mechanisms, and management" (1999) The Lancet, vol. 353, pp. 1959-1964.*
Crublet et al., Acylated triterpenoid saponing from the stem bark of Foetidia africana, Journal of Natural Products (2002), 65 (11), 1560-1567, American Chemical Society, (Abstract).
Wang et al., Triterpenoid saponins from Berneuxia thibetica, Phytochemistry (1998), 48(8), 1411-1414, Elsevier Science Ltd., (Abstract).
Burczyk et al., Saponins from Hacquetia epipactis, Phytochemistry (1995), 39(11), 195-8, Elsevier Science Ltd., (Abstract).
Pal et al., Saponins from Barringtonia acutanglua, Phytochemistry (1994), 35(5), 1315-18, (Abstract).
Kitagawa et al., Structure of desacyl-jegosaponin, a common desacyl derivative of jegosaponin isolated from pericarps of Styrax japonica, Chemical & Pharmaceutical Bulletin (1974), 22(7), 1675-7, (Abstract).

* cited by examiner

*Primary Examiner*—Shaojia Anna Jiang
*Assistant Examiner*—Eric S Olson
(74) *Attorney, Agent, or Firm*—Porzio, Bromberg & Newman

(57) ABSTRACT

Various compounds obtained from plants of the *Barringtonia* species which are derived from Barringtoside A and Barringtoside C as precursor compounds which especially have an arabinopyranosyl substituent at the 21 position which may optionally be further substituted with benzoyl, dibenzoyl, methyl butanoyl, methyl butyryl or tigloyl at the 3 or 4 positions. Alternatively at the 21 position there is provided tigloyl, benzoyl or dibenzoyl substituents.

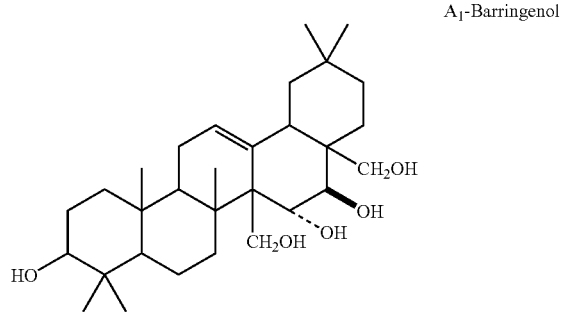

A₁-Barringenol

25 Claims, 35 Drawing Sheets

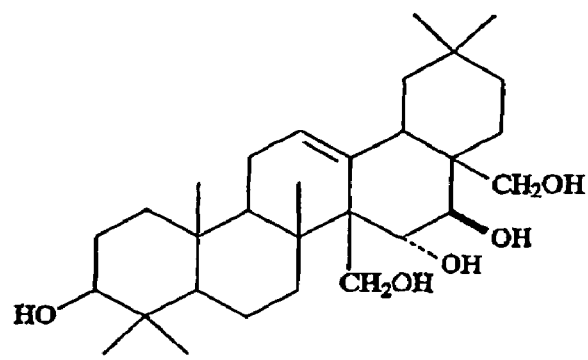
FIG 1. $A_1$-Barringenol
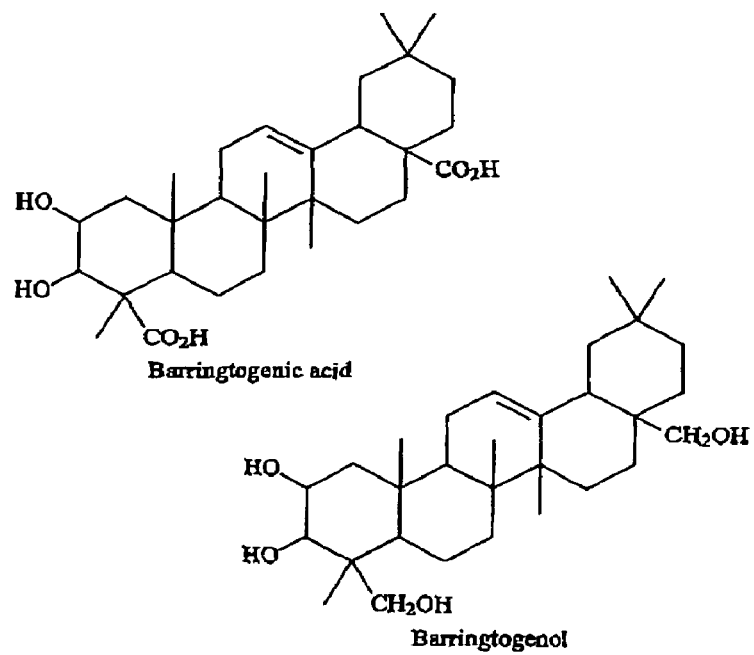
FIG 2. The structure of barringtogenic acid and barringtogenol

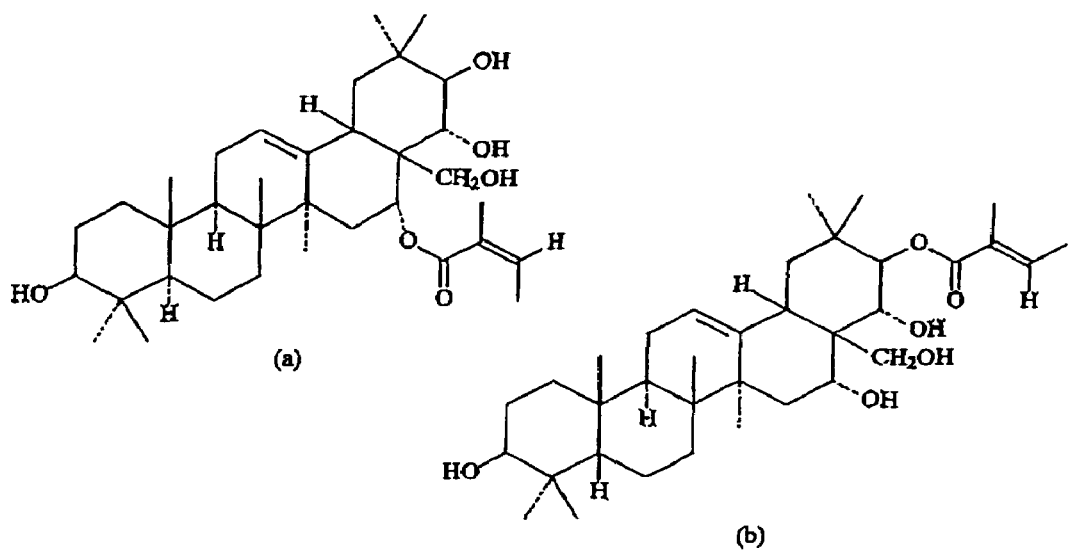
FIG 3 (a) Initial and (b) revised structures of barringtogenol B
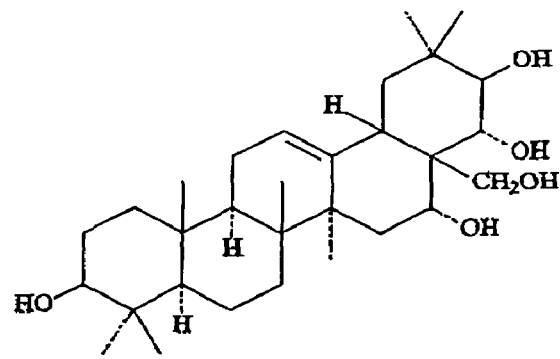
FIG 4 Barringtogenol C
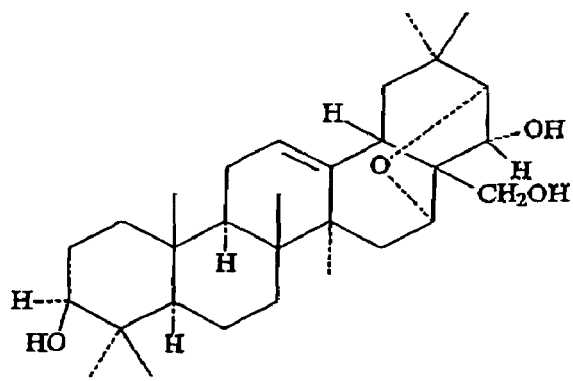
FIG 5 – Barringtogenol D

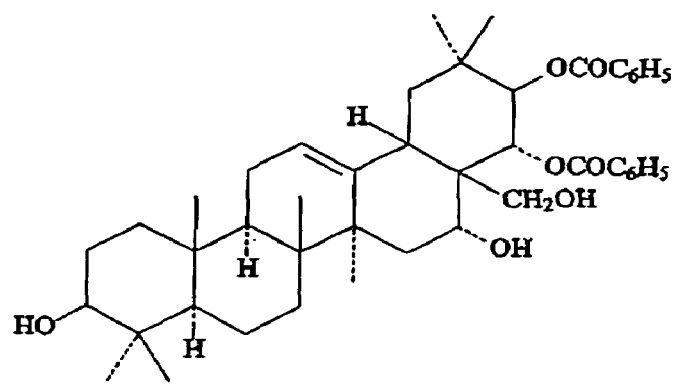
FIG 6 – Barringtogenol E
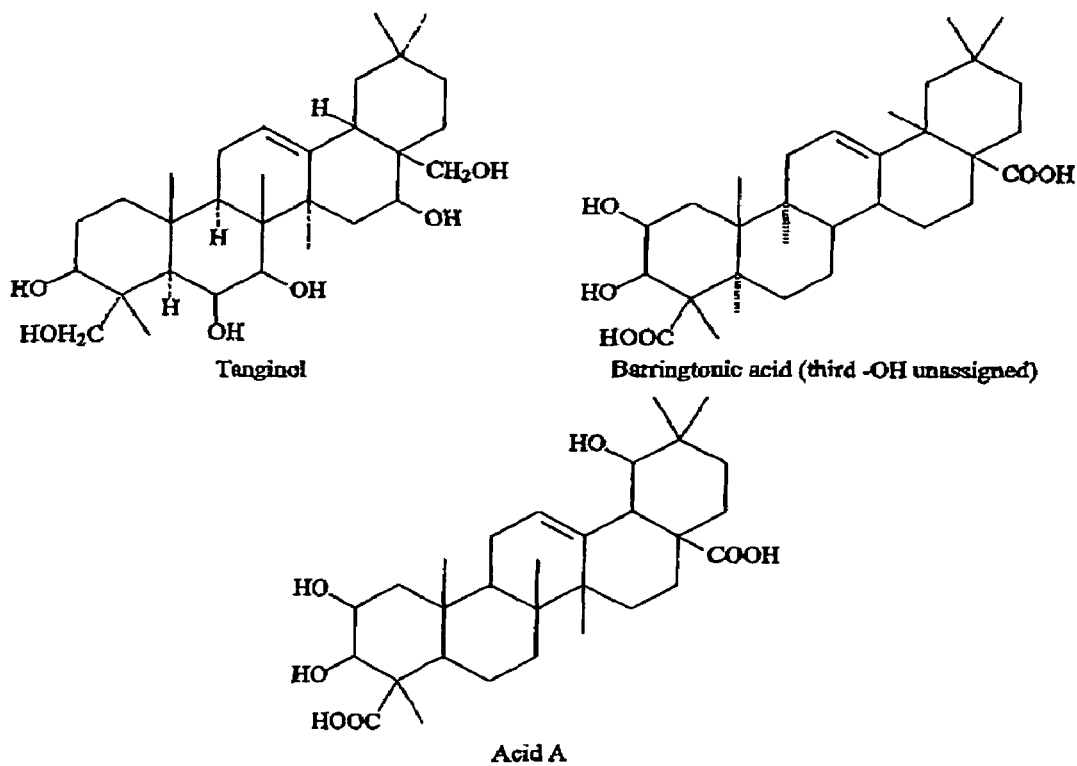
**FIG 7 – Compounds from *B. acutangula***

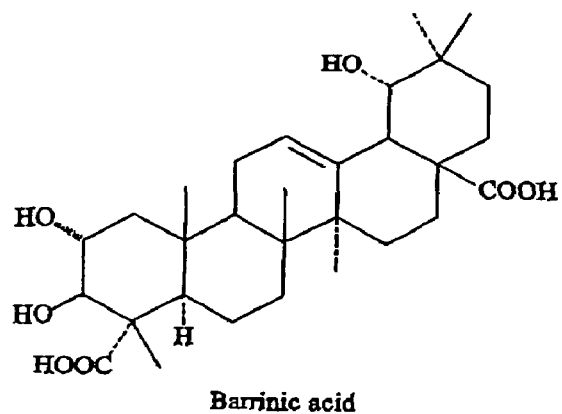
FIG 8. Barrinic acid
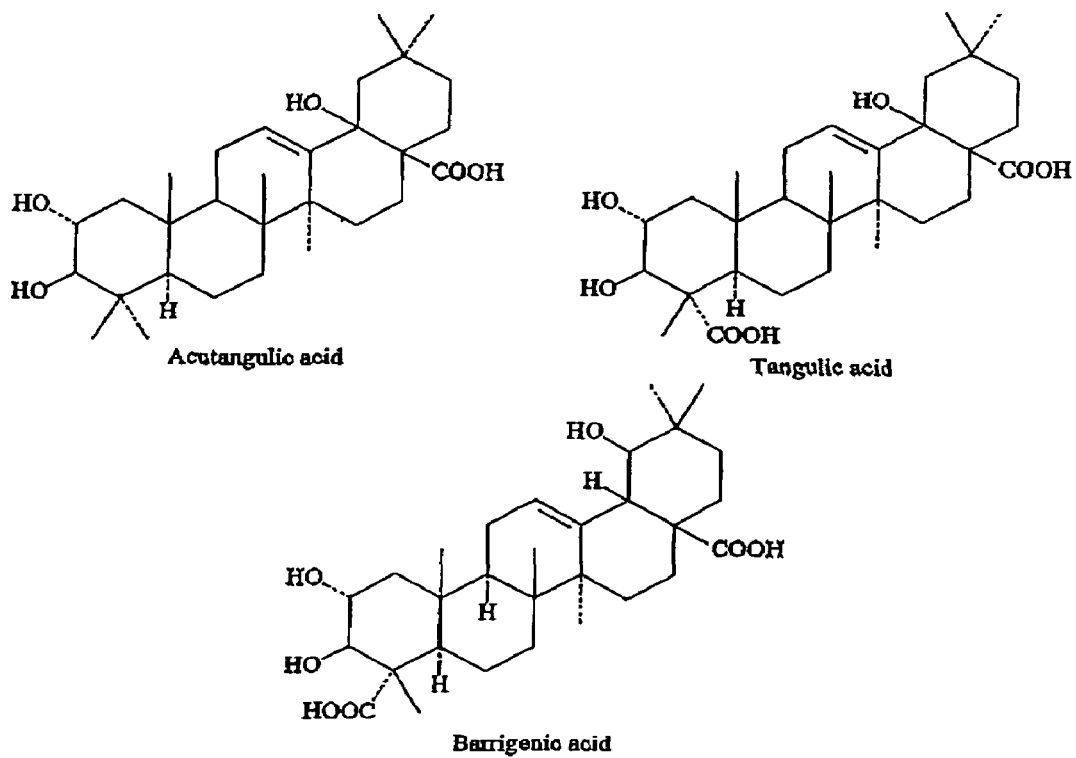
FIG 9 – Compounds from B. acutangula

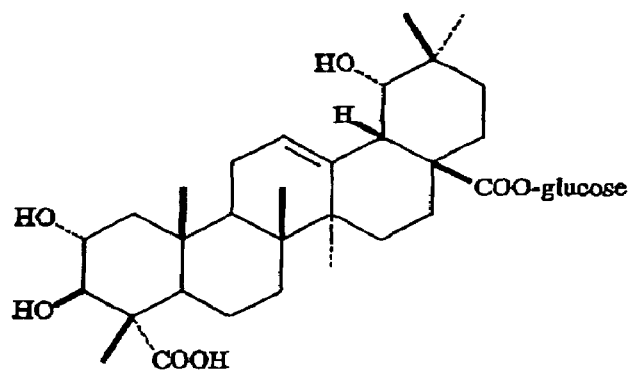
FIG 10 - 2α,3β,19α-trihydroxy-olean-12-ene-dioic acid 28-O-β-D-glucopyranoside from the seeds of B. acutangula

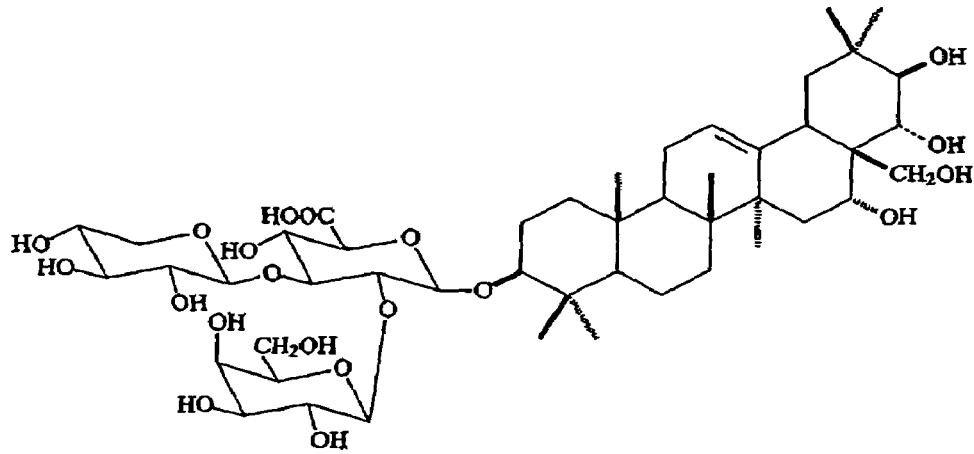
Barringtoside A = 3-O-β-D-xylopyranosyl(1→3)-[β-D-galactopyranosyl(1→2)]-β-D-glucuronopyranosyl barringtogenol C
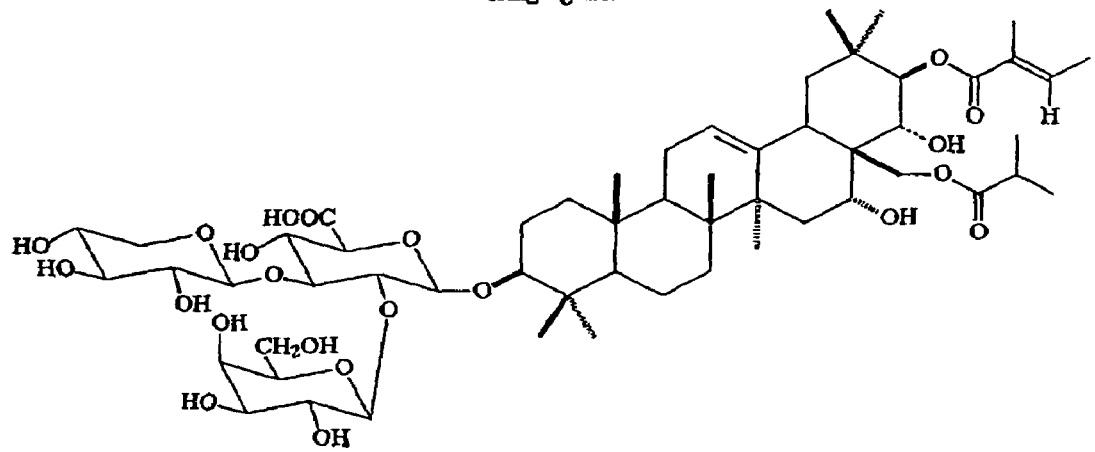
Barringtoside B = 3-O- β-D-xylopyranosyl(1→3)-[β-D-galactopyranosyl(1→2)]-β-D-glucuronopyranosyl -21-O-tigloyl-28-O-isobutyryl barringtogenol C
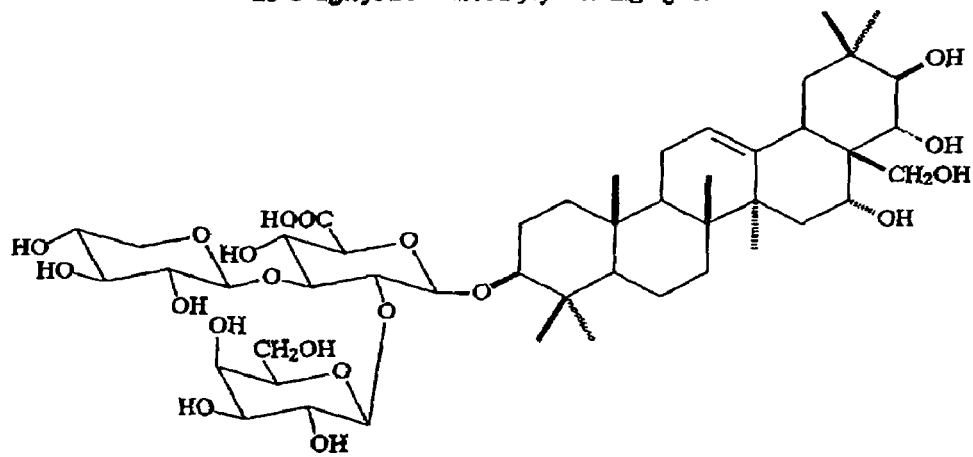
Barringtoside C = 3-O-α-L-arabinopyranosyl(1→3)-[β-D-galactopyranosyl(1→2)]-β-D-glucuronopyranosyl barringtogenol C
FIG 11

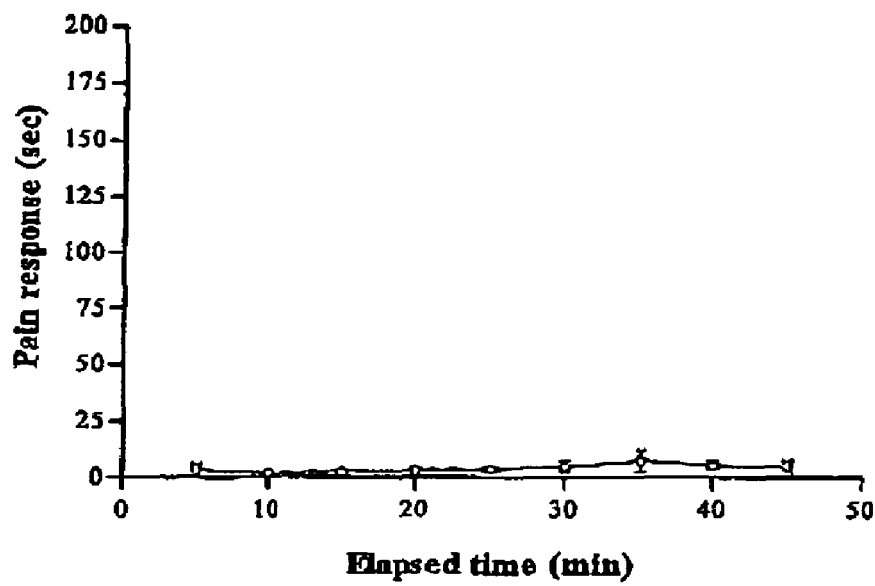
FIG 12 – Normal grooming response ($\bar{x}$ ± S.E.; n = 6).
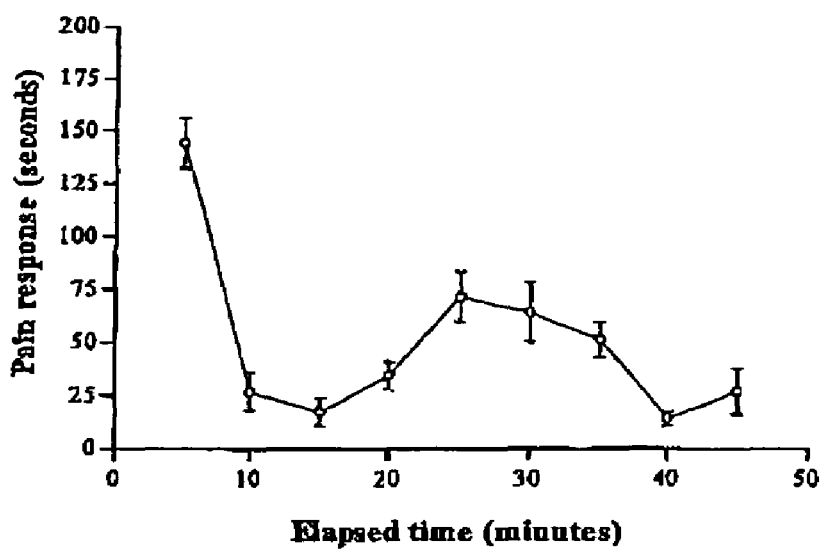
FIG 13 – Control values ($\bar{x}$ ± S.E.; n = 18).

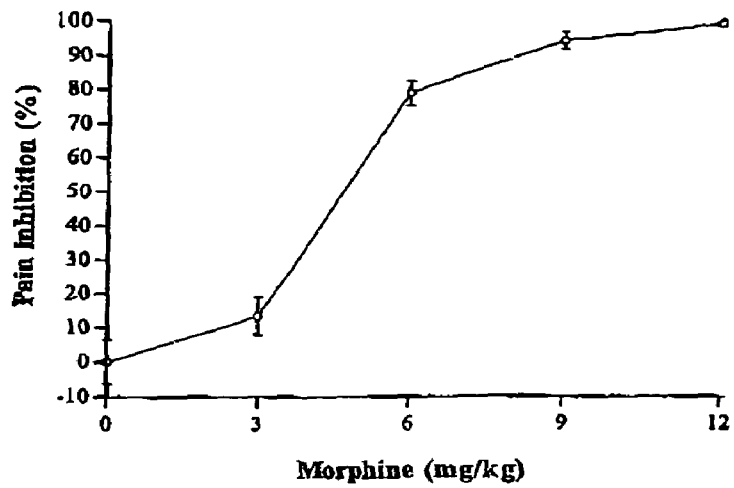
FIG 14 - Dose response curve for morphine ($\bar{x}$ ± S.E.; n = 6(min)).
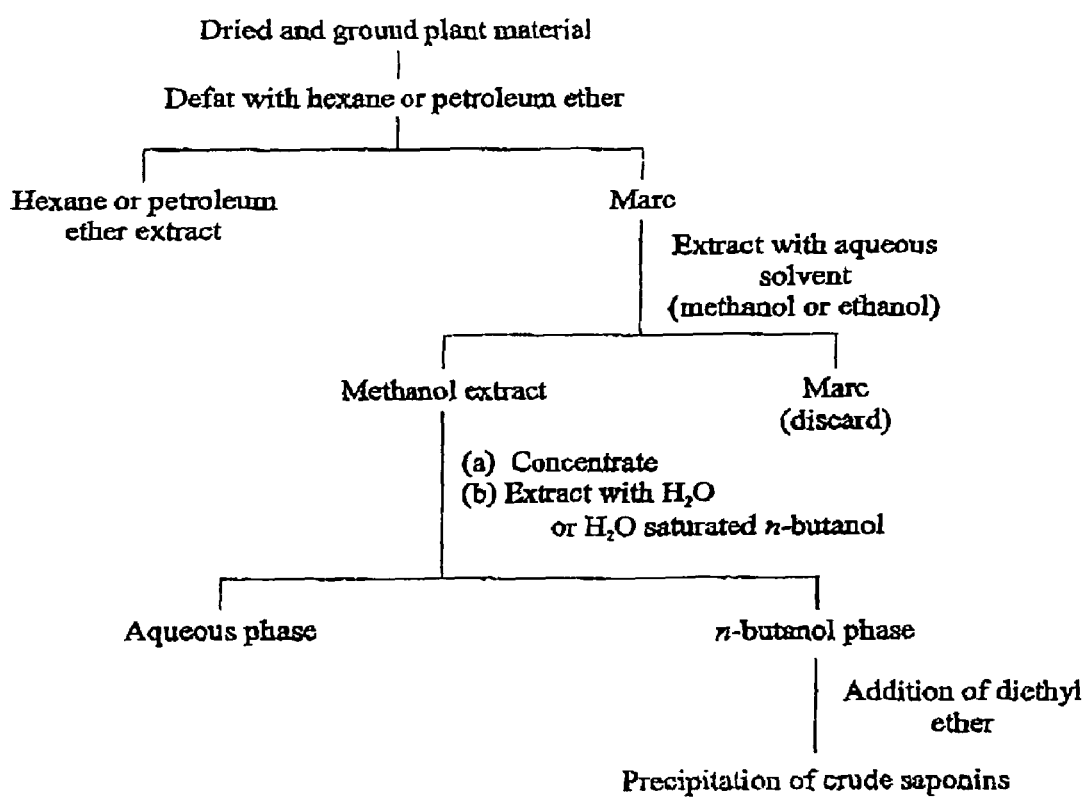
FIG 15 - Schematic for the preparation of crude saponin mixtures.

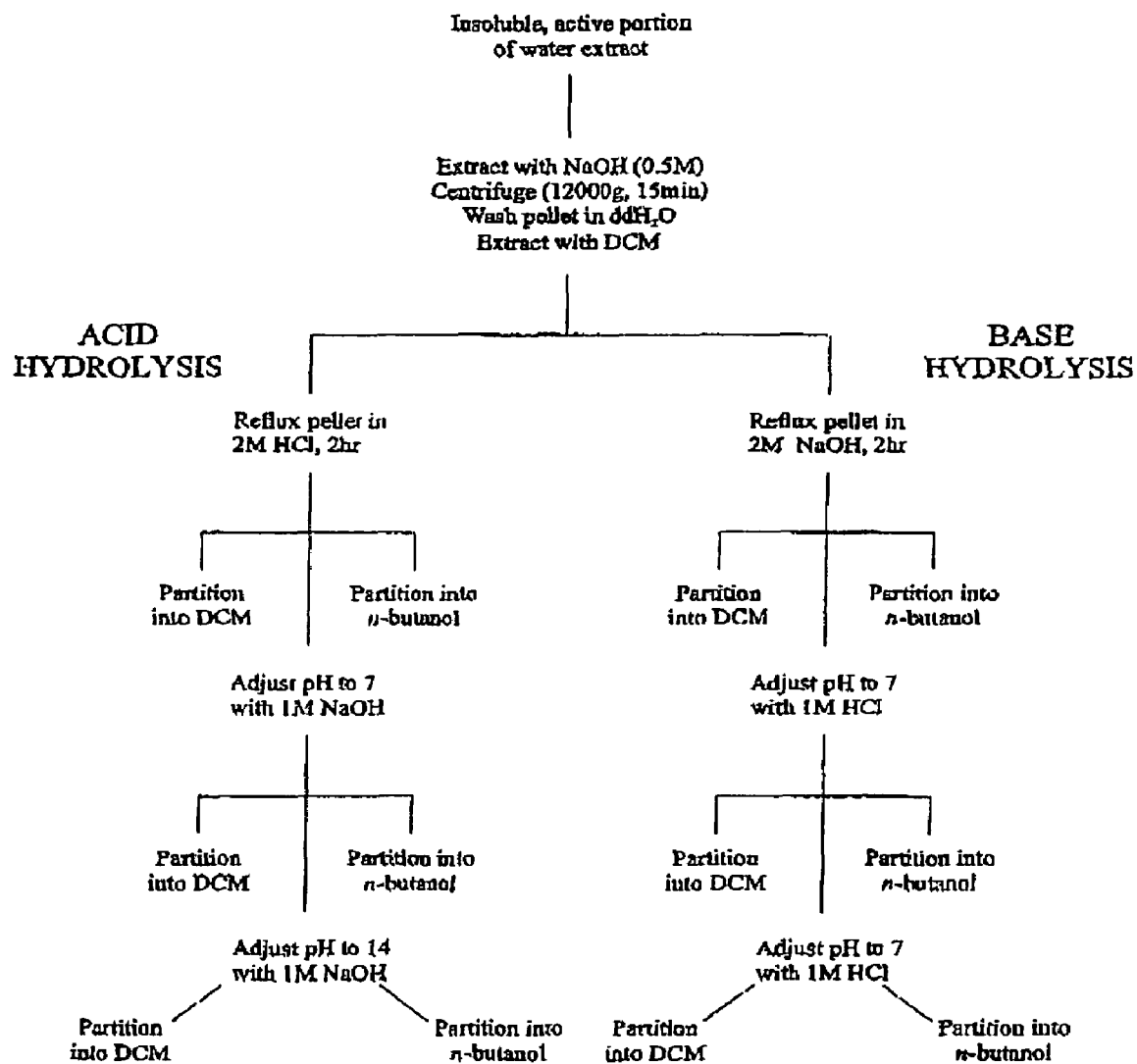
FIG 16 - Acid and base hydrolysis scheme.

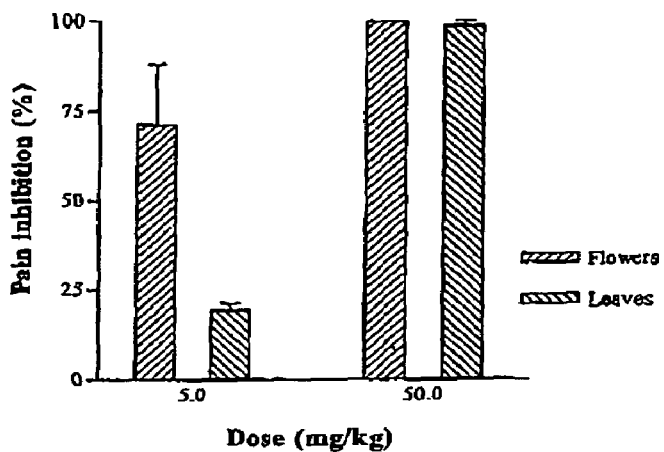
FIG 17 - Analgesic activity of water extract of flowers and leaves of *B. acutangula* ($\bar{x} \pm$ SE, n=2).
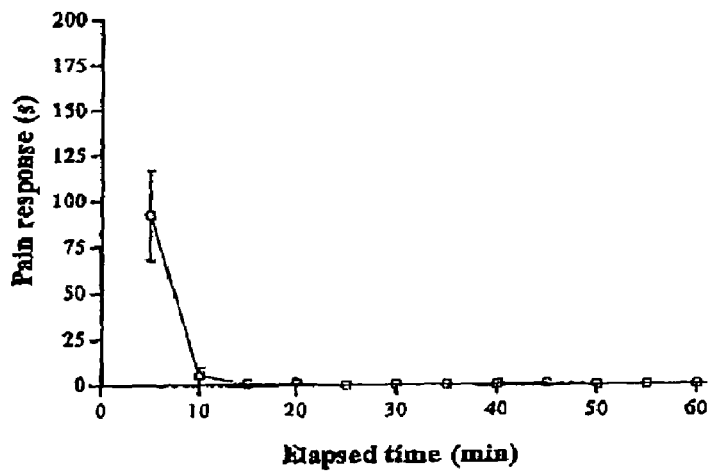
FIG 18 - Analgesic activity of crude water extract ($\bar{x} \pm$ SE, n=5).

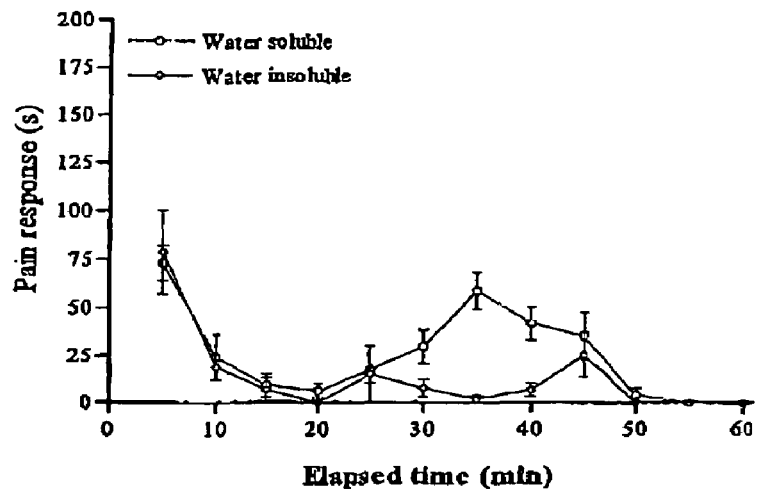
FIG 19 - Analgesic activity of crude water soluble (n=9) and insoluble (n=4) portions of the water extract ($\bar{x} \pm$ SE).
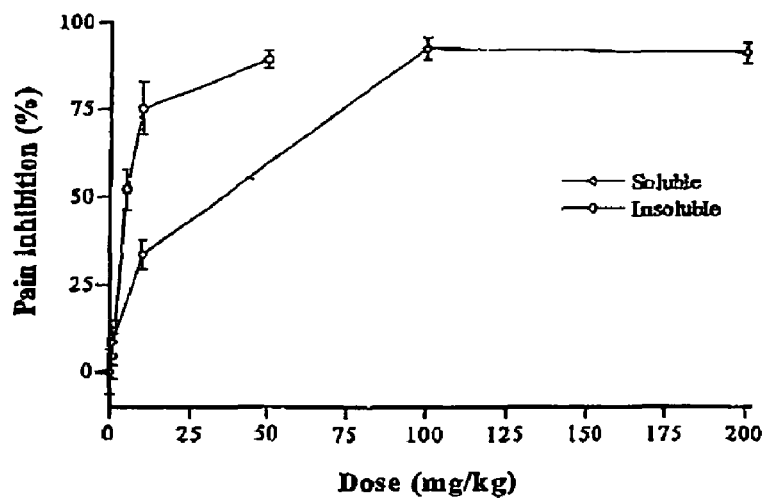
FIG 20 - Dose response curves for water extract ($\bar{x} \pm$ SE, n=4).

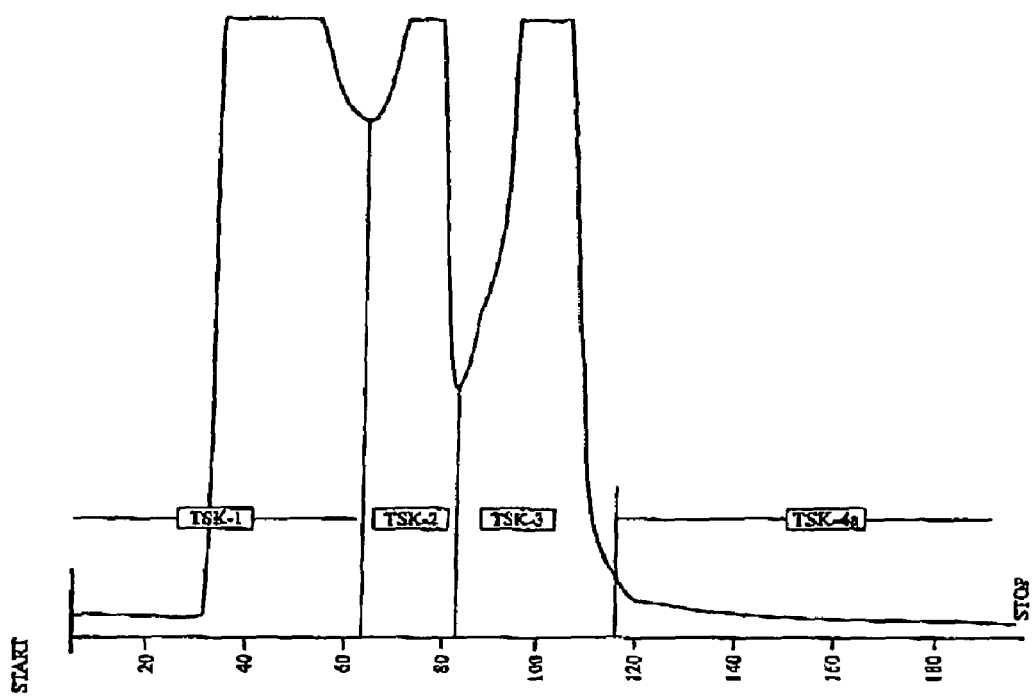
FIG 21 - Preparative gel permeation column.
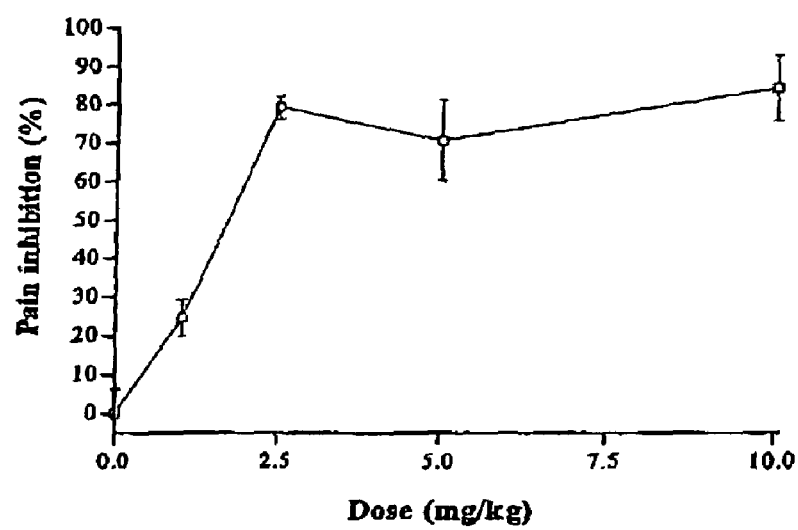
FIG 22 - Dose response curve for TSK-4a ($\bar{x} \pm$ SE, n=3).

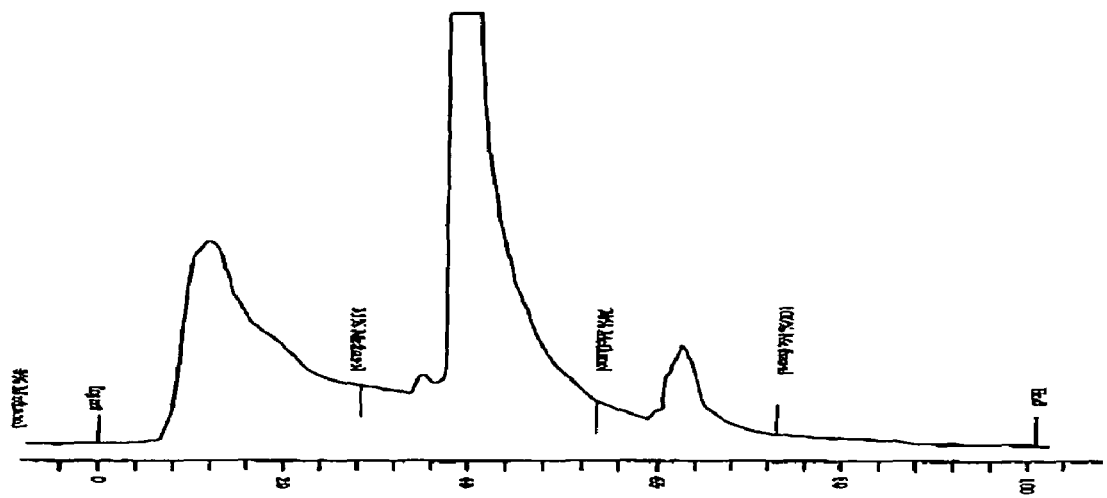
FIG 23 - C18 separation of TSK-4a.
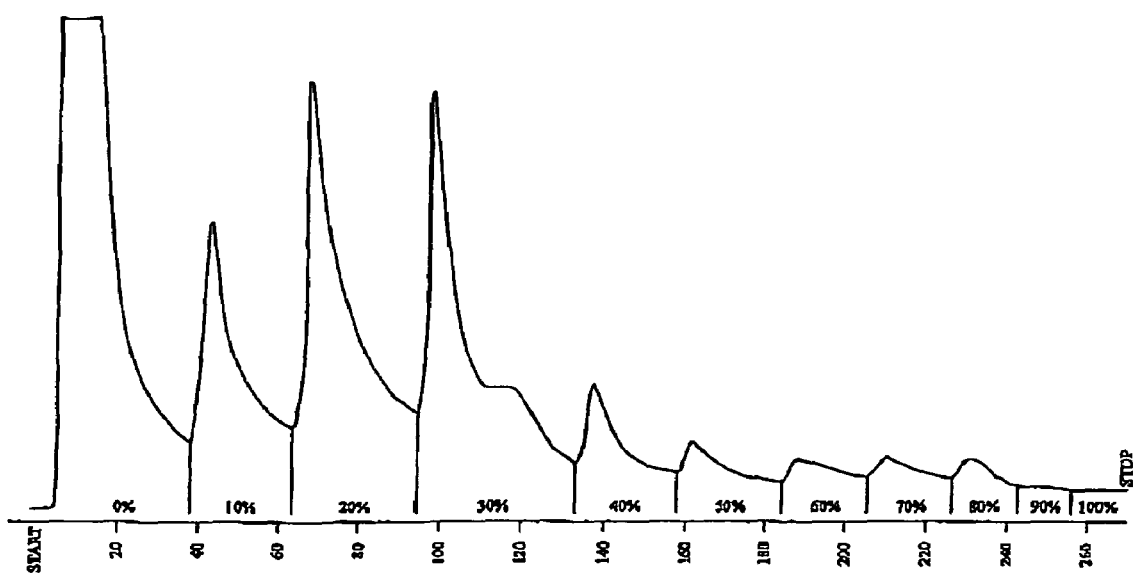
FIG 24 - C18 preparative separation of TSK-4a.

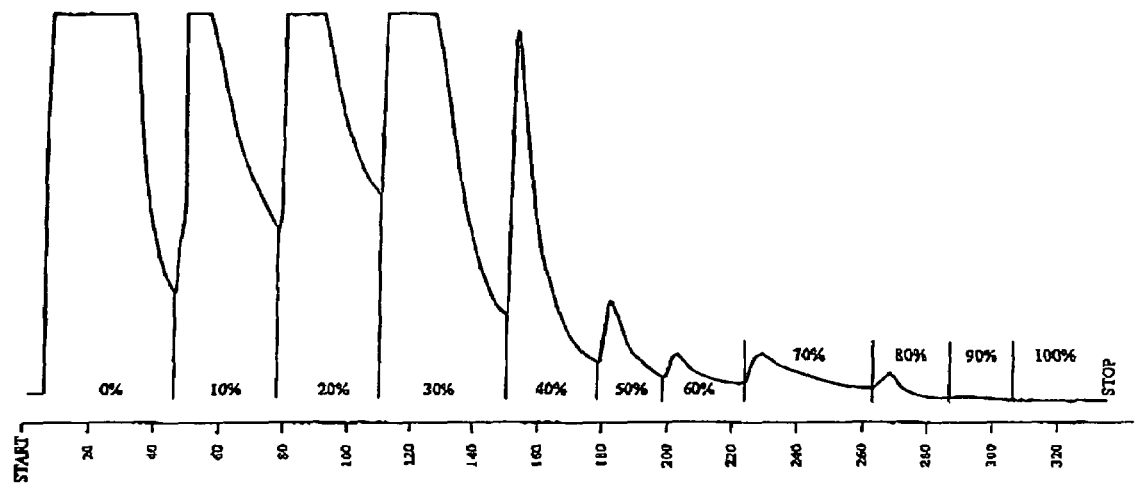
FIG 25 - Preparative C18 chromatogram of H₂O extract
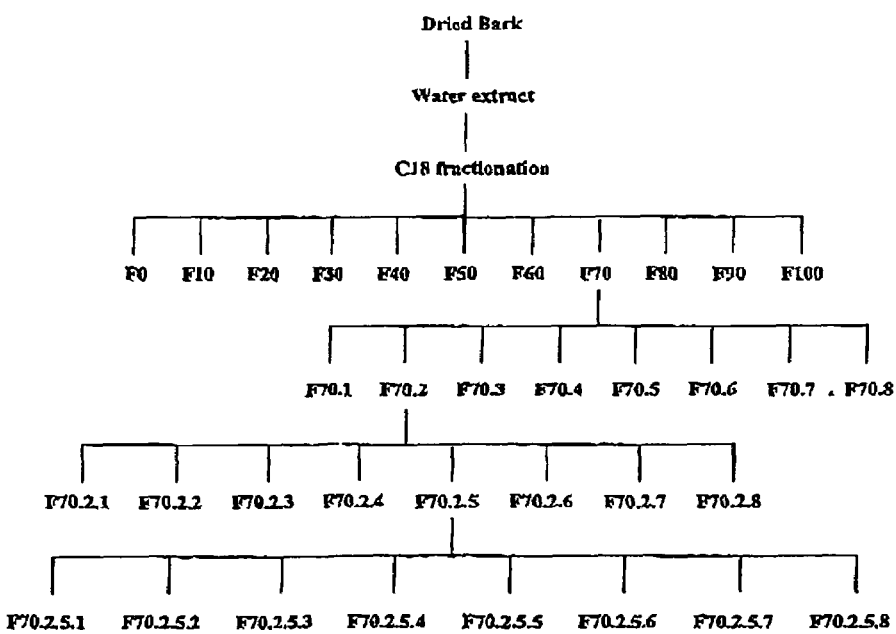
FIG 26 - Outline of numbering system compound F70.2.5.2.

Analytical separations
Preparatory separations
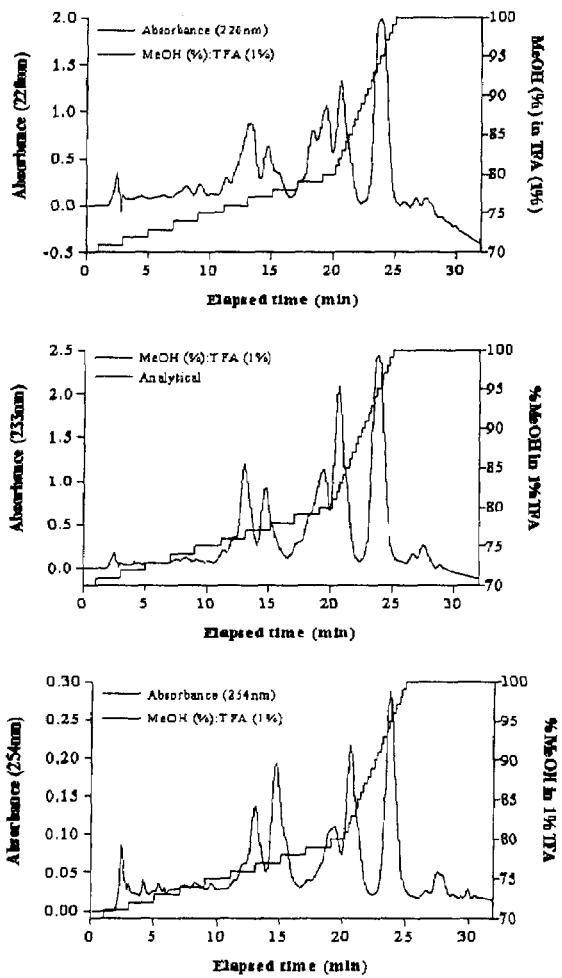
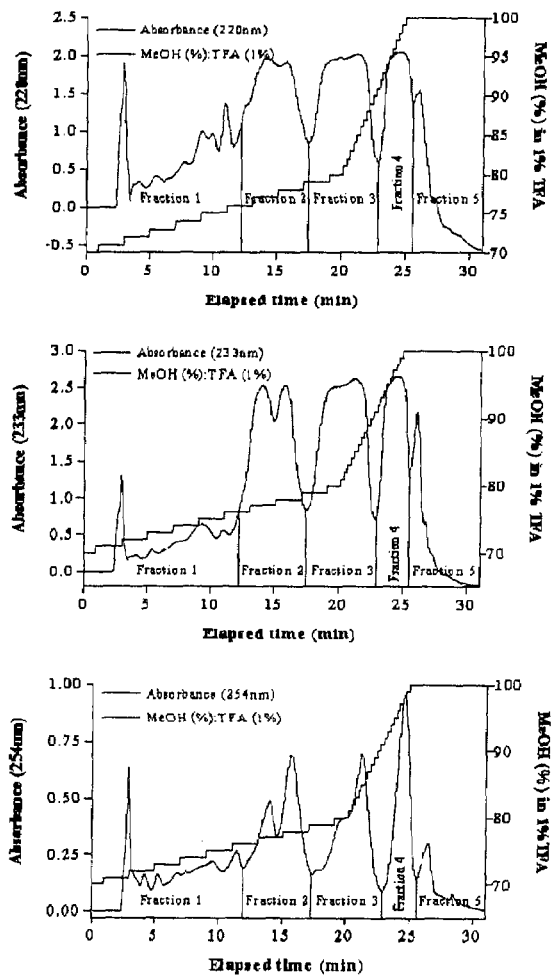
FIG 27 - Separation of fraction eluting at 70% MeOH (F70).

Analytical separations
Preparatory separations
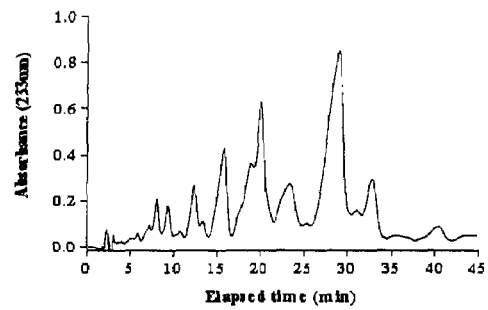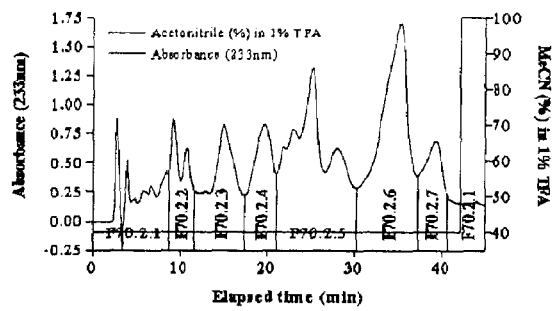
FIG 28 - Separation of fraction F70.2 (40%MeCN in 1%TFA).
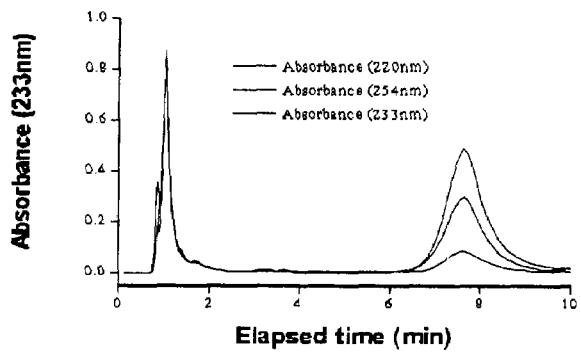
FIG 29 - Chromatogram of F70.2.6.
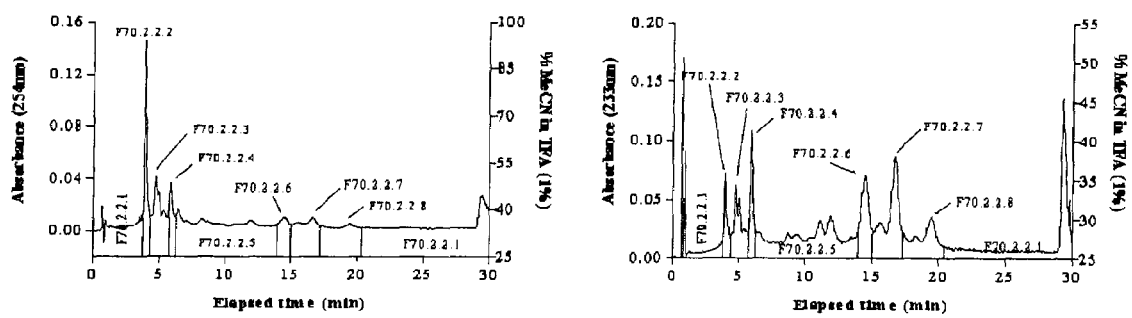
FIG 30 - Separation of fraction F70.2.2 at 254nm (left) and 233nm (right).

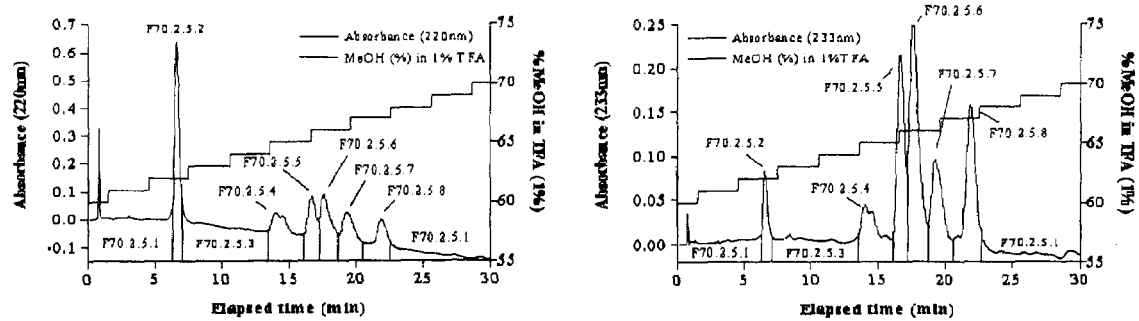
FIG 31 - Separation of fraction F70.2.5 at 220nm (left) and 233nm (right).
Analytical separations 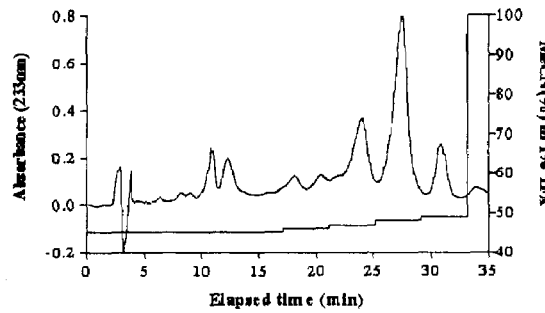 Preparatory separations 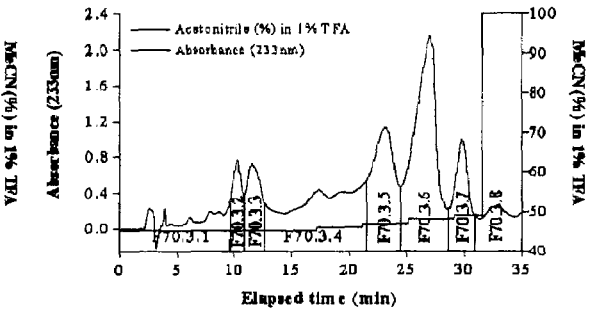
FIG 32 - Separation of fraction F70.3.
Fraction F70.3.5 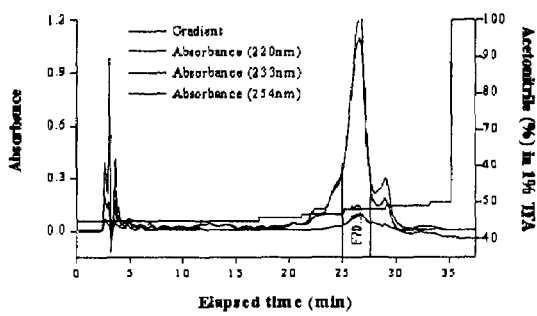 Fraction F70.3.7 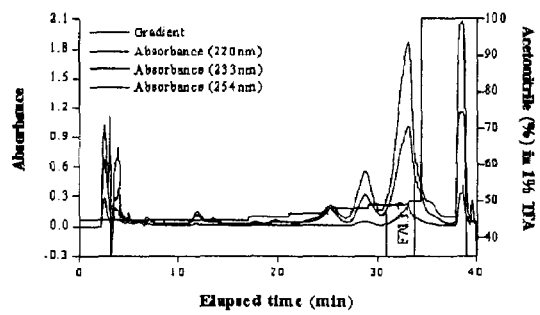
FIG 33 - Chromatograms of F70.3.5 and F70.3.7.

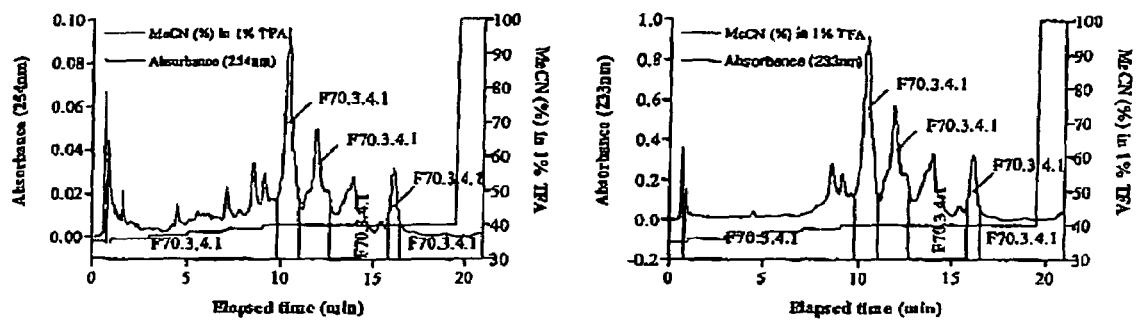
FIG 34 - Analytical separation of fraction F70.3.4 at 254 and 233nm.
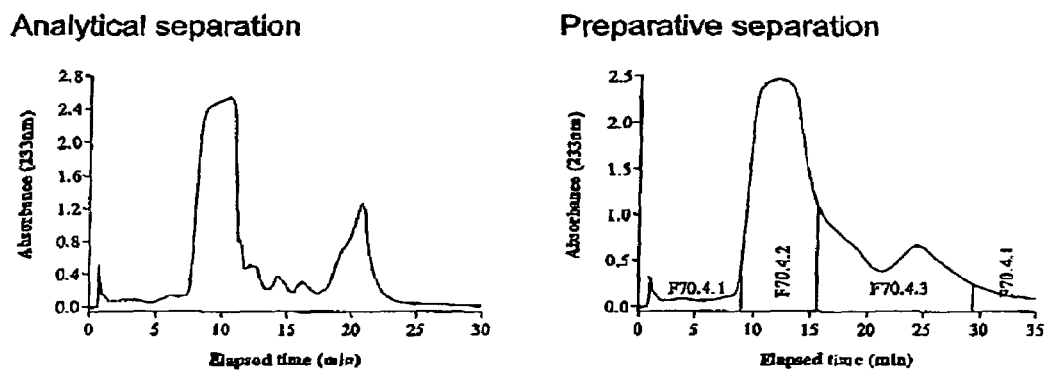
FIG 35 - Separation of F70.4.
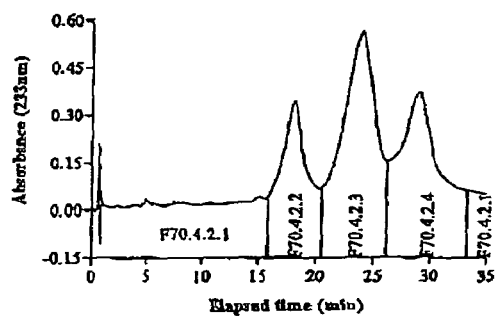
FIG 36 - Separation of F70.4.2.

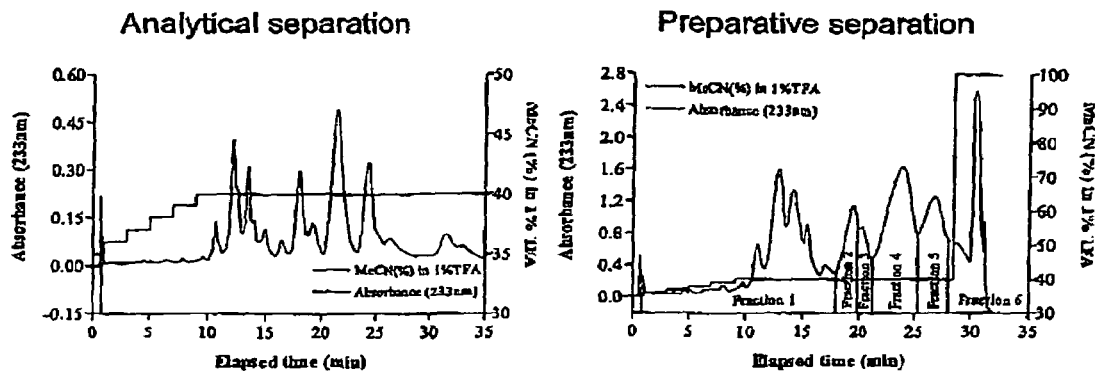
FIG 37 – Analytical separation (left) and preparative separation (right) of F70.4.3.
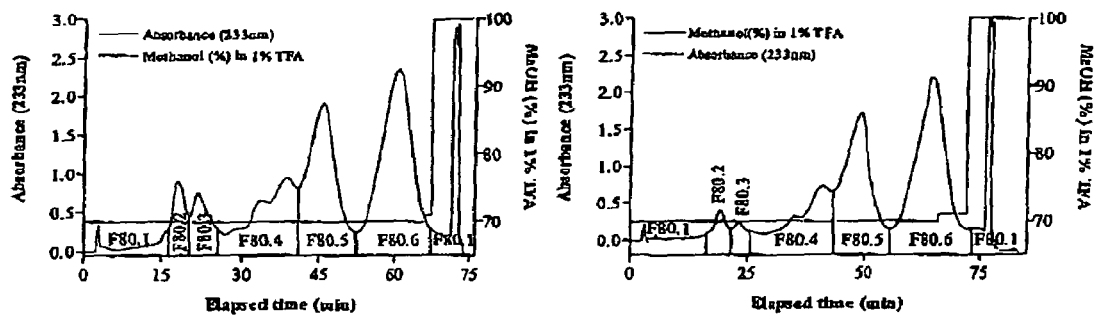
FIG 38 - Preparative chromatograms showing loss of peaks F80.2 & F80.3.
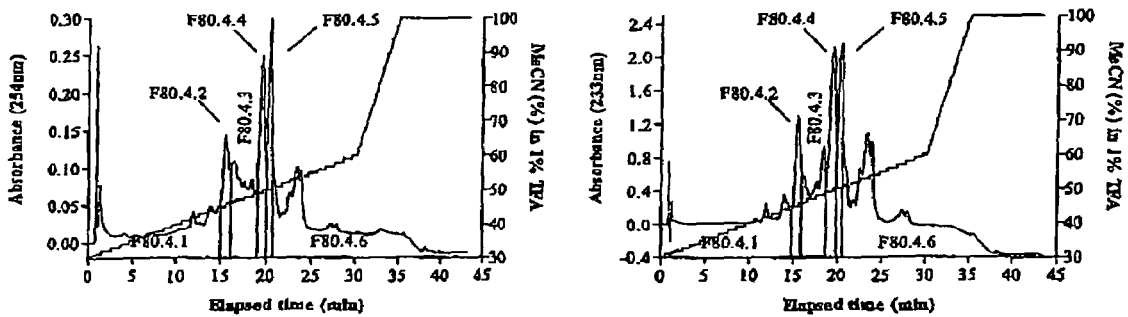
FIG 39 - Preparative chromatograms of F80.4.

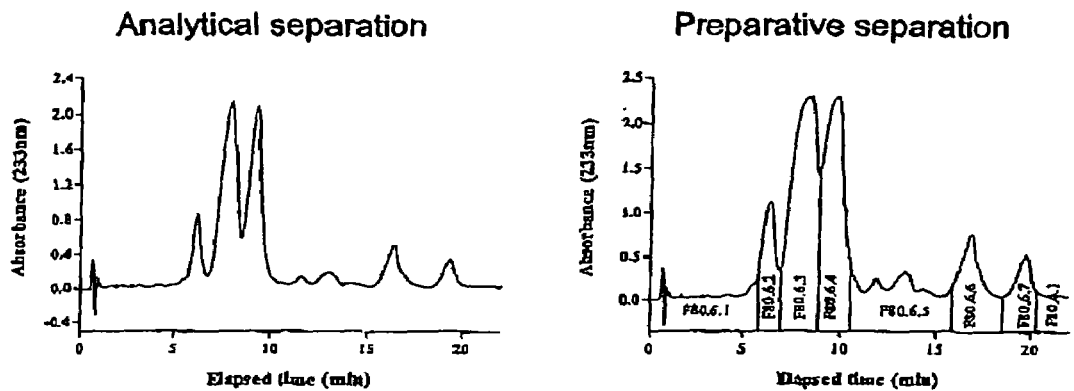
FIG 40 - Separation of fraction F80.6 using a phenyl reverse phase column with the analytical separation (left) and the preparative separation (right).
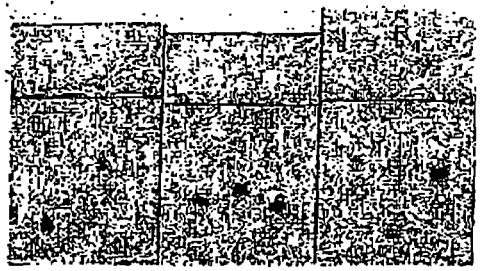
FIG 41 - Standard sugars used for TLC
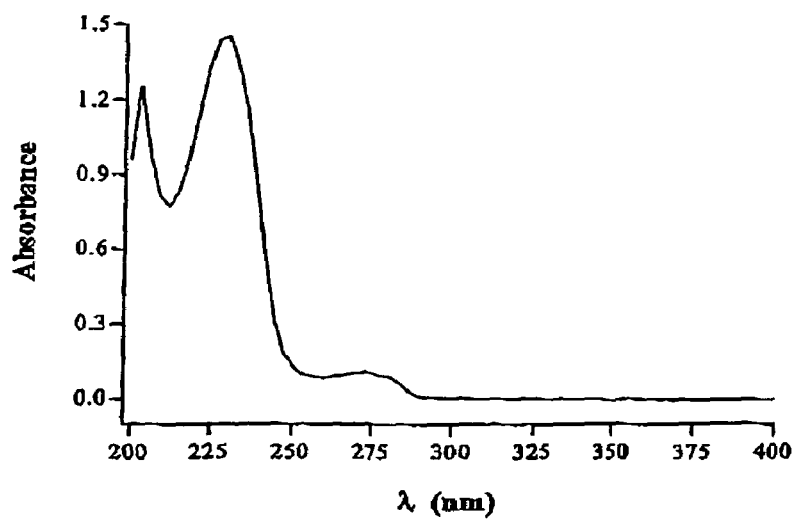
FIG 42 - UV spectrum of F70.3.6

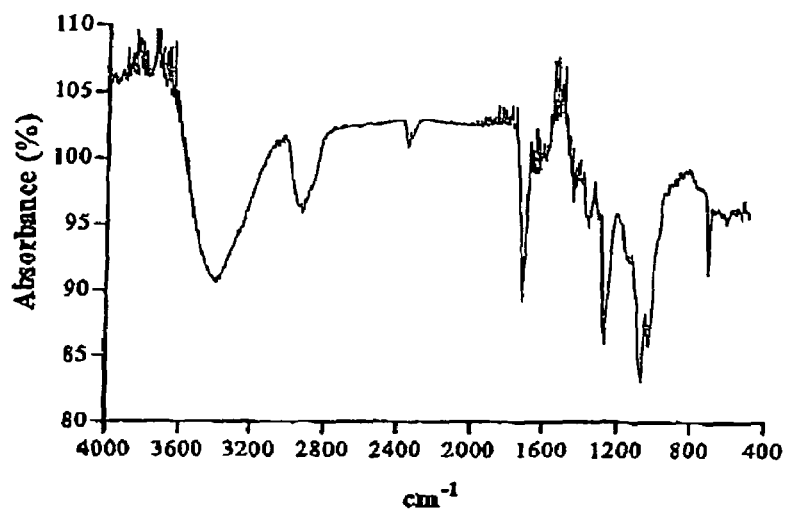
FIG 43 - FTIR spectrum of F70.3.6
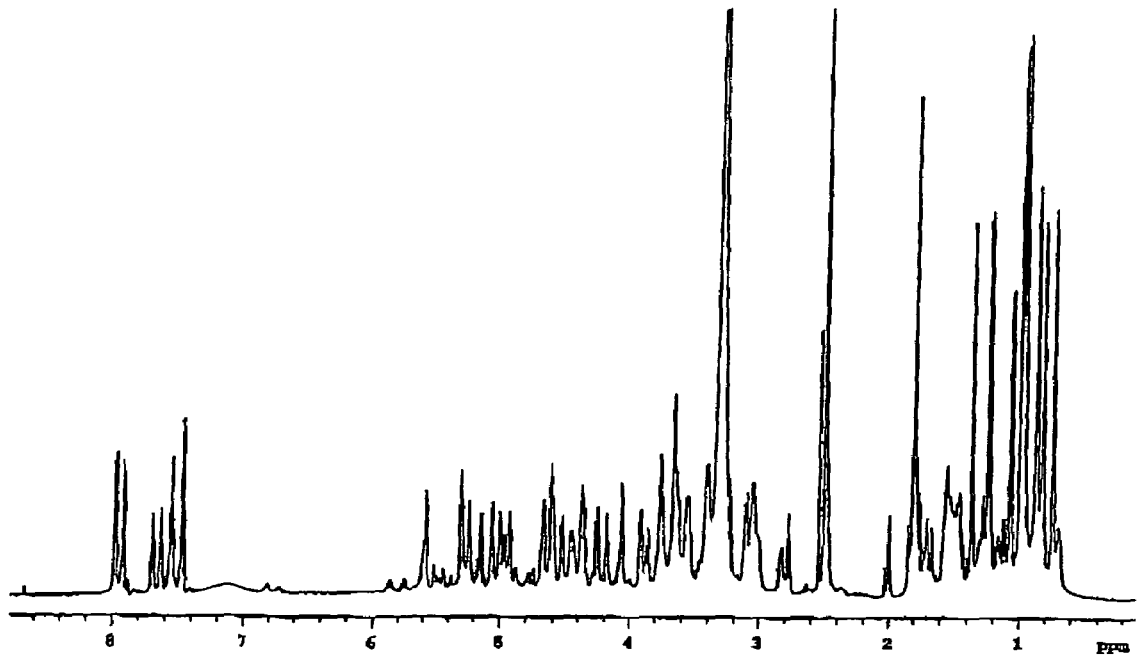
FIG 44 - ¹H-NMR for compound F70.3.6

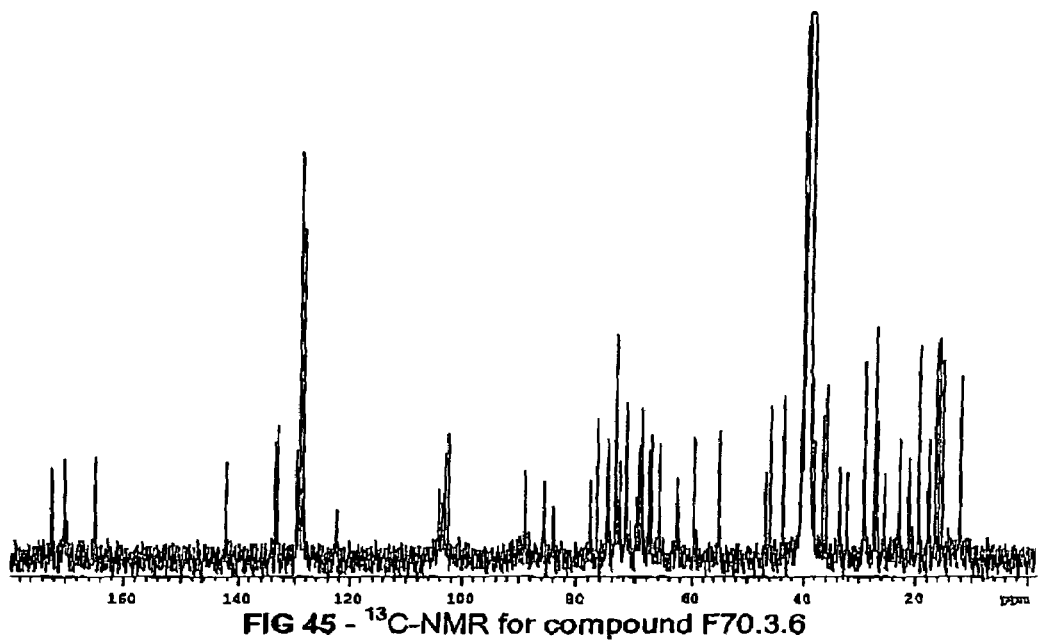
FIG 45 - $^{13}$C-NMR for compound F70.3.6
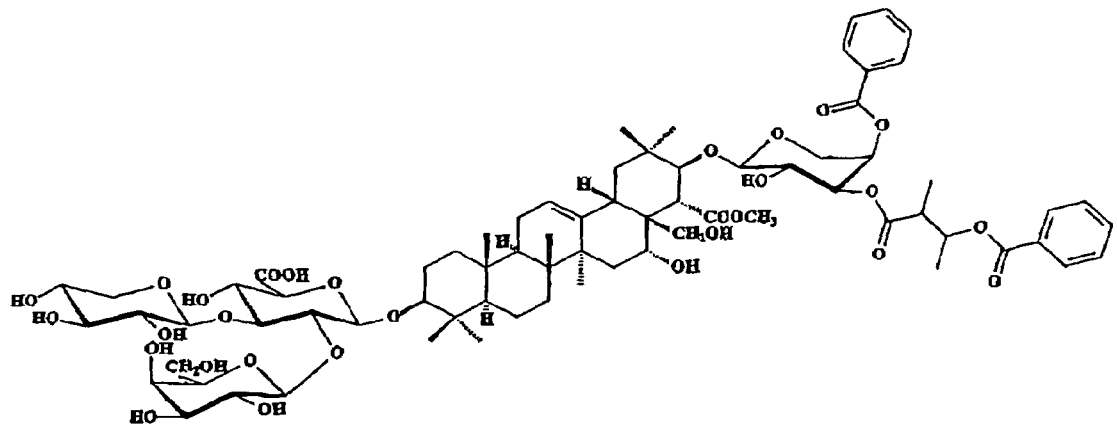
FIG 46 - The complete assignment of F70.3.6
(3-O-ß-D-xylopyranosyl(1? 3)-[ß-D-galactopyranosyl(1? 2)]-ß-D-glucuronopyranosyl-21-O-[3-(3-benzoyl-2-methylbutanoyl)-4-benzoyl-α-L-arabinopyranosyl]-22-O-acetyl barringtogenol C)

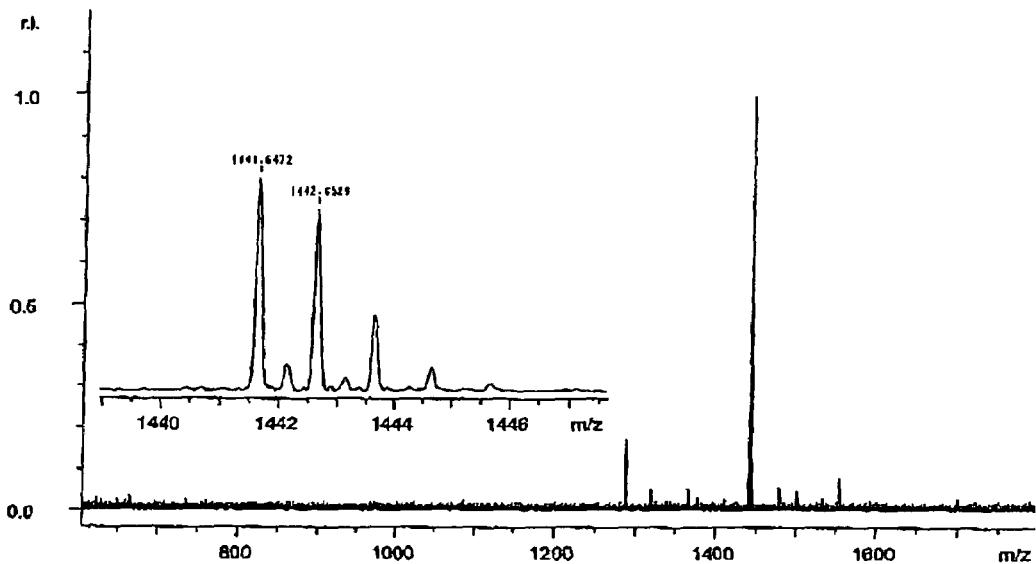
FIG 47 - Negative ion HR-ESMS of F70.3.6 (insets show detail of molecular ion)
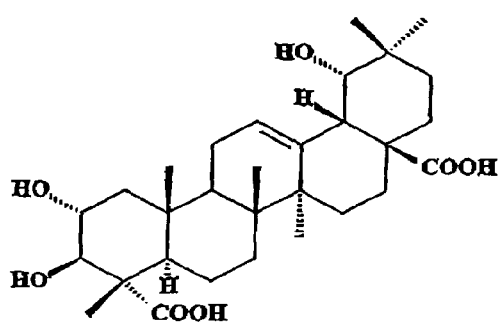
FIG 48 - Compound F70.2.5.2
($2\alpha$, $3\beta$, $19\alpha$-trihydroxy-olean-12-ene-23, 28-dioic acid)

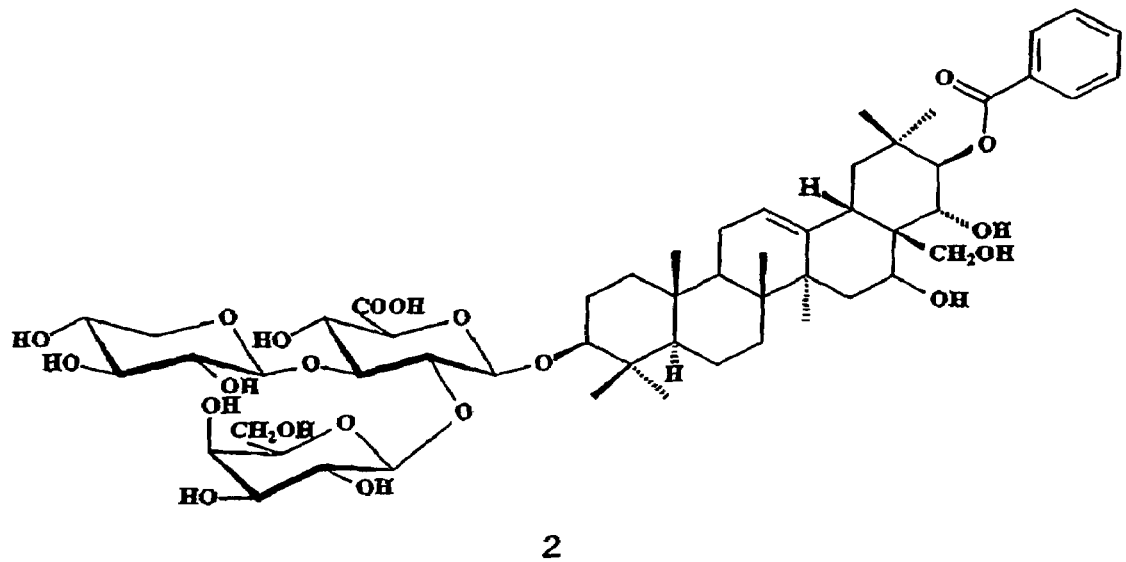
FIG 49 - Compound F70.2.3.
*(3-O-ß-D-xylopyranosyl(1→3)-[ß-D-galactopyranosyl(1→2)]-ß-D-glucuronopyranosyl-21-O-benzoyl barringtogenol C)*
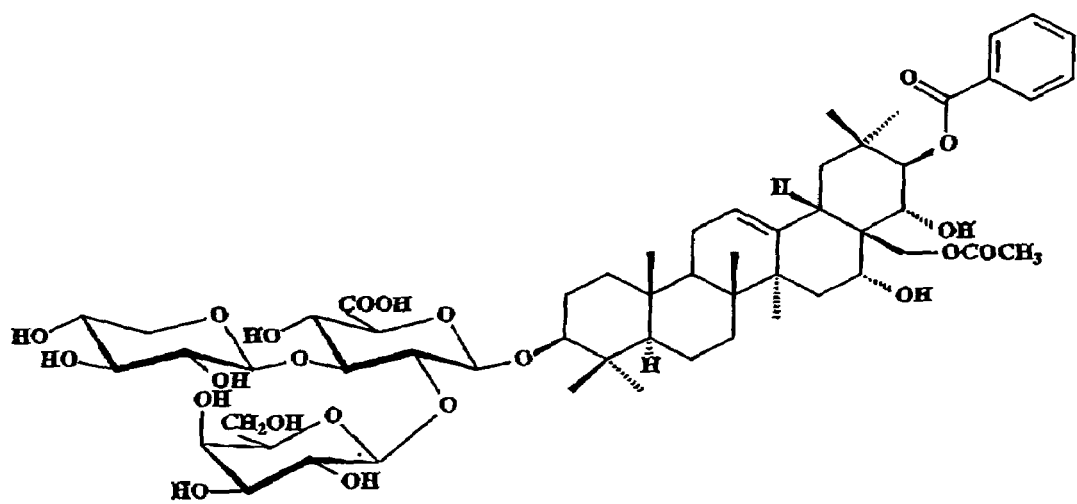
FIG 50 - Compound F70.3.2
*3-O-ß-D-xylopyranosyl(1→3)-[ß-D-galactopyranosyl(1→2)]-ß-D-glucuronopyranosyl-21-O-benzoyl-28-O-acetyl barringtogenol C)*

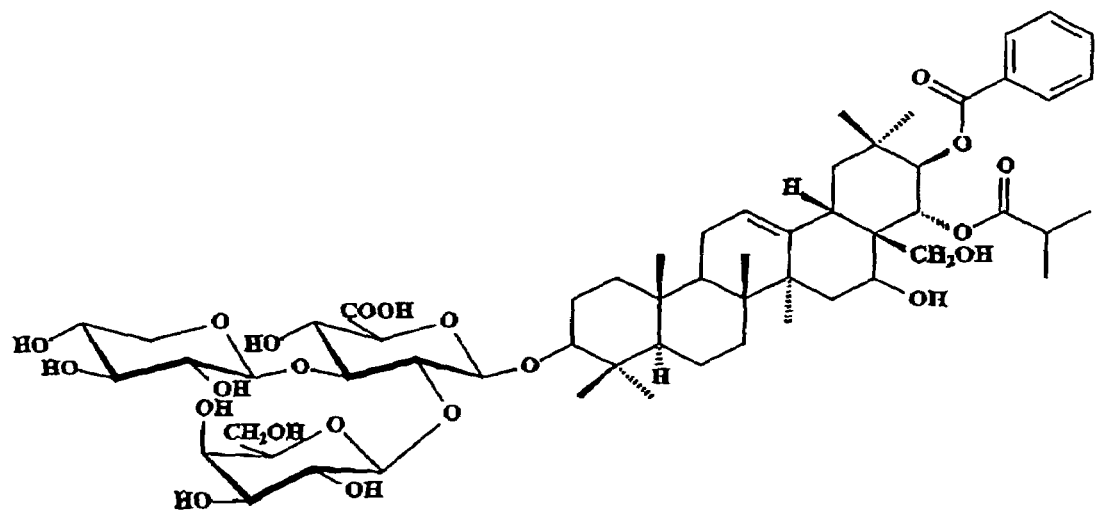
FIG 51 - Compound F70.3.4.2
(3-O-ß-D-xylopyranosyl(1→3)-[ß-D-galactopyranosyl(1→2)]-ß-D-glucuronopyranosyl-21-O-benzoyl-22-O-isobutyryl barringtogenol C)
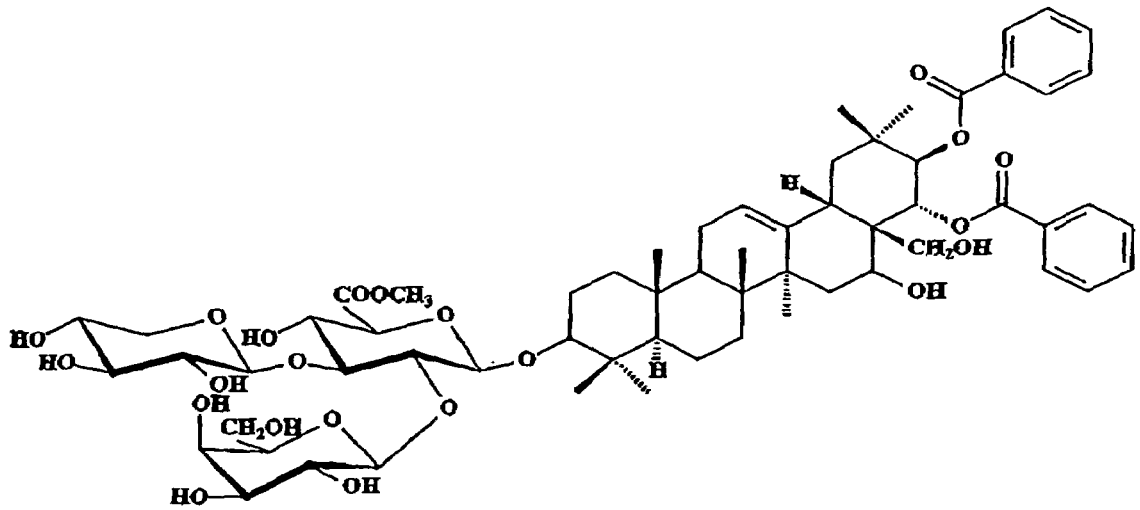
FIG 52 - Compounds F70.4.3.5.2/F80.6.7
(3-O-ß-D-xylopyranosyl(1→3)-[ß-D-galactopyranosyl(1→2)]-β-D-methylglucuronopyranosyl-21,22-O-dibenzoyl barringtogenol C)

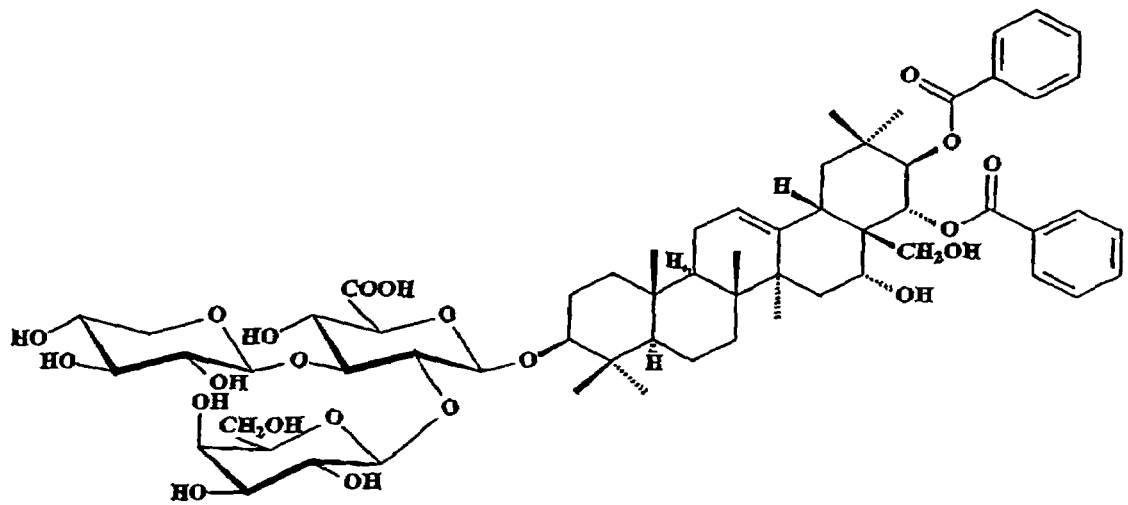
FIG 53 - Compound F80.6.4/F70.4.2.4.2
(3-O-ß-D-xylopyranosyl(1→3)-[ß-D-galactopyranosyl(1→2)]-ß-D-glucuronopyranosyl-21, 22-O-dibenzoyl barringtogenol C
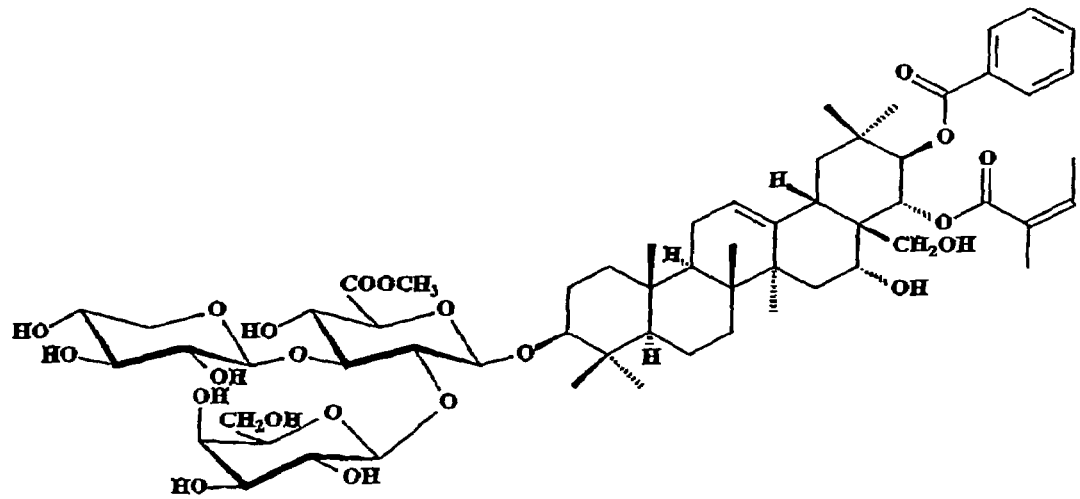
FIG 54 - Compound F70.4.3.4.2/F80.6.6
(3-O-ß-D-xylopyranosyl(1→3)-[ß-D-galactopyranosyl(1→2)]-ß-D-methylglucuronopyranosyl-21-O-benzoyl-22-O-tigloyl barringtogenol C)

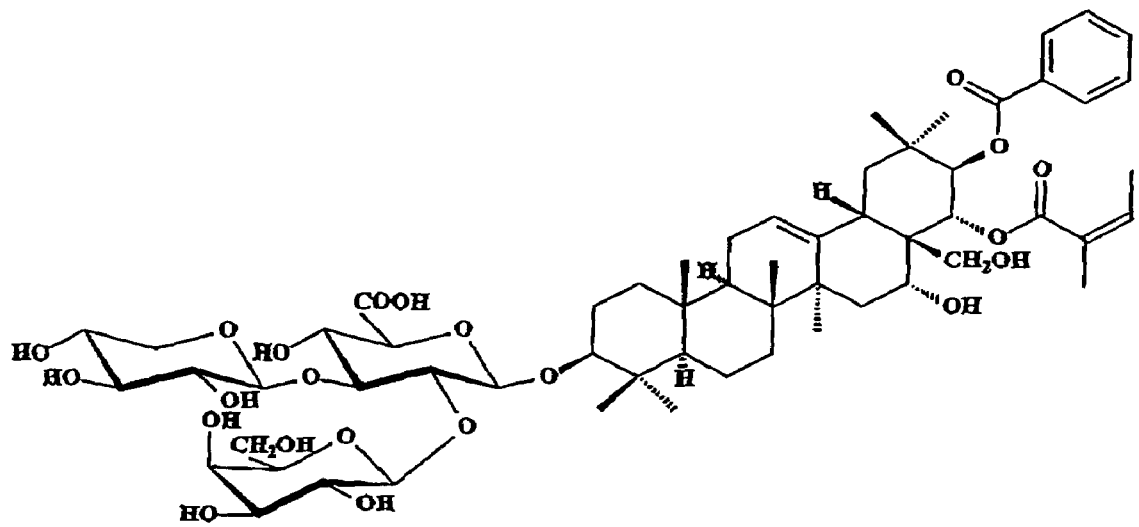
FIG 55 - Compound F70.4.2.3/F80.6.3
*(3-O-ß-D-xylopyranosyl(1→3)-[ß-D-galactopyranosyl(1→2)]-ß-D-glucuronopyranosyl-21-O-benzoyl-22-O-tigloyl barringtogenol C)*
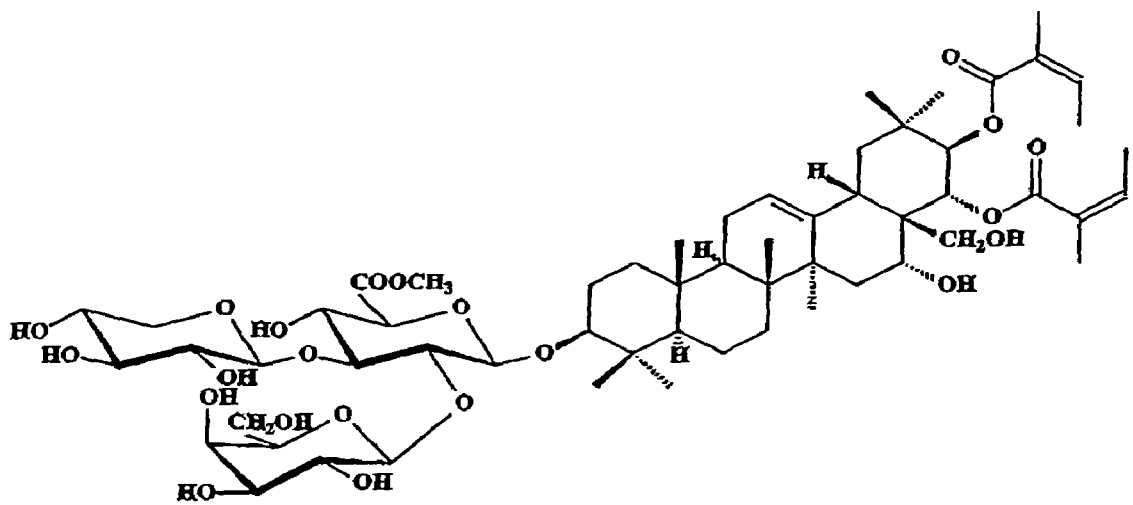
FIG 56 - Compound F70.4.3.2.2
*(3-O-ß-D-xylopyranosyl(1→3)-[ß-D-galactopyranosyl(1→2)]-ß-D-methylglucuronopyranosyl-21,22-O-tigloyl barringtogenol C)*

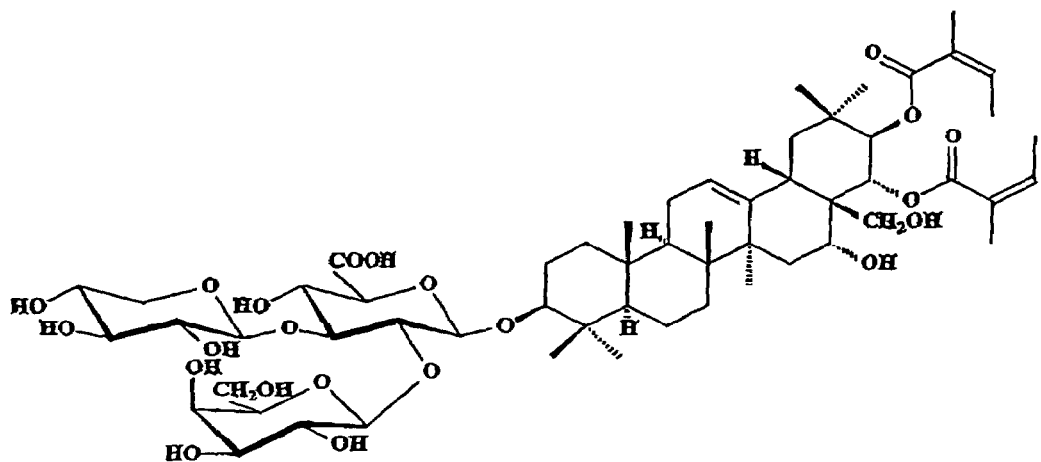
FIG 57 - Compound F80.6.2
*(3-O-ß-D-xylopyranosyl(1→3)-[ß-D-galactopyranosyl(1→2)]-ß-D-glucuronopyranosyl-21,22-O-tigloyl barringtogenol C)*
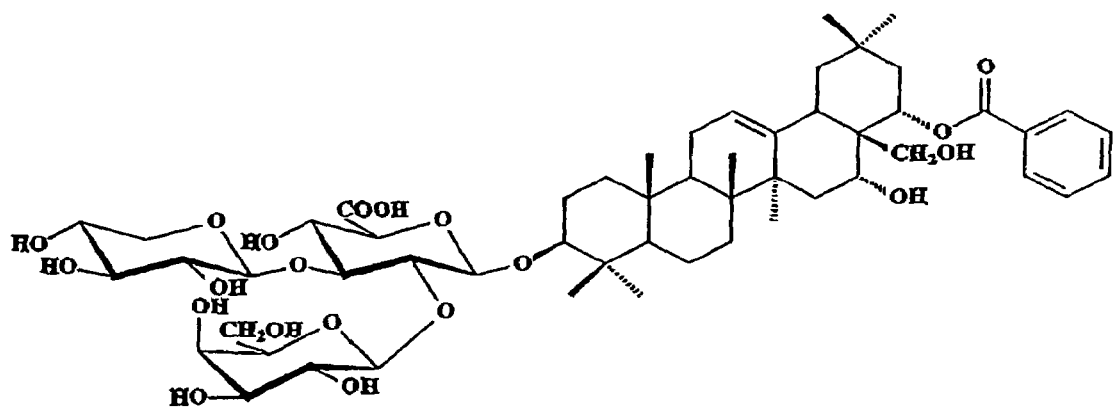
FIG 58 - Compound F70.3.3.2.2b
*(3-O-ß-D-xylopyranosyl(1→3)-[ß-D-galactopyranosyl(1→2)]-ß-D-glucuronopyranosyl-22-O-benzoyl barringtogenol C)*

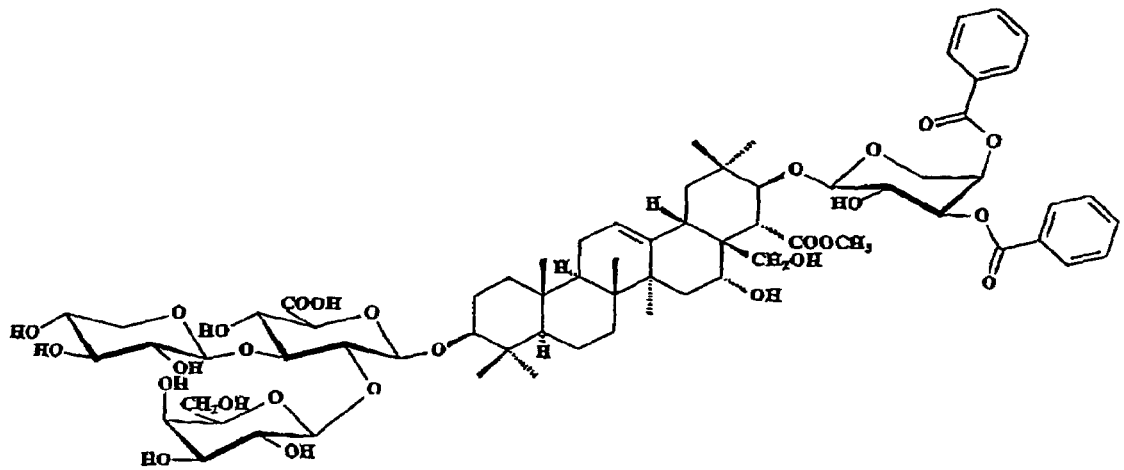
FIG 59 - Compound F70.2.6.2
(3-O-ß-D-xylopyranosyl(1→3)-[ß-D-galactopyranosyl(1→2)]-ß-D-glucuronopyranosyl-21-O-[3,4-dibenzoyl-ɤ-L-arabinopyranosyl]-22-O-acetyl barringtogenol C)
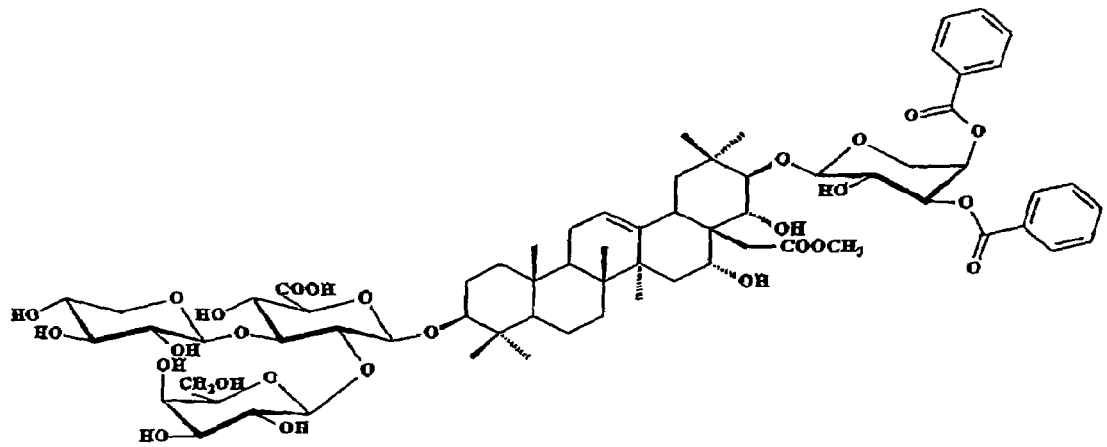
FIG 60 - Compound F70.3.4.5
(3-O-ß-D-xylopyranosyl(1→3)-[ß-D-galactopyranosyl(1→2)]-ß-D-glucuronopyranosyl-21-O-[3,4-dibenzoyl-α-L-arabinopyranosyl]-28-O-acetyl barringtogenol C)

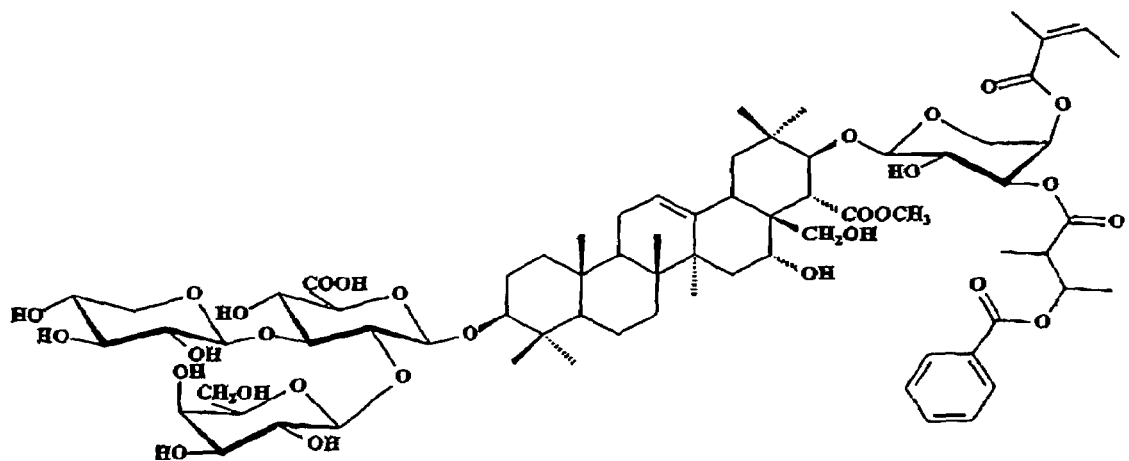
FIG 61 - Compound F70.3.5a
(3-O-ß-D-xylopyranosyl(1→3)-[ß-D-galactopyranosyl(1→2)]-ß-D-glucuronopyranosyl-21-O-[3-(3-benzoyl-2-methylbutyryl)-4-tigloyl-α-L-arabinopyranosyl]-22-O-acetyl barringtogenol C)
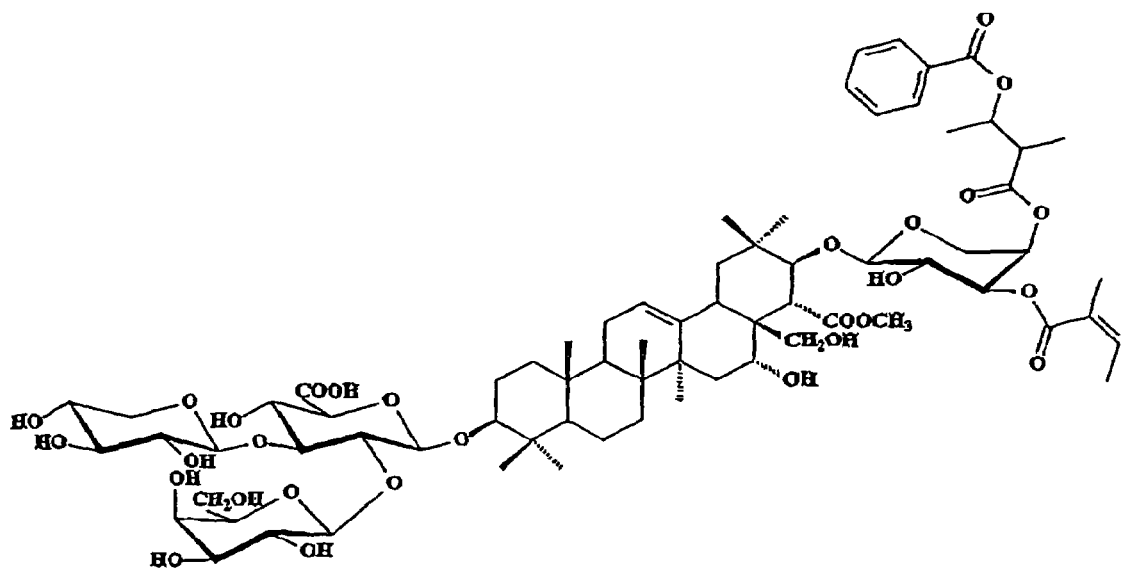
FIG 62 - Compound F70.3.5b
(3-O-ß-D-xylopyranosyl(1→3)-[ß-D-galactopyranosyl(1→2)]-ß-D-glucuronopyranosyl-21-O-[3-tigloyl-4-(3-benzoyl-2-methylbutyryl)-α-L-arabinopyranosyl]-22-O-acetyl barringtogenol C)

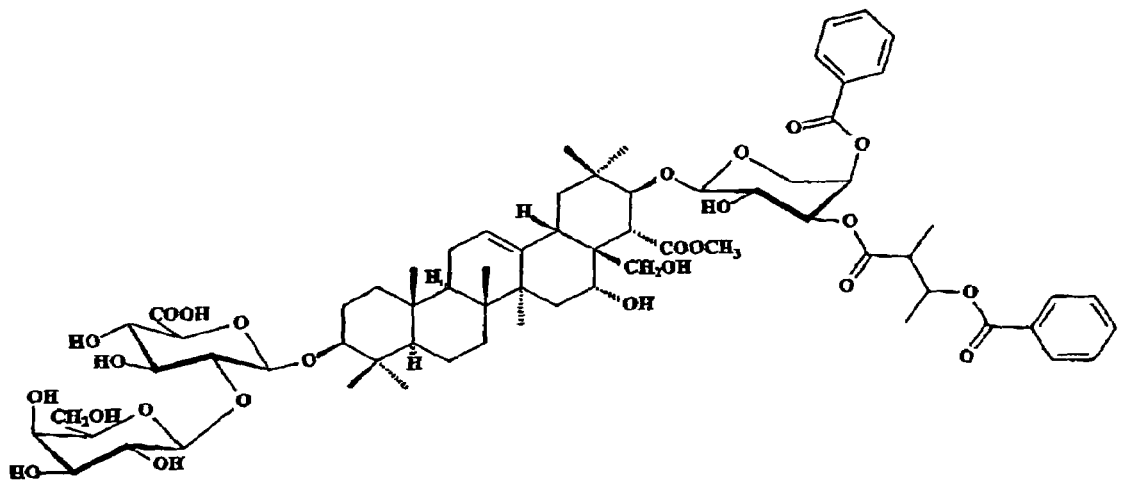
FIG 63 - Compound F70.3.7.2
(3-O-ß-D-galactopyranosyl(1→2)-ß-D-glucuronopyranosyl-21-O-[3-(3-β-benzoyl-2-methylbutyryl)-4-benzoyl-α-L-arabinopyranosyl]-22-O-acetyl barringtogenol C)
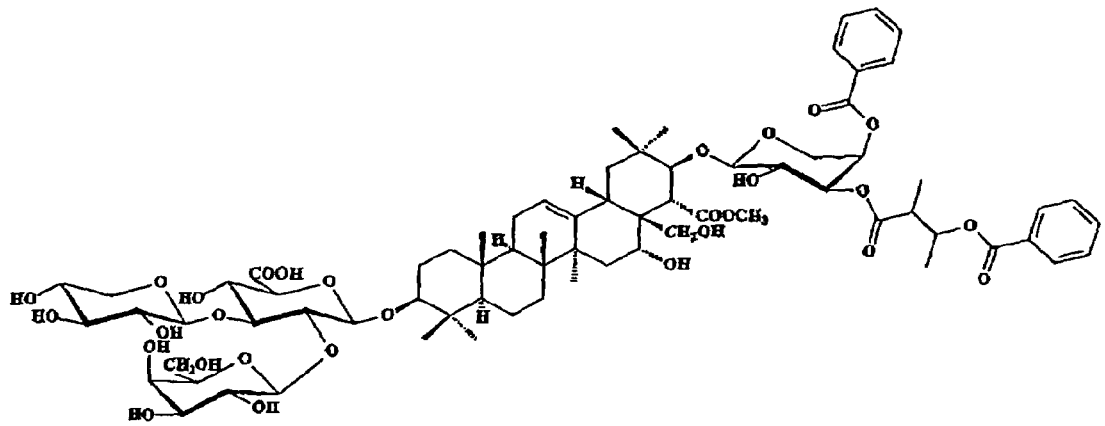
FIG 64 - Compound F80.4.5.2/F80.5.2
(3-O-ß-D-xylopyranosyl(1→3)-[ß-D-galactopyranosyl(1→2)]-ß-D-glucuronopyranosyl-21-O-[3-(3-benzoyl-2-methylbutyryl)-4-benzoyl-α-L-arabinopyranosyl]-28-O-acetyl barringtogenol C)

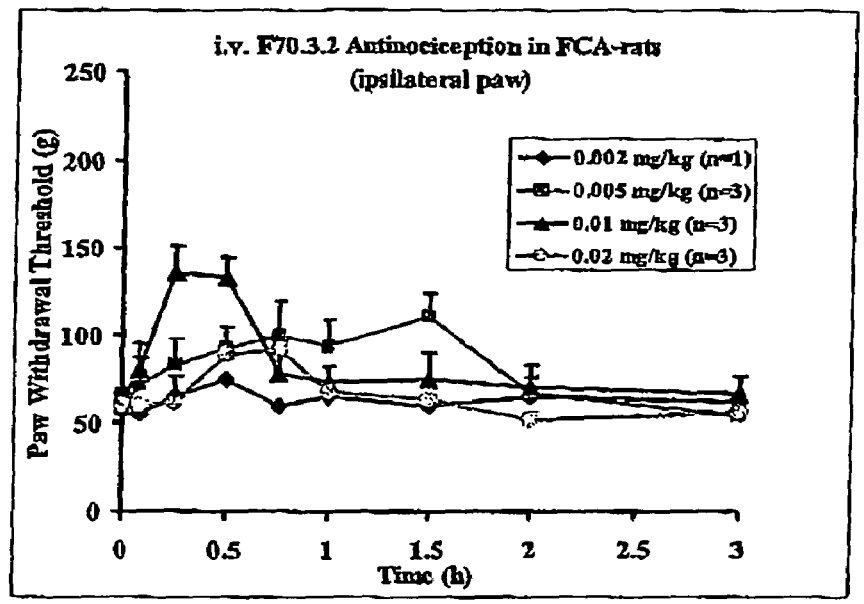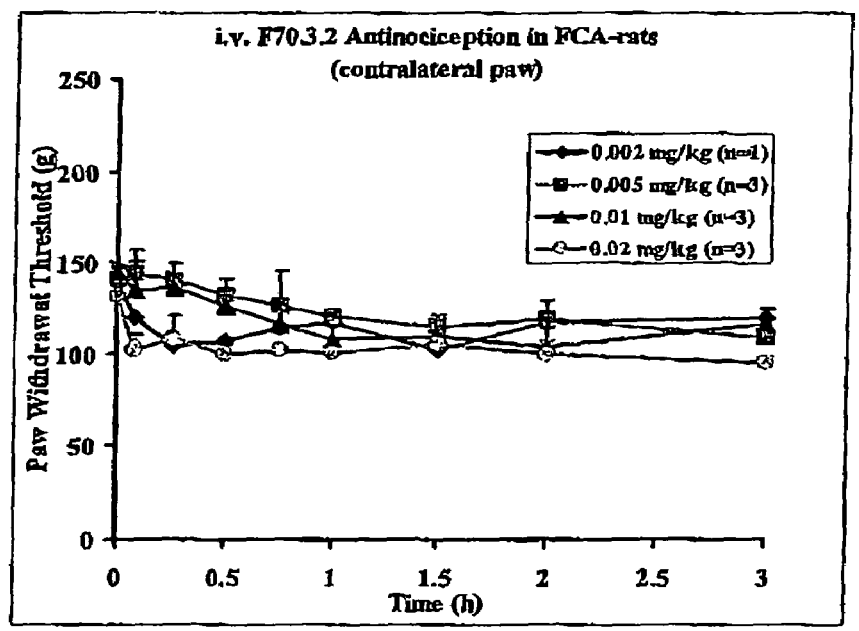
FIG. 65   is a graph of the mean (± SEM) paw withdrawal threshold versus time curves for (A) ipsilateral (inflamed) and (B) contralateral (non-inflamed) hindpaws of FCA-rats.

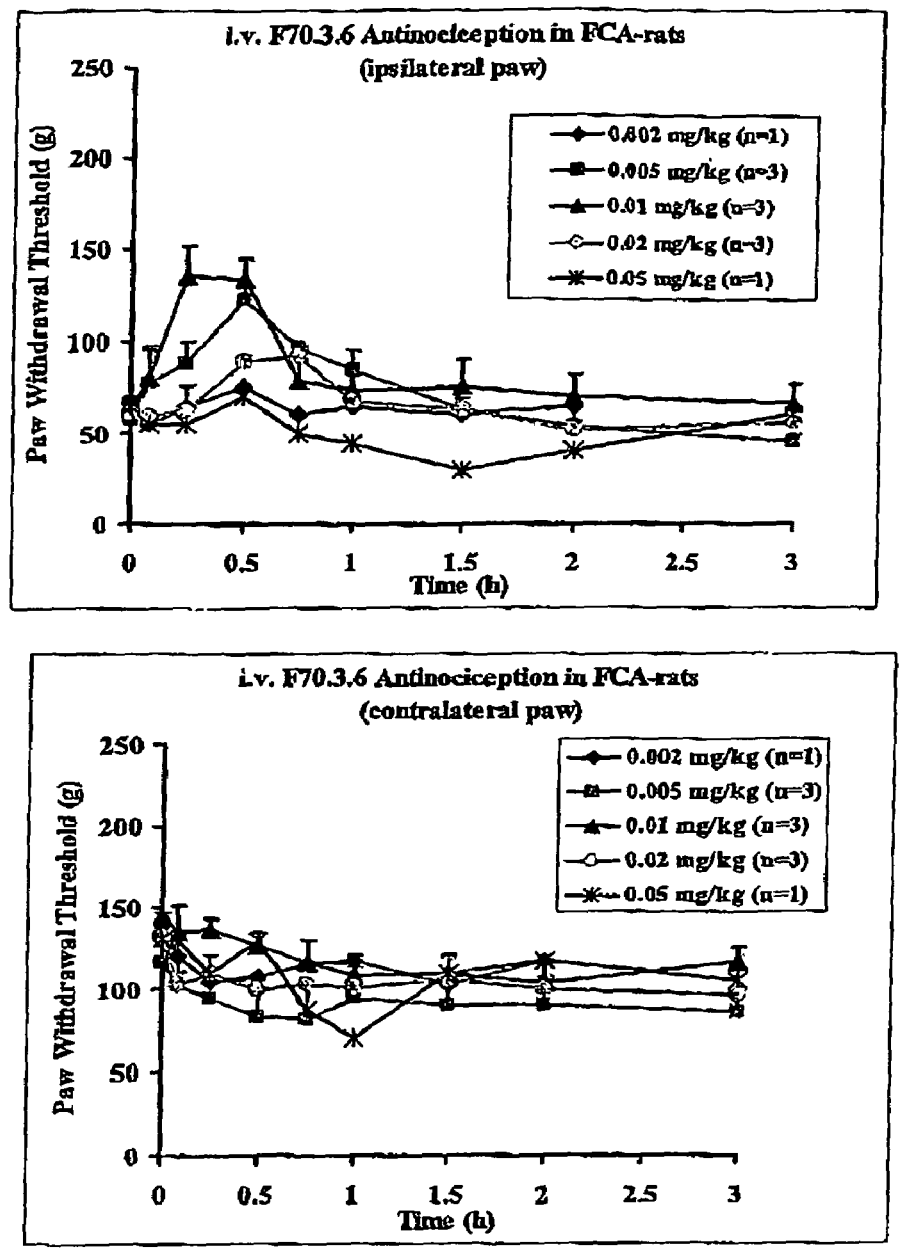
FIG. 66 is a graph of the mean (± SEM) paw withdrawal threshold versus time curves for the (A) ipsilateral (inflamed) and the (B) contralateral (non-inflamed) hindpaws of FCA-rats.

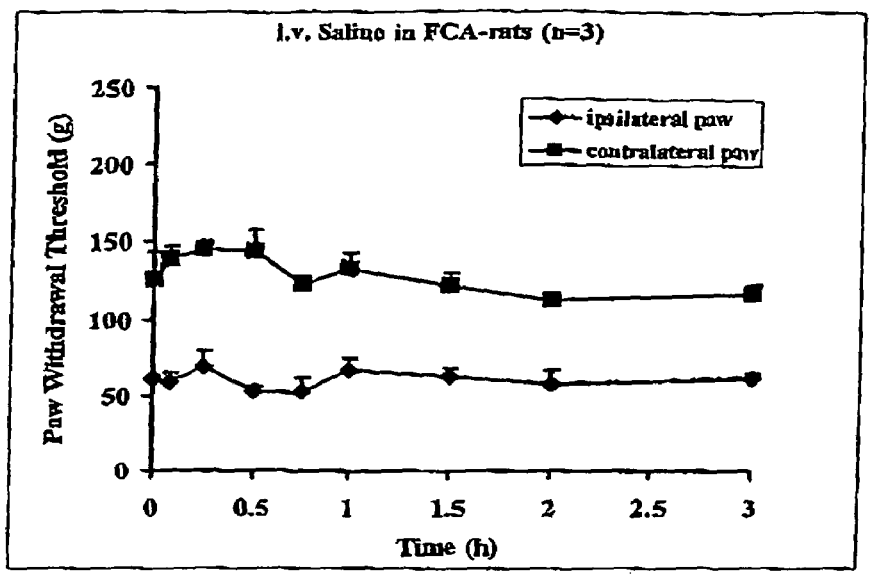

FIG. 67: is the mean (± SEM) paw withdrawal threshold versus time curve for the Ipsilateral (inflamed) and the contralateral (non-inflamed) hindpaw in FCA-treated adult male Sprague-Dawley rats (n = 3) that received a single i.v. bolus of saline.

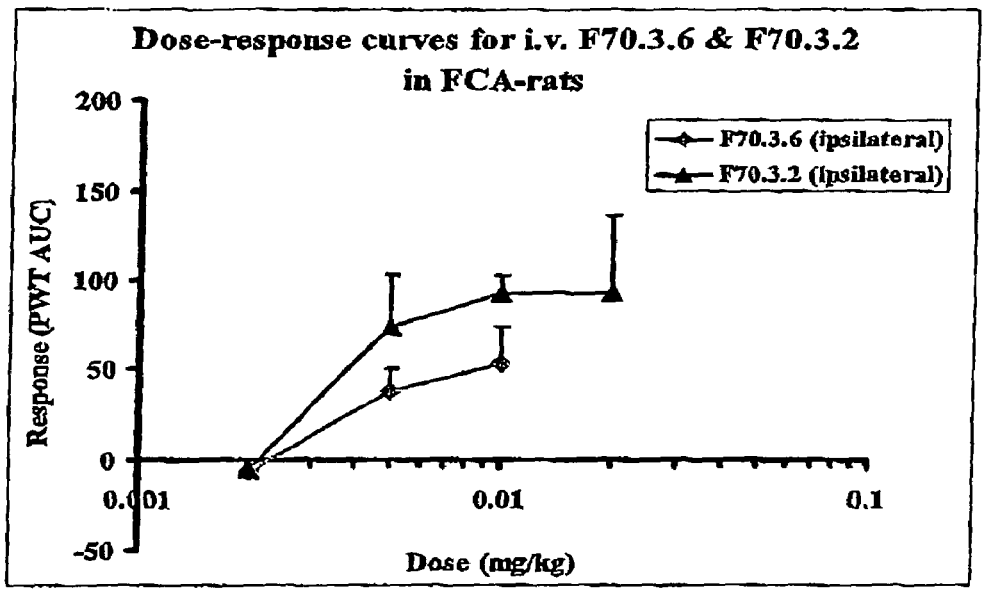

FIG. 68: Mean (± SEM) dose-response curves for the antinociceptive effects of i.v. bolus doses of F70.3.2 and F70.3.6 in the ipsilateral hindpaws of FCA-rats.

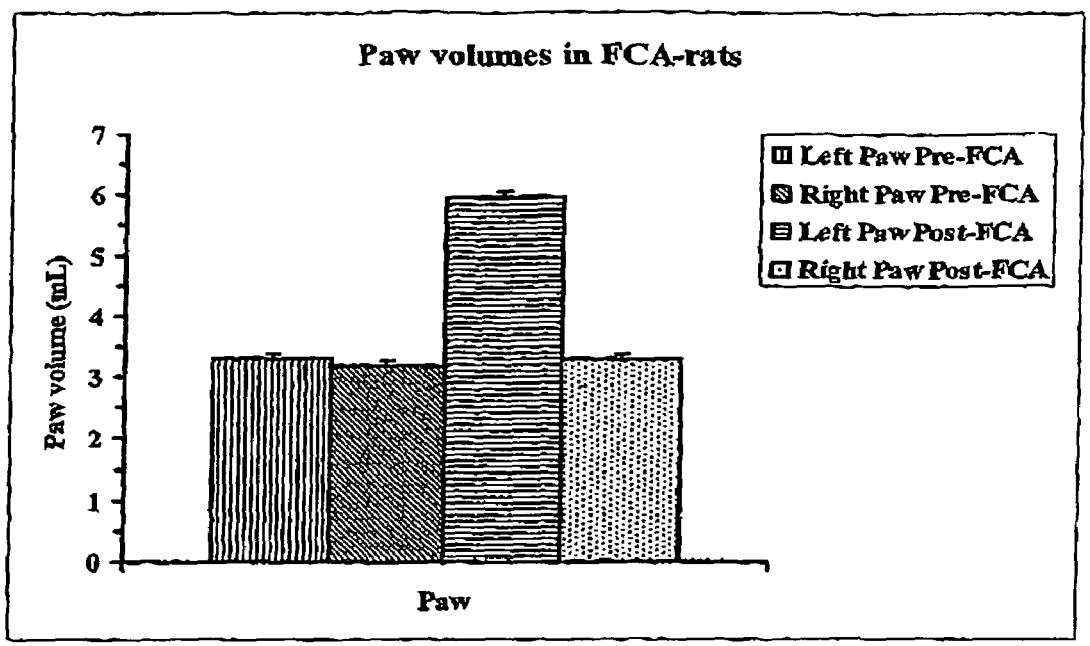
FIG. 69    Is a graph of the paw volume pre and post FCA treatment.

ANALGESIC COMPOUNDS, EXTRACTS CONTAINING SAME AND METHODS OF PREPARATION

RELATED APPLICATIONS

This is a National Stage of International Application Number PCT/AU04/01660, filed Nov. 26, 2004, which claims priority to foreign application AU2003906558, filed Nov. 27, 2003.

FIELD OF THE INVENTION

This invention relates to novel compounds having analgesic properties and extracts containing same. Such compounds are obtained from plants of the *Barringtonia* species.

BACKGROUND OF THE INVENTION

*Barringtonia* comprise the largest genus of plants within the family Lecythidaceae and are widely distributed in the tropical regions of Asia, Malaysia and the Pacific. [1]

*Barringtonia* are trees or shrubs ranging in size from 2 m to in excess of 25 m. Four species are known to occur in Northern Australia [2], three of which, *B. racemosa* [(L.) Spreng], *B. calyptrate* [(Mietrs) R. Br. ex Bailey] and *B. asiatica* [(L.) Kurtz] are known only from north Queensland. The fourth Australian species, *B. acutangula* [(L.) Gaertn], has wider distribution, being found across Northern Australia from North Queensland to North Western Australia. *Barringtonia acutangula* has been further divided into two subspecies, *B. acutangula* ssp. *acutangula* and *B. acutangula* ssp. *spicata* [1]. The latter of these is found throughout the *Barringtonia* distribution area whereas the former is restricted to Northern Australia.

Throughout their range many *Barringtonia* species have been used in variety of ways by local people. One common use of *Barringtonia* species is as a fish poison [2-5]. Several species have been reported as fish poisons including *B. acutangula* [2-4, 6-11], *B. speciosa* [5], *B. racemosa* [2, 3, 10-12], *B. asiatrica* [2, 3, 5, 10, 11] and *B. calyptrate* [10]. Although the fruit and bark of the tree is often used as a fish poison [2, 3, 5-12], several other plant organs, including leaves [8, 11], roots [4, 8, 9, 11], seeds [2, 9, 10, 12] and wood [12], have also been used. The leaves, fruit and seeds of several species are known to be edible [3, 9, 12-15].

Several other properties and uses of *Barringtonia* species have been reported. These include the use of *B. racemosa* as a tanning agent, due to the presence of tannins, [3, 12, 16] and as an insecticide reportedly to be approximately half as potent as nicotine [12,16, 17]. The fruit of *Barringtonia* has been used to poison wild pig [12]. In addition the seed of *B. racemosa* and the fruit of *B. asiatica* has been used for suicide and administration with ". . . homicidal intent . . . " [11, 12], coconut milk being an antidote. These toxic properties may be due to the presence of HCN which has been demonstrated in high concentrations in the kernel of *B. asiatica* [11].

Many of the *Barringtonia* species have found extensive use as traditional medicines and the fruit of *B. acutangula* has been called "Nurse fruit" [6]. All parts of the plant have been used and applications have been both internal and external. Preparation of applications may involve drying and powdering, extraction with hot or cold water, heating or juicing [3, 11, 12, 16, 18]. External applications tend to focus, as expected, on skin disease. Ailments such as general wounds, rheumatism, eczema, ulcers, scabies, tinea, ringworm, itches, inflammation and even leprosy have been treated with *Barringtonia* species [3, 11, 12, 16, 18]. Seeds in powered form have been used as a snuff to relieve headache whereas heated seeds are aromatic and have been used to assist in colic and parturition [3]. External applications to assist ophthalmia, chest cold and pain, asthma, fever, colic, flatulence, non-venereal stricture, sore throat and stomach ache have also been reported [3, 6, 11, 12, 16, 18].

Common internal used of *Barringtonia* are for the relief of diarrhoea, dysentery and stomach ache, as an emetic, expectorate and laxative [3, 6, 8-12, 16, 18, 19]. Preparations of some species are taken as a bitter tonic [3, 8, 9, 11, 18, 19] and the seed of *B. racemosa* is taken as a vermifuge [18].

As fish poisons, *Barringtonia* species, in particular *B. actungula* [4], were used extensively in Australia, however it seems that little use was made of *Barringtonia* species as medicines compared with other regions in which the plants are located. In Australian, *Barringtonia* extracts have been used for skin complaints such as wounds, boils and chickenpox (*B. racemosa* and *B. acutangula*), for chest pain and fever (*B. calyprata*), in ophthalmia, colic, parturition and to induce vomiting (*B. acutangula*) [10, 11, 16, 18]. More detailed accounts of the uses of *Barringtonia* sp. can be found in the literature (eg [3, 12, 18]).

In view of the wide traditional application of *Barringtonia* species as medicinal plants, it is surprising that the chemical nature of the bioactive constituents has attracted little attention.

The presence of saponin-like glycosides in *B. insignis, B. vriesei* and *B. racemosa* was demonstrated as early as 1898 (reported in [6]). Subsequently, in 1901, a saponin was isolated from *B. speciosa* which yielded, on hydrolysis, glucose and barringtogenin (reported in [20], although [6] reports the species as *B. spinosa*). The same author also reported the presence of a second sapogenin, namely barringtogenitin. Nozoe isolated $A_1$-barrinin and $A_1$-barrigenin from the seeds of *B. asiatica* and subsequently reported that the saponin of $A_1$-barrinin contained gluconic acid, d-glucose, d-galactose and a methyl pentose [21, 22]. Alkaline hydrolysis of $A_1$-barrigenin gave tiglic acid and a new aglycone, $A_1$-barrigenol [23]. Acetylation of $A_1$-barrigenin also led to the isolation of a second aglycone, $A_2$-barrigenol [23].

The presence of high concentrations of saponins was reported from the seeds, leaves and bark of *B. acutangula* and *B. racemosa* and three sapogenins were identified [20]. Much of the ensuing work aimed to isolate and characterise the nature of these saponins.

The structure of $A_1$-barrigenol as first assigned by Cole et al. in 1955 is shown in FIG. 1.

During the 1950's, there was a growing interest in saponins and sapogenins as evidenced by the number of publications in which, using mainly degradative techniques, structures were assigned and revised. The first sapogenins isolated from a *Barringtonia* species after $A_1$- and $A_2$-barrigenol were barringtogenol and barringtogenic acid which were isolated from the fruit of *B. racemosa* [25] and which structures are shown in FIG. 2.

*Barringtonia acutangula* continued to be a source of novel saponins and sapogenins. Again from the fruit of this species, a series of compounds, barringtogenol B, C, D, and E, were isolated and their structures explored [8, 26-34].

Barringtogenol C was isolated from *B. acutangula* fruits and the structure assigned by chemical techniques as previously described (FIG. 4) (eg [8, 26, 27, 31-34]).

Barringtogenol D, again isolated from *B. acutangula* fruit, was described by Barua et al [26] and a structure proposed by Chakraborti and Barua [29,30] (FIG. 5).

Barringtogenol E was isolated from the branch wood of *B. acutangula* and a structure was assigned using mass spectral and chemical information (FIG. 6) [8, 28]. It was noted that barringtogenol E was perhaps the first example of a triterpene benzoate isolated from nature [8, 28].

Other compounds isolated from *B. acutangula* include tanginol [8, 35, 36] as shown in FIG. 7 and barrinic acid shown in FIG. 8.

Several compounds have been isolated, again from *B. acutangula*, and their structures assigned in part using NMR. These include barrigenic acid, the 19β-isomer of barrinic acid (fruit) [36] and acutangulic and tangulic acids (leaves) (FIG. 9) [3840].

It was not until 1991 [41] that the structure of an intact saponin from *B. acutangula* was published. Spectral and chemical data led to the structure being assigned as 2α,3β,19α-trihydroxy-olean-12-ene-dioic acid 28-O-β-D-glucopyranoside (FIG. 10) [41].

Shortly after the publication of this structure the same group published the complete structures of three more saponins from the seeds of B. acutangula, barringtosides A, B and C (FIG. 11) [42].

Although this *Barringtonia* species has been used as medicinal plants for a wide variety of ailments, no information concerning the biological activity of any of the isolated triterpenes can be located. However, it is known that triterpenes have some anti-inflammatory activity (eg [43, 44]). The astringent properties of the bark of *Barringtonia* have been attributed to the presence of tannins [16, 18] which are also known to possess anti-microbial properties (eg [45]). The general use of *Barringtonia* species as preparation for skin sores, wounds and other skin complaints may be due to the presence of these tannins. Many of the reported effects induced by preparations from these trees can be accounted for by the activity of steroids (eg anti-inflammatory, anti-asthmatic, anti-rheumatic etc) and the presence of the β- and (-sitosterol and stigmasterol-3β-O-D-glucoside in extracts from *Barringtonia* species may explain some of these activities. It is also well known that saponins exhibit a wide range of biological activities, many of which could explain the observed medicinal properties outlined earlier (eg [46, 47]).

As is evident from the preceding discussion, the dominant group of compounds found in *Barringtonia* thus far studies are saponins. Saponins are an important class of secondary metabolites that are widespread in plants and lower marine organisms. It has been reported that approximately 79% of all plants surveyed contain saponins [48]. It has also been proposed that saponins are produced as defensive agents by the plant [48]. Increasing numbers of saponins are being isolated from lower marine organisms, but so far have been isolated from the phylum Echinodermata, in particular sea cucumbers (Holothuroidea) and starfish (Asteroidea) [46].

Saponins consist of three main components, an aglycone (genin or sapogenin), such as a triterpene, a steroid or a steroidal alkaloid, one or more sugar chains, commonly D-glucose, D-galactose, D-glucuronic acid, D-galacturonic acid, L-rhamnose, L-arabinose, D-xylose and D-fucose and sometimes acids, such as angelic and tiglic acids [46,47, 49]. Saponins are further classified as mono-, bi- or tri-desmosides according to the number of sugar chains which are attached to the aglycone [47].

The haemolytic, molluscidal and piscicidal activities of saponins are well characterised and have even been used as assay techniques in bio-guided fractionations of plant and animal extracts (eg [47, 48, 50, 51]). However haemolytic activity varies greatly or may be absent altogether and molluscicidal activity is somewhat dependent on the structure of the saponin [46, 47]. As expected there are many publications on the biological and pharmacological properties of saponins, examples of which can be seen in [46, 47].

Analgesic activity has been demonstrated in a small number of saponins. The following is an example of some of the saponins found to have analgesic effects. Using the acetic acid writhing test it was shown that barbatoside A ($ED_{50}$ 95 mg/kg) and B ($ED_{50}$ 50 mg/kg), glycosides of quaillic acid from *Dianthus barbatus*, were more active than acetylsalic acid ($ED_{50}$ 125 mg/kg) [52]. An intraperitoneal (ip) injection of a saponin preparation from *Dolichos falcatus* at 5 mg/kg was shown to produce marked analgesic effect to pain induced by exposure of 55° C. in mice [53]. An extract of *Platycodon grandiflorum* also induced analgesia in mice when injected subcutaneous (sc) at a dose of 2 g/kg [54]. One of the active ingredients is stated as being platicodin and the dose received by the mice was equivalent to 160 mg/kg. The effects were comparable to 100-200 mg/kg aspirin. Injection (ip, 100-250 mg/kg) of the total saponin preparation from *Panax notoginseng* was found to act faster but for shorter durations than morphine and I-tetrahydropalmatine and was comparable to aminopyrine (150 mg/kg) [55]. It was also noted that the saponin preparation induced a sedative effect, decreased the $ED_{50}$ of pentobarbital in sleep induction, prolonged thiopental induced sleep and showed synergistic effects with chlorpromazine in CNS inhibition [55]. A number of dianosides were isolated and characterised from *Dianthus superbus* ver. *Iongicalycinus* [56-58]. Dianosides A and B were found to significantly inhibit acetic acid induced writhing at 10 and 30 mg/kg (sc) with dianoside B the more potent [56]. In a detailed examination of the pharmacological effects of glycosidal fraction obtained from *Maesa chisa* var. *augustifolia*, Gomes et al [59] demonstrated, among other things, analgesia in the writhing test in mice. A 33% inhibition was observed in p-phenylquinonone induced writhing in contrast to a 52% inhibition observed in acetic acid induced writhing. By comparison, aspirin inhibited p-phenylquinone induced writhing by 85% and acetic acid induced writhing by 80%. The absence of straubtail phenomena and lack of activity in both the hot plate and the tail flick tests suggests that the analgesia produced by the glycoside fraction was different to that produced by narcotics.

SUMMARY OF THE INVENTION

One aspect of the invention, and by no means the broadest form, provides for novel compounds of the formula (I)

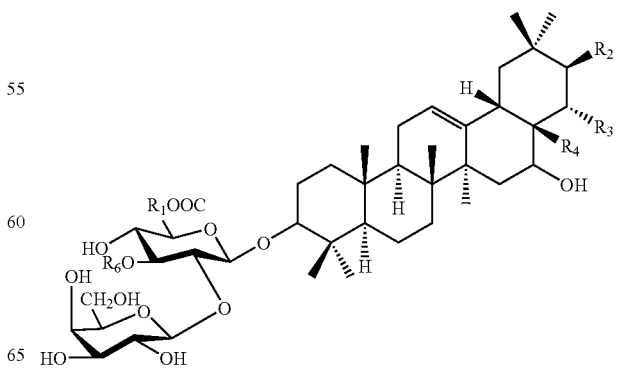

wherein:

$R_2$ is selected from hydrogen, hydroxyl, O-alkyl, O-alkenyl, O-benzoyl, O-alkanoyl, O-alkenoyl, O-aryl, O-heterocyclic, O-heteroaryl or

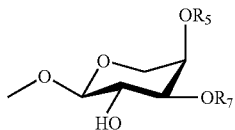

wherein $R_5$ and $R_7$ are independently be selected from hydrogen, alkanoyl, alkenoyl, benzoyl or benzoyl alkyl substituted alkanoyl;

$R_3$ is selected from hydroxyl, O-alkanoyl, O-alkenoyl, O-benzoyl, O-alkyl, O-alkenyl, O-aryl, O-heterocyclic or O-heteroaryl;

$R_4$ is selected from —$CH_2OH$, COOH, $CH_2OCOCH_3$, COO alkyl, COO aryl, $CH_2COO$ alkyl, COO-heterocyclic, COO-heteroaryl, $CH_2$—O aryl, $CH_2O$ heterocyclic or $CH_2O$ heteroaryl;

$R_6$ is selected from hydrogen or

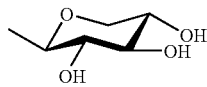

$R_1$ is selected from hydrogen or alkyl; or pharmaceutically acceptable salts thereof, with the provisos that when:

$R_2$ is OH, $R_3$ is OH, $R_4$ is $CH_2OH$, and $R_6$ is xylopyranosyl, $R_1$ is not H;

$R_4$ is $CH_2OH$ and $R_3$ is O-alkanoyl $R_2$ is not O-acetyl;

$R_4$ is $CH_2OH$ and $R_2$ is O-alkenoyl $R_3$ is not hydroxyl; and $R_4$ is $CH_2OH$ and $R_3$ is hydroxyl then $R_2$ is not hydroxyl.

The term "alkyl" refers to linear, branched, cyclic and bicyclic structures and combinations thereof, having 1 to 18 carbon atoms. Non-limiting examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, cyclopropyl, cyclobutyl, cyclopentyl, cyclohexyl and the like. More preferably alkyl is selected from methyl, ethyl, propyl, isopropyl, butyl, s- and t-butyl, pentyl, and hexyl.

The term "alkenyl" refers to unsaturated linear or branched structures and combinations thereof, having 1 to 7 carbon atoms. Non-limiting examples of alkenyl groups include, ethenyl, propenyl, isopropenyl, butenyl, s- and t-butenyl, pentenyl, hexenyl.

"Alkanoyl" means alkanoyl groups of a straight or branched configuration having 1-8 carbon atoms. Preferably alkanoyl is selected from acetyl, propionoyl, butyryl, isobutyryl, pentanoyl and hexanoyl. More preferable alkanoyl is selected from acetyl, propionoyl, butyryl, and isobutyryl.

"Alkenoyl" means alkenylcarbonyl in which alkenyl is as defined above. Preferably alkenoyl is selected from pentenoyl, hexenoyl or heptenoyl. More preferably alkenoyl is selected from pentenoyl (tigloyl) or hexenoyl (angeloyl).

The term "benzoyl alkyl substituted alkanoyl" is used to refer to straight or branched C1-C6 alkanoyl substituted with at least one benzoyl and at least one alkyl, wherein the benzoyl is attached to an straight or branched C1-6 alkyl. Preferably a benzoyl alkyl substituted alkanoyl is benzoyl methyl isobutanoyl.

"Heterocyclic" refers to a non-aromatic ring having 1 to 4 heteroatoms said ring being isolated or fused to a second ring selected from 3- to 7-membered alicyclic ring containing 0 to 4 heteroatoms, aryl and heteroaryl, wherein said heteroatoms are independently selected from O, N and S. Non-limiting examples of heterocyclic include pyrrolidinyl, piperidinyl, piperazinyl, morpholinyl, tetrahydrofuranyl, imidazolinyl, thiomorpholinyl, and the like.

"Aryl" means a 6-14 membered carbocyclic aromatic ring system comprising 1-3 benzene rings. If two or more aromatic rings are present, then the rings are fused together, so that adjacent rings share a common bond. Examples include phenyl and naphthyl. The aryl group may be substituted with one or more substituents independently selected from halogen, alkyl or alkoxy.

The term "heteroaryl" as used herein represents a 5-10 membered aromatic ring system containing a single ring having 1-4 heteroatoms, selected from O, S and N. Heteroaryl includes, but is not limited to, furanyl, diazinyl, imidazolyl, isooxazolyl, isothiazolyl, pyridyl, pyrrolyl, thiazolyl, triazinyl and the like.

Preferably $R_2$ is hydrogen, O-benzoyl, O-tigloyl, or

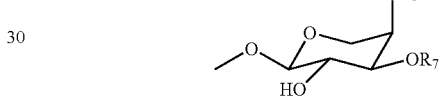

wherein $R_5$ and $R_7$ are selected from hydrogen, tigloyl, benzoyl, or benzoyl alkyl substituted alkanoyl.

Preferably $R_3$ is selected from hydroxyl, O-acetyl, O-benzoyl, O-isobutyryl or O-tigloyl.

Preferably $R_4$ is selected from —$CH_2OH$, O-acetyl or hydroxyl. Preferably the compound of formula (I) is selected from;

a. 3-O-β-D-xylopyranosyl(1→3)-[β-D-galactopyranosyl (1→2)]-β-D-glucuronopyranosyl-21-O-[3-(3-benzoyl-2-methylbutanoyl)-4-benzoyl-α-L-arabinopyranosyl]-22-O-acetyl barringtogenol C;

b. 3-O-β-D-xylopyranosyl(1→3)-[β-D-galactopyranosyl (1→2)]-β-D-glucuronopyranosyl-21-O-benzoyl barringtogenol C;

c. 3-O-β-D-xylopyranosyl(1→3)-[β-D-galactopyranosyl (1→2)]-β-D-glucuronopyranosyl-21-O-benzoyl-28-O-acetyl barringtogenol C;

d. 3-O-β-D-xylopyranosyl(1→3)-[β-D-galactopyranosyl (1→2)]-β-D-glucuronopyranosyl-21-O-benzoyl-22-O-isobutyryl barringtogenol C;

e. 3-O-β-D-xylopyranosyl(1→3)-[β-D-galactopyranosyl (1→2)]-β-D-methylglucuronopyranosyl-21,22-O-dibenzoyl barringtogenol C;

f. 3-O-β-D-xylopyranosyl(1→3)-[β-D-galactopyranosyl (1→2)]-β-D-glucuronopyranosyl-21,22-O-dibenzoyl barringtogenol C;

g. 3-O-β-D-xylopyranosyl(1→3)-[β-D-galactopyranosyl (1→2)]-β-D-methylglucuronopyranosyl-21-O-benzoyl-22-O-tigloyl barringtogenol C;

h. 3-O-β-D-xylopyranosyl(1→3)-[β-D-galactopyranosyl (1→2)]-β-D-glucuronopyranosyl-21-O-benzoyl-22-O-tigloyl barringtogenol C;

i. 3-O-β-D-xylopyranosyl(1→3)-[β-D-galactopyranosyl(1→2)]-β-D-methylglucuronopyranosyl-21,22-O-tigloyl barringtogenol C;
j. 3-O-β-D-xylopyranosyl(1→3>)-[β-D-galactopyranosyl(1→2)]-D-glucuronopyranosyl-21,22-O-tigloyl barringtogenol C;
k. 3-O-β-D-xylopyranosyl(1→3)-[β-D-galactopyranosyl(1→2)]-β-D-glucuronopyranosyl-22-O-benzoyl barringtogenol C;
l. 3-O-β-D-xylopyranosyl(1→3)-[β-D-galactopyranosyl(1→2)]-β-D-glucuronopyranosyl-21-O-[3,4-dibenzoyl-α-L-arabinopyranosyl]-22-O-acetyl barringtogenol C;
m. 3-O-β-D-xylopyranosyl(1→3)-[β-D-galactopyranosyl(1→2)]-β-D-glucuronopyranosyl-21-O-[3,4dibenzoyl-α-L-arabinopyranosyl]-28-O-acetyl barringtogenol C;
n. 3-O-β-D-xylopyranosyl(1→3)[β-D-galactopyranosyl(1→2)]-β-D-glucuronopyranosyl-21-O-[3-(3-benzoyl-2-methylbutyryl)-4-tigloyl-α-L-arabinopyranosyl]-22-O-acetyl barringtogenol C;
o. 3-O-β-D-xylopyranosyl(1→3)-[β-D-galactopyranosyl(1→2)]-βD-glucuronopyranosyl-21-O-[3-tigloyl(3-benzoyl-2-methylbutyryl)-α-L-arabinopyranosyl]-22-O-acetyl barringtogenol C;
p. 3-O-β-D-galactopyranosyl(1→2)-β-D-glucuronopyranosyl-21-O-[3-(3-benzoyl-2-methylbutyryl)-4-benzoyl-α-L-arabinopyranosyl]-22-O-acetyl barringtogenol C; or
q. 3O-β-D-xylopyranosyl(1→3)-[β-D-galactopyranosyl(1→2)]-β-D-glucuronopyranosyl-21-O-[3-(3benzoyl-2-methylbutyryl)-4-benzoyl-α-L-arabinopyranosyl]-28-O-acetyl barringtogenol C.

The term "pharmaceutically acceptable salts: as used herein refers to salts which are toxicologically safe for systemic administration. The pharmaceutically acceptable salts may be selected from the group including alkali and alkali earth, ammonium, aluminium, iron, amine, glucosamine, choline, sulphate, bisulphate, nitrate, citrate, tartrate, bitarate, phosphate, carbonate, bicarbonate, malate, maleate, napsylate, fumarate, succinate, acetate, terephthalate, pamoate, pectinate and s-methyl methionine salts piperazine and the like.

Another aspect of the invention resides in a composition containing one or more compounds of formula (I) when extracted from plants or parts of plants of the genus *Barringtonia*, preferably the species *Barringtonia acutangula*. The parts of plants include fruit, seed, bark, leaf, flower, and wood. Preferably the part of plants is selected from bark, flower and leaf. More preferably the parts of plants is bark.

Another aspect of the invention resides in a pharmaceutical composition for treatment and/or control of pain comprising an effective amount of one or more compounds of formula (I) and a pharmaceutically acceptable carrier.

Dosage forms include tablets, dispersions, suspensions, injections, solutions, syrups, troches, capsules, suppositories, aerosols, transdermal patches and the like. These dosage forms may also include injecting or implanting devices designed specifically for, or modified to, controlled release of the pharmaceutical composition. Controlled release of the therapeutic agent may be effected by coating the same, for example, with hydrophobic polymers including acrylic resins, waxes, higher aliphatic alcohols, polyactic and polyglycolic acids and certain cellulose derivates such as hydroxypropylmethyl cellulose. In addition, the controlled release may be affected by using other polymer matrices, liposomes and/or microspheres.

Pharmaceutically acceptable carriers for systemic administration may also be incorporated into the compositions of this invention.

Suitably, the pharmaceutical composition comprises a pharmaceutically-acceptable excipient. By "pharmaceutically-acceptable excipient" is meant a solid or liquid filler, diluent or encapsulating substance that may be safely used in systemic administration. Depending upon the particular route of administration, a variety of carriers, well known in the art may be used. These carriers or excipients may be selected from a group including sugars, starches, cellulose and its derivates, malt, gelatine, talc, calcium sulphate, vegetable oils, synthetic oils, polyols, alginic acid, phosphate buffered solutions, emulsifiers, isotonic saline, and pyrogen-free water.

Any suitable route of administration may be employed for providing a patient with the pharmaceutical composition of the invention. For example, oral, rectal, parenteral, sublingual, buccal, intravenous, intraarticular, intra-muscular, intra-dermal, subcutaneous, inhalational, intraocular, intraperitoneal, intracerebroventricular, transdermal and the like may be employed.

Pharmaceutical compositions of the present invention suitable for administration may be presented in discrete units such as vials, capsules, sachets or tablets each containing a predetermined amount of one or more pharmaceutically active compounds of the invention, as a powder or granules or as a solution or a suspension in an aqueous liquid, a non-aqueous liquid, an oil-in water emulsion or a water in oil emulsion. Such compositions may be prepared by any of the method of pharmacy but all methods include the step of bringing into association one or more pharmaceutically active compounds of the invention with the carrier which constitutes one ore more necessary ingredients. In general, the compositions are prepared by uniformly and intimately admixing the agents of the invention with liquid carriers or finely divided solid carriers or both, and then, if necessary, shaping the product in to the desired presentation.

The active compounds of formula (I) and of the composition of this invention are present in an amount sufficient to treat and/or control pain. Suitable dosages of the compounds of formula (I) and the pharmaceutical compositions containing such may be readily determined by those skilled in the art but may be of the order of 0.002 mg/kg to 5.0 mg/kg.

In yet another aspect of the invention, there is provided a method of treating and/or controlling pain, comprising administering to a subject in need of such treatment an analgesically effective amount of one or more compounds according to formula (I).

In yet another aspect of the invention, there is provided the use of one or more of the compounds according to formula (I) in the manufacture of a medicament for the treatment and/or control of pain.

BRIEF DESCRIPTION OF THE DRAWINGS

FIG. 1 shows the structure of A1-barringenol;
FIG. 2 shows the structure of barringtogenic acid and barringtogenol;
FIG. 3 shows (a) initial and (b) revised structures of barringtogenol β;
FIG. 4 shows structure of barringtogenol C;
FIG. 5 shows structure of barringtogenol D;
FIG. 6 shows structure of barringtogenol E;
FIG. 7 shows compounds from *B. acutanaula*;
FIG. 8 shows structure of barrinic acid;
FIG. 9 shows compounds from *B acutanaula* including acutangulic acid, tangulic acid and barringenic acid;
FIG. 10 shows structure of 2a, 3β, 19a tri hydroxy-olean-12-ene dioc acid 28-O-β-D glucopyranoside;

FIG. 11 shows structure of barringtoside A, barringtoside B and barringtoside C;

FIG. 12 shows normal grooming response as control in Formalin assay;

FIG. 13 shows control values in formalin assay ($\bar{x}\pm S.E$; n=2);

FIG. 14 shows dose control curve for morphine [$\bar{x}\pm S.E$; n=6 (min)];

FIG. 15 shows schematic for preparation of crude saponin mixtures;

FIG. 16 shows acid and base hydrolysis scheme for insoluble active portion of water extract;

FIG. 17 shows analgesic activity of flowers and leaves of $B$ $acetangula$ ($\bar{x}\pm S.E$; n=2);

FIG. 18 shows analgesic activity of crude water extract ($\bar{x}\pm S.E$; n=5);

FIG. 19 shows analgesic activity of crude water soluble (n=9) and insoluble (n=4) portions of the water extract ($\bar{x}\pm S.E$);

FIG. 20 shows dose response curves for water extract ($\bar{x}\pm S.E$; n=4);

FIG. 21 shows preparative gel permeation column;

FIG. 22 shows dose response curve for TSK—4a ($\bar{x}\pm S.E$; n=3);

FIG. 23 shows C18 separation of TSK—4a;

FIG. 24 shows C18 preparative separation of TSK—4a;

FIG. 25 shows preparative C18 chromatogram of $H_2O$ extract;

FIG. 26 shows outline of numbering system in regard to various fractions for compound F70.2.5.2;

FIG. 27 shows separation of fraction elating at 70% MeOH (F70);

FIG. 28 shows separation of fraction 70.2 (40% MeCN in 1% TFA);

FIG. 29 shows chromatogram of F.70.2.6;

FIG. 30 shows separation of fraction F.70.2.2 at 254 nm (left) and 233 nm (right);

FIG. 31 shows separation of fraction F70.2.5 at 220 nm (left) and 233 nm (right);

FIG. 32 shows separation of fraction F70.3;

FIG. 33 shows chromatograms of F.70.3.5 and F70.3.7;

FIG. 34 shows analytical separation of fraction F.70.3.4 (predominantly single compound);

FIG. 35 shows separation of F70.4;

FIG. 36 shows separation of F70.4.2;

FIG. 37 shows separation of F70.4.3;

FIG. 38 shows preparative chromatograms showing loss of peaks F.80.2 and F.80.3;

FIG. 39 shows preparative chromatograms of F.80.4;

FIG. 40 shows separation of fraction F.80.6 using a phenyl reverse column;

FIG. 41 shows-TLC plates used in hydrolysis procedure showing standard sugars for isolation and structural elucidation of F.70.3.6;

FIG. 42 shows UV spectrum of F.70.3.6;

FIG. 43 shows FRIR spectrum of F.70.3.6;

FIG. 44 shows $^1$H-NMR for compound F.70.3.6;

FIG. 45 shows $^{13}$C-NMR for compound F.70.3.6;

FIG. 46 shows the complete assignment of structure to compound F.70.3.6;

FIG. 47 shows negative ion HR-ESMS of F.70.3.6;

FIG. 48 shows compound F.70.2.52;

FIG. 49 shows compound F.70.2.3;

FIG. 50 shows compound F.70.3.2;

FIG. 51 shows compound F.70.3.4.2;

FIG. 52 shows compound F.70.4.3.5.2/ F.80.6.7;

FIG. 53 shows compound F.80.6.4/ F.70.4.2.4.2;

FIG. 54 shows compound F.70.4.3.4.2/ F.80.6.6;

FIG. 55 shows compound F.70.4.2.3/ F.80.6.3;

FIG. 56 shows compound F.70.4.3.2.2;

FIG. 57 shows compound F.80.6.2;

FIG. 58 shows compound F.70.3.3.2.2b;

FIG. 59 shows compound F.70.2.6.2;

FIG. 60 shows compound F.70.3.4.5;

FIG. 61 shows compound F.70.3.5a;

FIG. 62 shows compound F. 70.3.5b;

FIG. 63 shows compound F.70.3.7.2;

FIG. 64 shows compound F.80.4.5.2/ F.80.5.2;

FIG. 65 is a graph of the mean (±SEM) paw withdrawal threshold versus time curves for (A) ipsilateral (inflamed) and (B) contralateral (non-inflamed) hindpaws of FCA-rats;

FIG. 66 is a graph of the mean (±SEM) paw withdrawal threshold versus time curves for the (A) ipsilateral (inflamed) and the (B) contralateral (non-inflamed) hindpaws of FCA-rats;

FIG. 67 is the mean (±SEM) paw withdrawal threshold versus time curve for the ipsilateral (inflamed) and the contralateral (non-inflamed) hindpaw in FCA-treated adult male Sprague-Dawley rats (n=3) that received a single i.v. bolus of saline;

FIG. 68 is the mean (±SEM) dose-response curves for the antinociceptive effects of i.v. bolus doses of F70.3.2 and F70.3.6 in the ipsilateral hindpaws of FCA-rats; and FIG. 69 is a graph of paw volume pre and post FCA treatment.

EXPERIMENTAL SECTION

Section A—Pain Assays

The Formalin Assay.

The formalin assay involves the subcutaneous injection of a small amount of formalin into the fore or hind paw of a rat or mouse and the behavioural response to this injection is recorded as a measure of pain response. A modification of this method was described by Dubuisson and Dennis [60] and the behavioural response detailed for both rats and cats. Independently the pain produced was described as being initially intense, sharp, stinging and burning and was given a 3/5 on a standard pain questionnaire. Some 4 to 5 minutes later this intense pain gave way to a steady throbbing ache which gradually disappeared over 30 to 60 minutes leaving a mild tenderness at the injection site [60].

The formalin assay was chosen for the current work for several reasons. Firstly, and most importantly, this assay is often reported in journals such as Pain, which would indicate that ethical considerations have been overcome. It has also been demonstrated that the two distinct phases observed in the assay reflect two distinct phases of nociception. The first phase, early or acute, begins immediately after injection of formalin and lasts some 3-5 minutes. This phase is considered to be the direct chemical stimulation of nociceptors. A period of minimal activity lasting for 10-15 minutes follows this initial phase. Subsequently a second, late or tonic phase, begins and lasts for 20-40 minutes. The response shown in both early and late phases can be reduced using known analgesics, such as morphine, codeine, nefopam and orphendarine [61]. The late phase was affected both by non-steroidal anti-inflammatory compounds, such as indomethacin and naproxen and steroids such as dexamethasone and hydrocortisone (e.g. [61]). Interestingly aspirin and paracetamol were shown to be analgesic in a dose dependent manner in both phases of the formalin test [61].

When performing this assay several points, including formalin concentration, experimental subject and site of injection need to be considered.

The formalin assay was preformed on male mice using morphine, and other compounds of interest, as an analgesic, to test the viability and reliability of the assay as a means of measuring pain response in mice.

Methods and Materials.

Experimental Subjects.

Male Quackenbush mice weighing 25-35 g were used. They were housed in colony cages (400×300×130 mm; Wiretainers) with ad libitum access to food (standard rat/mouse pellets; Norco Feeds) and water. For short term storage a maximum of 15-16 mice were housed per cage while for longer periods this number was reduced to less than 10 mice per cage. Bedding material was wood shavings or more commonly recycled paper pellets (Breeders Choice).

A 12 hour light/dark cycle was maintained in the animal holding facility with lights on at 06:00 hrs. All testing was performed during the light phase to minimise any diurnal variation in behaviour. The temperature of the facility was maintained at 21° C. with humidity ranging between 45 and 65%.

Newly acquired animals were housed in the holding facility for a minimum of two days prior to being used for testing.

Test Compounds.

Formalin (Ajax) was supplied as solution of approximately 37.5% formaldehyde containing 10% methanol as a preservative. This stock solution was diluted 1:20 with water to give a 2% formaldehyde solution (5% formalin) which was used as the nociceptive agent.

Morphine hydrochloride was kindly donated by Extal, a division of Tasmanian Alkaloids Pty. Ltd. and appropriate concentrations were made by dilution with sterile isotonic (0.9%) saline.

Testing Method.

In the absence of a dedicated room for testing, all tests were performed in the laboratory on weekends during times consistent with the first hours of the light phase in the holding facility. These times were chosen to minimise disturbances during testing due to other workers in the laboratory and to minimise any variation in response due to time of the day.

The mice were brought into the laboratory at least one hour prior to testing. Subsequently the mice were individually placed into empty colony cages, which also served as observation chambers. They were allowed a further 30 minutes to explore their environment. During this time, and during testing, no food or water was available.

Morphine and other compounds of interest were injected in a volume of 10 mL/kg intraperitoneally (ip) 30 minutes prior to formalin administration. With minimal restraint, 20 µL of formalin solution was injected subcutaneously (sc) into the dorsal surface of the right hind paw. The mouse was replaced into the cage and observations begun immediately. The sole behavioural response recorded was the amount of time the animal spent biting or licking the injected paw or leg per 5 minute block was recorded. Each animal was used once only for testing and were subsequently euthanased by $CO_2$.

Results.—Control.

Two control experiments were performed to ensure that the assay gave comparable results to the literature. In addition a background, grooming behaviour was recorded. This data was recorded as the amount of time that the mouse spent biting or licking both hind paws, with the average value taken as the normal grooming background (FIG. 12). The mouse was given ip saline only for these observations.

FIG. 12 indicates that the amount of time that the mice spend grooming their hind paws is approximately 4 seconds every 5 minutes. Although there was some small variation in this time, it was decided that these values were not significant and were therefore not included in further calculations.

The second control experiment involved an ip injection of isotonic saline followed, 30 minutes later, by injection of formalin. The results for the controls are shown in FIG. 13. The characteristic biphasic nature of the response reported by previous workers (e.g. [61]) is shown in FIG. 13.

The final control experiment conducted to ensure the validity of the technique was to construct a dose response curve for morphine. Four doses of morphine were chosen, 3 mg/kg (n=8), 6 mg/kg (n=7), 9 mg/kg (n=6) and 12 mg/kg (n=4). A calculation of analgesic activity over the total experimental time period was required to evaluate the extracts as analgesics. Any differences observed between the acute and tonic phases of the nociceptive response were noted. A comparison between the duration of experimental and control pain for the entire experimental period (45 min) was needed.

The total time spent exhibiting the pain response in control animals was 451±28 seconds ($\bar{x}$±S.E.; n=18). Using this value a percentage pain inhibition can be calculated using the formula:—

$$\text{Pain response (\%)} = (1 - \text{Response time(sec)}/\text{Control time}) * 100$$
$$= (1 - \text{Response time(sec)}/451) * 100$$

where response time is the average pain response time recorded over 45 minutes when observed after administration of the compound of interest. The morphine dose response curve for the entire experimental period is shown in FIG. 14 ($ED_{50}$=4.8 mg/kg).

Previously it has been demonstrated that the effect of morphine is greater in the later, tonic phase than in the early, acute phase in the formalin assay. An approximate $ED_{50}$ value of morphine between 4 to 5 mg/kg has been reported for the acute phase in mice whereas in the tonic phase 2 to 3 mg/kg of morphine is required (e.g. [62]). For the entire experimental period subcutaneous morphine gave an $ED_{50}$ value of 4.8 mg/kg [63] and it has also been noted that almost complete analgesia was induced at 6 mg/kg [64]. The results obtained for the current work showed similar trends.

Summary.

In summary, the formalin assay was found to be reliable, easy to perform and provided sufficient information from a minimal number of experimental subjects. The control results of the assay compare favourably with those of other workers. The method conforms to the ethical guidelines of the ISAP [65, 66] and the Griffith University Ethics Committee for Experimentation on Animals (GUECEA).

Section B—Isolation of Compounds of Invention from *Barringtonia*

Introduction.

Crude extracts and fractions from *Barringtonia* were tested for effectiveness in pain inhibition using the mouse formalin assay.

The separation of saponins, and subsequent characterisation, requires the use of sophisticated techniques. Purification of saponins is achieved by many methods that are discussed later (e.g. [67-69]), but in general involves the following (FIG. 15). Extraction in aqueous alcohol (methanol or ethanol), either preceded or followed by a defatting step, removal of the solvent and suspension of the residue into water saturated n-butanol. At this stage the saponins can be precipitated with diethyl ether, however this step may be omitted. The residue is subsequently subjected to chromatography. This last step may involve several techniques, including Sephadex LH20, silica, Diol or reverse phase (C8 and C18) chromatography, alone or in combination. The technique of counter current chromatography and its variations (DCCC, RLCC, CPC) has also found application in the separation of saponins.

The major problem associated with the isolation of saponins using chromatographic techniques is the lack of a suitable chromophore for UV detection. Although these problems can be overcome by using RI, mass detection and by derivatisation and UV detection, each of these techniques has its own inherent advantages and difficulties which have been discussed elsewhere [67].

The use of bioassay to guide the purification may, however, dictate the isolation methods used. This section describes the processes which led to the separation of several pure saponins from the aqueous extract of the bark of *Barringtonia acutangula*.

Experimental

General Methods and Materials.

The mouse formalin assay was performed as described previously. Assay results were reported as the percentage inhibition of the pain response compared to controls (see Section A).

Unless stated otherwise all solvents and reagents were AR grade. Pure water (ddH$_2$O) (Permutit Australia, conductivity <0.07:S/cm) was used for all separations. High purity (Omnisolve, EM Science) methanol (MeOH) and acetonitrile (MeCN) were used for all analytical HPLC separations, whereas distilled AR grade MeOH and HPLC grade MeCN were used for semi-preparative and preparative separations. All solvents, including water, were filtered (0.450 m nylon, Activon) before use.

NMR was performed using a Varian 200 MHz (Gemini 200), 400 MHz (Unity), 500 mHz (Unity Inova) or 600 MHz (Unity Inova fitted with Ultra Shims) system using deuterated solvents (CD$_3$OD, CD$_5$N, d$_6$-DMSO). Where only small amounts of sample were available, D$_2$O or DMSO matched Shigemi NMR tubes (3 or 5 mm) were used in order to present a more concentrated sample to the NMR. All chemical shifts were reported in parts per million (ppm). Standard Varian pulse sequences were used for all experiments.

Low resolution electrospray mass spectrometry (LR-ESMS) was performed on a Fisons VG Platform LCMS connected to a Waters 600 HPLC system (methanol, flow rate 0.9 mL/min). Spectra were collected in both negative and positive ion modes, at a range of cone voltages (±50V, ±100V, ±150V and ±200V), and were analysed using MassLynx software. High resolution ESMS (HR-ESMS) was performed at the Australian Institute of Marine Science, Townsville Queensland. The instrument was a Bruker (Billerica Mass., USA) BioApex 47e FTMS equipped with an Analytica of Branford (Branford Conn., USA) external electrospray source. The instrument was calibrated in either positive or negative mode prior to sample infusion and molecular masses were reported to within 5 ppm.

Plant Material.

The plant sample was identified as *Barringtonia acutangula* (L.) Gaetm. ssp. *acutangula* and a voucher was lodged at the Queensland Herbarium (#AQ595351). Although the tree is found across Northern Australia, the sample used in this project was collected from the Kimberley district of North Western Australia. An initial collection of the bark from the tree was made on Jul. 14$^{th}$ 1989 and a subsequent collection was made in 1994. In order to ensure similar characteristics the collection was made from the same area and at the same time of the year (Jul. 18$^{th}$ 1994). A small sample of flowers and leaves was also made available.

The flowers of *B. acutangula* are small and a large number were required to provide sufficient material for further investigation. The tree flowers in the rainy season, at which time the area becomes flooded making collection difficult. Therefore no further collections were possible and the activity in the flowers remains to be investigated. A quantity of bark was available from the initial collection from which the activity had been demonstrated. Therefore the current work aimed to characterize the analgesic activity in the bark.

Bark was removed from the trees by the aboriginal people who lived in the area in such a manner as to inflict minimal damage and ensure the continued growth of the tree. The bark samples were air or oven dried at a maximum temperature of 50° C. The dried samples were mill ground to a coarse powder and the powdered sample stored in an airtight container at room temperature until ready for extraction.

The small sample flowers and leaves were dried, powdered and stored in a similar manner the bark.

Extraction of Plant Material.

The dried and powdered bark was soaked for several hours in approximately ten volumes (w/v) of demineralised water (dH$_2$O). The resulting mixture was filtered through several layers of muslin, centrifuged (Damon IEC Division DPR6000, 4500 g for 45 min) and the supernatant freeze dried (Virtis Freezemobile 12). The dried extract was stored in airtight containers at 4° C.

The flowers (0.25 g) and leaves (1.35 g) were extracted with dH$_2$O in a similar fashion to the aqueous extraction of the bark.

Several methods were employed to fractionate the bark H$_2$O extract and are described below.

Method 1.

The water extract was redissolved in ddH$_2$O for assay or further purification. A significant amount (~30%) remained undissolved and was removed by centrifugation (Sorvall RC5B Plus, 12,000 g, 20 min) followed by filtration (0.45:m nylon, Activon). Where required the H$_2$O insoluble portion of the extract was assayed as a suspension.

In addition to H$_2$O, several alternative solvents were used and the filtrate (0.45:m nylon, Activon) from these extractions was subsequently assayed. Alternative solvents included MeOH, CHCl$_3$, MeOH:CHCl$_3$ (1:9), MeOH:trifluoroacetic acid (TFA, 0.5%), ethyl acetate (EtOAc), 1% ammonia solution (NH$_4$OH), dimethyl sulfoxide (DMSO) and dimethyl formamide (DMF). Acetylation, hydrolysis and sonication of the H$_2$O insoluble portion are described below. Extracts were assayed as described previously.

Method 2.

Dried water extract, prepared as in method 1, was dissolved in 1% ammonia solution (Ajax) and centrifuged (Sorvall RC5B Plus, 12,000 g, 20 min) to remove any insoluble material (~22%). The supernatant was applied to a TSKHW40S column (vide infra) and eluted at 5 mL/min with 1% NH$_4$OH.

Initially water was used as the mobile phase, however the small amount of ammonia was found to produce sharper, better resolved peaks. The water extract was dissolved in the mobile phase to minimise any problems resulting from precipitation of extract on the column. Initially five fractions, labeled as TSK-1, TSK-2, TSK-3, TSK-4 and TSK-5 were collected according to the resulting chromatogram. However, difficulties in consistently separating TSK-4 from TSK-5 led to both of these fractions being pooled as TSK-4a. Extracts were assayed as described previously.

The active fraction from the gel permeation (TSK4a) column was dissolved in MeOH, filtered (0.45:m nylon, Activon) and applied to a preparative C18 column (vide infra). The column was eluted using a step gradient of MeOH in ddH$_2$O (0, 35, 70 and 100% MeOH) and the fractions collected according to the resultant chromatogram.

Method 3.

The method utilised in this section was similar in all respects to method 2, the only difference was in the step gradient used for preparative C18 chromatography. In this instance a step gradient was employed which consisted of 10% increments of MeOH in ddH$_2$O (0-100% MeOH).

Method 4.

In this method the water extract was applied directly to a C18 preparative column omitting the need for a gel permeation step. The water extract was dissolved in dH$_2$O, centrifuged (Sorval RC5B Plus, 12000 g for 20 min) and the supernatant applied a C18 preparative column (vide infra) and the column eluted as in method 3.

Separation of Active Fractions.

The methods used for separation of crude, active fractions into pure compounds were developed on an individual basis. The columns used to facilitate separations included C18, C8, diol and phenyl bonded silica. Suitable mobile phases included MeOH, MeCN, isopropanol (i-PrOH), hexane, EtOAc, H$_2$O, 0.01 M HAc and 1% TFA. In general the approach used was to begin with a C8 or C18 column and a gradient of MeOH or MeCN with H$_2$O or 1% TFA (early separations used 0.01 M HAc). Modifications to the method were made until it became necessary to use a different column (e.g. phenyl or diol) and the process repeated in order to provide maximal separation and resolution. The methods adopted for each fraction are discussed in the relevant areas of the results and discussion sections.

Chromatography.

Analytical and Semi-preparative Chromatography.

Semi-preparative and analytical chromatography were performed using a Waters 600 HPLC system fitted with a photodiode array detector (PDA 996), an autosampler (717 plus) and a fraction collector. Chromatographic information was collected and stored using Millennium 2010 chromatography manager software (version 2.10).

Analytical chromatography was performed using Dynamax columns in one of two formats. Reverse phase (C18 or phenyl) columns were either 4.6×250 mm (8:m irregular silica, 60 Å pore size, 1 mL/min) or 4.6×50 mm ("Short Ones", 3:m spherical silica, 60 Å pore size, 1 mL/min). Similarly, semi-preparative chromatography was performed using reverse phase (C18 or phenyl) columns which were either 10×250 mm (8:m irregular silica, 60 Å pore size, 4 mL/min) or 10×50 mm ("Short Ones", 3:m irregular silica, 60 Å pore size, 4 mL/min). All solvents used for analytical and semi-preparative chromatography were degassed by helium sparging.

Preparative Chromatography.

Large scale preparative chromatography (gel permeation and C18-silica) was performed using either a Gilson (Model 303 pump, 804 manometric module) or a Waters 600 HPLC system fitted with an extended flow kit. Both systems were connected to a UV detector (254 nm, absorbance mode) (ERMA Optical Works, ERC 7215), a fraction collector (ISCO Foxy or Waters) and either a chart recorder (Omniscribe series D5000) or an integrator (C-R6A Chromatopac, Shimadzu).

Gel permeation chromatography was performed using TSKHW40S packing (Merck) in a 49×350 mm glass column (Büchi) (flow rate 5 mL/min, 4 min fractions).

C18-silica preparative chromatography was performed using a 26×230 mm glass column (Bü) (flow rate 12.5 mL/min) and fractions were collected according to the resultant chromatogram. During the early stages of the work separations were accomplished using laboratory prepared C18-silica packing, in contrast to later separations where C18-Davisil (Alltech) packing material was used. The preparation of the C18 silica is described below.

Preparation of C18-silica for Early Preparative Chromatography.

The entire procedure was conducted under a dry nitrogen atmosphere. Toluene (AR, Ajax) was dried over sodium wire, distilled and stored over sodium wire and 3 Å sieves (Ajax). MeOH and dichloromethane (DCM) were distilled and stored over 3 Å sieves. A slurry was made using dry toluene (400 mL) and dry silica gel (200 g, 40-63:m, Merck) to which octadecyl trichlorosilane (40 mL, Fluka) was added and the mixture stirred for 24 hr. The slurry was subsequently filtered via a Büchner funnel and the product washed sequentially with 400 mL each of dry toluene, dry MeOH and dry DCM. Finally the non-end capped C18-silica product was dried at 37° C. for 24 hr. End capping was achieved by suspending the non-end capped C18-silica in 400 mL of dry toluene, adding 40 mL of trimethylchlorosilane (Fluka) and allowing the mixture to stand for 24 hr. The final product was washed successively with 400 mL dry toluene and 400 mL dry DCM before being dried at 37° C. for a further 24 hr.

Acetylation of the Insoluble Component of the Water Extract.

A 1 g sample of the water insoluble portion of the water extract was added to 5 mL dry pyridine (reflux over sodium wire, store over 4 Å sieves). The mixture was cooled to 0° C., 1 mL of acetic anhydride added and the mixture stirred overnight at room temperature (RT). Ice (1-2 g) was added to quench the reaction. The mixture was partitioned into ethyl acetate (25 mL of ddH$_2$O and 25 mL ethyl acetate). The organic layer was retained and washed successively with 10 mL each of 1M HCl, ddH$_2$O saturated NaHCO$_3$ and again with ddH$_2$O. Finally the organic layer was dried over Na$_2$SO$_4$ or MgSO$_4$ and the solvent evaporated to dryness.

Base Hydrolysis of the Insoluble Component of the Water Extract.

A schematic for this process is shown in FIG. 16. A sample (0.5 g) of the active, water insoluble, portion of the water extract was added to 20 mL of 0.5M NaOH, stirred for 1 hr and subsequently centrifuged (12,000 g, 15 min). The pellet (360 mg) was washed repeatedly with ddH$_2$O until the filtrate became clear. A portion of this pellet (330 mg) was extracted with 20 mL of DCM and centrifuged as before to recover the pellet (320 mg). The pellet (100 mg) was added to 10 mL of 2M NaOH, refluxed for 2 hrs and allowed to cool overnight. The mixture was partitioned successively into DCM (20 mL) and n-butanol (20 mL) and the solvent evaporated in vacuo.

The pH of the aqueous layer adjusted to 7 with 1M HCl. Again the aqueous phase was successively partitioned into DCM and n-butanol and the solvent removed in vacuo. Finally the aqueous phase was acidified (pH 1) with 1M HCl, partitioned into DCM and n-butanol and the solvent removed as previously. The solvent remaining in the aqueous phase was also removed in vacuo. Samples from all steps were assayed for activity.

Acid Hydrolysis of the Insoluble Component of the Water Extract.

The procedure for acidic hydrolysis closely follows the procedure outlined for base hydrolysis. The active, water insoluble, portion of the water extract was treated as for base hydrolysis and a portion of the pellet (100 mg) was subjected to acid hydrolysis as outlined in FIG. 16.

Sonication of the Insoluble Component of the Water Extract.

A sample of the active insoluble material was sonicated (20 kHz, 300 W for 10 min) in water. Both the soluble and insoluble material were assayed.

Results and Discussion.

The aim was to examine analgesic effects of a water extract and subsequently purify and characterized the compound(s) responsible for the activity.

Flowers and Leaves.

Aqueous extration of the flowers and leaves resulted in 12.8 mg and 139.6 mg of flower and leaf extract, respectively, which were used in a formalin assay, as described previously. The results of the assays are shown in FIG. 17.

The activity of the flowers was very high (~70% inhibition) at 5 mg/kg whereas the leaves produced little activity (~18% inhibition) at the same dose.

Method 1.

The powdered bark was extracted in dH$_2$O to give a crude water extract (9.8%). The crude water extract was dissolved in ddH$_2$O at a concentration of 10 mg/mL/kg and assayed for analgesic activity as previously described. These results can be seen in FIG. 18.

From FIG. 18 it was clear that this extract produced a considerable reduction in the pain response (78%) when compared to controls (see Section A). It can also be seen that the pain response, as measured by the formalin assay, is much reduced and confined to the acute stage. However it was noted that this extract contained particulate matter, which was approx 40% of the total weight of the extract. This suspension was filtered and both the soluble and insoluble material assayed separately at a dose of 10 mg/mL/kg. It was found that the analgesic activity was higher (66%) in the insoluble material than in the soluble material (45%). However in both cases some pain response was observed in the tonic phase of the assay, although this was more evident in the water soluble portion of the extract (FIG. 18).

Acetylation of the active water insoluble portion of the water extract reduced the activity from 66% to 28% pain inhibition and therefore did not prove to be a useful technique in the separation of active constituents.

Given these results it appeared that a significant amount of the activity was not soluble in water. An attempt was made to extract the activity from the insoluble component bark by using a variety of solvents (Table 1). All extracts were assayed at 10 mg/kg/mL as previously described.

The Merck Index states that DMSO has anti-inflammatory activity, has been proposed as an analgesic and has also been used as a penetrant carrier to enhance absorption of compounds. Although the DMSO extracts were freeze dried some residual DMSO always remained. Therefore it was important to determine whether residual DMSO interfered with the assay. Although a high dose was used (5%), DMSO was found to reduce the pain response by 57%. Therefore in order to avoid any interference, DMSO was not considered for any further extraction. Therefore, as can be seen from Table 1, the water extract was at least as active in the mouse formalin assay as the extracts from other solvents. As no additional extraction could be achieved by the other solvents it was decided to characterise analgesic activity in the water extract.

At this time it was decided to construct a dose response curve for both the water soluble and the water insoluble extract and compare the results (FIG. 20). From these results it can be seen that the amount of extract required to reduce the pain response by 50% ($ED_{50}$) is approximately 36 mg/kg (soluble) and 5 mg/kg (insoluble). These results, combined with the ease of extraction, further supported the decision to concentrate further purification effort on the water soluble material.

Method 2.

This method involved a preparative gel permeation separation of the water soluble extract. Initially five fractions were collected and, with respect to the starting H$_2$O extract, the following average yields were obtained, TSK-1 0.4%, TSK-2 15%, TSK-3 23%, TSK-4 0.7%, TSK-5 20% and an insoluble portion (22%). Fractions TSK 1 to 5 were assayed at a crude water soluble equivalent dose of 100 mg/kg (i.e. approximately 2.5 times the $ED_{50}$) and the results can be seen in Table 2.

Although the greatest apparent reduction in the pain response was seen in fraction 2 (74%), this required 15.8 mg/kg of material. In contrast, 0.7 mg/kg of fraction 4 was required to produce a 31% inhibition of the pain response, suggesting that fraction 4 was approximately ten times as potent as fraction 2. However, the small peak which eluted as TSK-4 was often obscured by the much more intense peak of TSK-5. Therefore the separation of fractions TSK-4 from TS K-5 proved to be inconsistent and in subsequent separations they were pooled and named TSK-4a. The following average yields, with respect to the starting H$_2$O extract, were obtained, TSK-1 1.7%, TSK-2 23%, TSK-3 20%, TSK4a 16% and an insoluble portion (17%) (FIG. 21).

At this point a dose response curve was constructed for fraction TSK-4a (FIG. 22). This graph showed that an $ED_{50}$ for this extract was approximately 1.8 mg/kg. This represents an overall purification of the analgesic activity some 30 times that of a crude water-soluble extract of the bark.

Further separation of the active fraction (TSK-4a) was achieved by elution from a preparative C18 column with a step gradient of 0, 35, 70 and 100% MeOH in H$_2$O. The resulting chromatogram is shown in FIG. 23.

The fractions were collected as evidenced by the chromatogram, dried in vacuo and assayed. The following average yields, with respect to the TSK-4a starting material, were obtained, 0%-MeOH 54%, 35%-MeOH 17%, 70%-MeOH 2.4%, 100%-MeOH 0.7% and an insoluble portion 2.2% The dosage used for assay was an equivalent to 3 mg/kg of the TSK-4a (approx two times $ED_{50}$). The results of the assays are show in Table 3.

These results showed activity in all fractions eluted from the column, although the activity eluted at 0% was small in comparison to the other fractions. (It was of Interest to note that the fraction which eluted in 70% methanol sedated the mice whereas the other fractions did not). Attempts to further separate each fraction indicated that, as expected, each fraction still contained a large number of compounds.

Method 3.

Using a preparative C18 silica column to separate the activity demonstrated in fraction TSK4a, the number of steps in the gradient was increased from four to eleven (10% increments, 0-100% MeOH in $H_2O$). The resulting chromatogram can be seen in FIG. 24 and the yields obtained, with respect to the TSK-4a starting material, were 0%-MeOH (F0) 61.5%, 10%-MeOH (F10) 3.6%, 20%-MeOH (F20) 3.2%, 30%-MeOH (F30) 2.9%, 40%-MeOH MeOH (F40) 2.6%, 50%-MeOH (F50) 1.6%, 60%-MeOH (F60) 0.9%, 70%-MeOH (F70) 2.4%, 80%-MeOH (F80) 0.2%, 90%-MeOH (F90) 0.1%, 100%-MeOH (F100) 0.2% and an insoluble portion 3.1%.

Again each fraction was assayed and the results can be seen in Table 4. The results of these assays indicated that the most potent fractions, on a % inhibition/mg of extract basis, were those eluted at 70, 80 and 90% MeOH.

However, it soon became obvious that each of these fractions still contained a large number of compounds and that the yields obtained via this method were insufficient to supply sufficient pure compound for further analysis. It was suspected that cumulative losses during the isolation steps resulted in the low yields. Therefore large scale work-up by direct chromatography on C18 was performed in order to obtain large quantities for further fractionation.

Method 4.

It was established that most activity was eluted from a C18 column using 70, 80 and 90% MeOH as the mobile phase. Therefore the gel permeation step was omitted and the water soluble extract was applied directly to a C18 preparative column after removal of any insoluble portion by centrifugation and filtration. The resulting chromatogram is shown in FIG. 25.

The first of the separations which were performed using this method used C18 silica which was prepared in the laboratory whereas later separations were performed using commercially available C18 packing material (Alltech Davisil). A comparison between the yields obtained using both packing materials is shown in Table 5 below.

As had been previously decided, in order to minimize the number of animals used no further testing for analgesic activity was performed. Therefore activity in each of the fractions which were eluted from this procedure was not confirmed. However, it should be noted that if activity was present in fractions which elute from a C18 column at 70, 80 and 90% MeOH in $H_2O$ then it follows that the active constituents will also be found in the same fractions, albeit in lower concentrations, even though prior separation steps were omitted. It was on this basis that the investigation continued to examine those fractions which eluted with 70, 80 and 90% MeOH in $H_2O$ from the preparative C18 column. A preliminary $^1$H-NMR of all fractions suggested that the predominant compounds in the fractions collected were saponins and tannins. The tannins were found in the fractions eluting at lower MeOH concentrations while the saponins tended to elute at higher MeOH concentrations from the C18 column. Initially it was decided to limit this investigation to those fractions which eluted with 70, 80 and 90% MeOH. However it became apparent that a large number of compounds existed in each of these fractions.

Numbering Scheme for Collected Fractions.

In order to consistently identify fractions and compounds collected in the current investigation, the following numbering scheme was adopted. The first three digits identify the percentage methanol that eluted the original fraction from a C18 preparative column. The remaining digits identify the collected peaks in subsequent fractionations. This is shown diagrammatically in FIG. 26 for fraction F70.2.5.2.

Fraction Eluting at 70% Methanol (F70).

The fraction which eluted at 70% MeOH (F70) was further separated on a C18 semi-preparative (25 cm) column using a MeOH:1% trifluoroacetic acid (TFA) gradient. The TFA was added to the mobile phase in order to sharpen the peaks in the chromatogram. Early separations in the current project, which used single wavelength detectors and chart recorders, used acetic acid (0.01M) to improve the resolution. However TFA was chosen for later separations after it was determined that residual acetic acid was more difficult to remove than residual TFA. It was at this point that the advantages of using a photodiode array detector (PDA) became apparent. Conventional UV detectors are usually able to monitor the separation at a single wavelength. However the PDA was able to monitor the separation at several wavelengths simultaneously. As an example consider the chromatograms shown in FIG. 27. In general, saponins have no UV chromophore and are more likely to be detected at wavelengths approaching 210 nm. However it was found that high absorbances could be achieved at 233 nm. Indeed a separation of the extract could be adequately observed at 254 nm indicating the saponins present in the extract contained UV active chromophores FIG. 26 shows that, at the conditions employed for the separation and employing the three wavelengths shown, the extract could be separated into 5 distinct fractions. Varying the gradient conditions did not result in further separation of the peaks and therefore these five peaks were collected as indicated for further purification steps. Table 6 presents the yields obtained and preliminary $^1$H-NMR results which indicate that no pure compounds were isolated at this point.

Fraction F70.2.

Fraction F70.1 was not further investigated as $^1$H-NMR suggested that a considerable carryover from fraction F60 was present. Attempts to separate F70.2 (C18 25 cm) by altering the percentage of MeOH in the mobile phase did not result in further separation of fraction F70.2. A change in mobile phase to acetonitrile (MeCN):1% TFA mixtures proved more successful and an isocratic run of 40% MeCN in 1% TFA resulted in the separation of this fraction into 8 peaks (FIG. 28 and Table 7).

Preliminary $^1$H-NMR showed that fractions F70.2.3, F70.2.4, F70.2.6 and F70.2.7 were predominantly single compounds and repeated chromatography using identical conditions resulted in pure compounds with sufficient material to begin structural elucidation. However, on standing, the NMR samples in $d_6$-DMSO were found to contain minor impurities. This suggested that some minor hydrolysis of the compounds was occurring, possibly due to residual TFA which was not completely removed on drying. As the small amount of impurity present did not interfere with the structural elucidation, and the amount of pure compound was small, obtained no further attempts to remove the impurity were made. A chromatogram showing chromatographic purity of fraction F70.2.6 recorded at 220,233 and 254 nm is shown in FIG. 29.

As previously mentioned purity of all fractions was determined by $^1$H—NMR, the NMR solvent being $d_6$-pyridine. However, when the solvent was removed by freeze drying, one or more compounds within the fraction were found to have reacted with the NMR solvent to produce a bright pink complex. This was particularly noticeable with fraction F70.2.2. $^1$H-NMR of the complex tended to suggest that the compounds in the fraction had not altered, however a considerable amount of pyridine remained. Re-chromatography of the fraction did not remove the pink colouration and attempts to remove the remaining pyridine by prolonged freeze drying or by azeotroping the pyridine with a small amount of benzene or toluene were unsuccessful. Therefore a repeat extraction was performed to obtain sufficient compound for structural elucidation and all subsequent NMR spectra were obtained with $d_6$-DMSO as the solvent.

Fraction F70.2.1 was not fractionated further as H-NMR suggested that it consisted largely of compounds carried over from fraction F70.1. No further separation of fraction F70.2.2 was possible using C18 or C8 columns with MeOH or MeCN in either $H_2O$ or 1% TFA as the mobile phase. However, preliminary $^1$H-NMR indicated the presence of aromatic signals. Separations using phenyl bonded silica are based on p interactions. Therefore a phenyl column (5 cm) was used to separate fraction F70.2.2 into eight fractions as shown in FIG. 30 and Table 8. Although the fractions obtained from F70.2.2 were mixtures, peaks F70.2.2.3, F70.2.2.6 and F70.2.2.7 were predominantly single compounds by $^1$H-NMR . However insufficient material was available to re-chromatograph the fractions in order to obtain enough pure compound for structural elucidation.

Of the remaining peaks, only F70.2.5 was obtained in sufficient quantity to attempt further separation. Attempts to separate F70.2.5 using C18 and C8 columns were unsuccessful while phenyl bonded silica (5 cm) resolved F70.2.5 into eight peaks using a MeOH in 1% TFA gradient (FIG. 31 and Table 9).

Total yield for this fraction was lower than expected from previous separations. However it was noticed that F70.2.5 did not completely dissolve in MeOH and therefore some material was lost during filtration. Of the eight peaks obtained from F70.2.5 only F70.2.5.2 was isolated in sufficient purity and quantity to attempt a structural assignment. Peak F70.2.5.3 was also isolated in sufficient quantity, however the peak contained two compounds by $^1$H-NMR which could not be further resolved. Although by $^1$H-NMR peaks F70.2.5.5 and F70.2.5.6 were predominantly single compounds, they were found to contain several compounds when further fractionation was attempted. Consequently insufficient material was available for structural elucidation.

Fraction 70.3.

As was the case with F70.2, fraction F70.3 could not be satisfactorily separated using MeOH/1% TFA mixtures. Again MeCN in 1% TFA gradients were used and F70.3 was separated into seven fractions (FIG. 32 and Table 10) using a semi-preparative C18 silica (25 cm). Again the separation could be monitored successfully at 233 nm.

Although no compounds were 100% pure by HPLC or $^1$H-NMR at this stage, repeated chromatography using identical conditions allowed the final isolation of five peaks (F70.3.2, F70.3.5, F70.3.6 and F70.3.7). FIG. 4.18 shows chromatograms of fractions F70.3.5 and F70.3.7 indicating the peaks which contained pure compounds as shown by $^1$H-NMR immediately after drying the samples. It should also be noticed that even though the peak isolated as F70.3.7 appeared to be pure by 1 H-NMR and by HPLC, the compound appeared to decompose, producing peaks which eluted at the same retention times as F70.3.6 and F70.3.5 (FIG. 33).

Using MeCN/1% TFA as the mobile phase on a C18 column (25 cm), F70.3.4 was separated into eight peaks as shown in FIG. 34 and Table 11. In all eight peaks were collected, however only compounds F70.3.4.2 and F70.3.4.5 were obtained in sufficient quantity or purity to allow structural assignment.

The $^1$H-NMR of fraction F-70.3.3 showed that it consisted of three major compounds. This peak was subjected to further chromatography in order to separate these compounds however no further resolution could be obtained.

Fraction F70.4

An initial separation of F70.4 was achieved using a 70% MeOH/1% TFA gradient on a C18 semi-preparative column (25 cm) (FIG. 35 and Table 12). As can be seen fraction F70.4.2 consisted of a single, large peak which upon closer examination, by both HPLC and $^1$H-NMR , was found to consist of several compounds. Further separation of F70.4.2 was not obtained with C18 or C8 columns using MeOH or MeCN gradients and as $^1$H-NMR showed the presence of aromatic protons in F70.4.2 a phenyl column (5 cm) was used. An isocratic mobile phase of 35% MeCN in 1% TFA separated F70.4.2 into four major peaks (FIG. 36 and Table 12A).

Repeated chromatography using identical conditions led to F70.4.2.2, F70.4.2.3 and F70.4.2.4 being obtained in sufficient quantity and purity to begin structural assignment. It was obvious from the FIG. 35 and also from $^1$H-NMR that F70.4.3 contained more than one compound. No improvement in separation of this fraction could be achieved using C18 or C8 reverse phase columns with MeOH or MeCN gradients, however a phenyl column (5 cm) again provided the separation. Although a separation could be obtained using either MeOH or MeCN gradients as the mobile phase, the separation obtained using MeCN in 1% TFA gradient provided better resolution of the peaks (FIG. 37 and Table 13).

As can be seen from the chromatogram in FIG. 37, F70.4.3.1 was, as expected, a mixture of compounds. At least five peaks were observed in the chromatogram, however further separation on this fraction was not attempted. Repeated chromatography using identical conditions of fractions F70.4.3.2, F70.4.3.4 and F70.4.3.5 enabled these fractions to be obtained in sufficient quantity for structure elucidation. Fraction F70.4.3.3 was a mixture of mainly two compounds, however these compounds could not be successfully separated.

Fraction F80.

Preliminary separation of F80 was achieved using a C18 reverse phase column (25 cm), the chromatogram is shown in FIG. 38 and the yields in Table 14. Although six peaks were collected initially, it was noticed that F80.2 and F80.3 were unstable as evidenced by the loss of these peaks in the chromatogram over time (FIG. 38). Consequently it was not possible to obtain structural information of these compounds.

The peak which eluted as F80.4 clearly contained more than one compound as evidenced by the chromatogram and confirmed by $^1$H-NMR . No further improvement in the separation of this fraction was obtained using MeOH or MeCN gradients using a 25 cm C18 column. However a change to the shorter C18 column (5 cm) enabled a separation of the fraction into six peaks using a MeCN/1% TFA gradient (FIG. 39 and Table 15). The peak which eluted at F80.4.5 was subjected to further chromatography under identical conditions to yield a single pure compound (F80.4.5.2).

Repeated chromatography of F80.5 using identical conditions (C18 25 cm) resulted in the purification of a single compound.

Although chromatographically F80.6 appeared to be a single compound, $^1$H-NMR suggested that this fraction was a mixture of several compounds. The presence of aromatic signals in the $^1$H-NMR of F80.6 suggested that a phenyl bonded silica column (5 cm) would be useful. Both MeOH and MeCN in 1% TFA were employed as mobile phases and it was found that the best separation was obtained with an isocratic gradient (40% MeCN in 1% TFA). This allowed the separation of F80.6 into eight fractions (FIG. 40 and Table 16). From these eight peaks it was possible to obtain five pure compounds (F80.6.2, F80.6.3, F80.6.4, F80.6.6 and F80.6.7) in sufficient quantity to attempt a structural assignment.

Summary.

The current project isolated 21 major and minor peaks to either purity or to sufficient purity to be able structural elucidation of the compounds. Table 17 shows the compound numbers and weights isolated. Before structural elucidation was commenced each of the compounds were checked by HPLC, under identical conditions to those in which they were isolated, in order to confirm their state of purity.

As can be seen from the previous discussion, in addition to the compounds shown in Table 17, a large number of fractions were isolated during the course of the current project. Many of these fractions contained a large number of compounds as evidenced by $^1$H-NMR and by the appearance of the chromatograms (i.e. a number of unresolved peaks). Several of these peaks appeared to contain only a small number of compounds, in some cases only one or two, as determined by $^1$H-NMR. However, insufficient plant material was made available to continue purification of these fractions. Table 18 presents some information on those fractions which would merit further investigation should more plant material become available for future work.

Section C—Compounds Structural Assignment

Introduction.

The assignment of a structure as a saponin requires identification of each of the component parts of the molecule and the sequence in which they exist. These considerations can be expressed as follows:-
- the structure of the genuine aglycone
- the number of sugar residues
- the nature and sequence of the sugars in the monosaccharide chain
- the anomeric configuration of each sugar unit
- the configuration and conformation of the interglycosidic linkage
- the attachment of the carbohydrate chain to the aglycone
- the nature and position of any acid in the molecule [1, 2, 6].

However it should be noted that although it is possible to obtain complete structures of saponins using NMR alone, confirmation of the assignment should, where possible, be provided by other methods.

Structural elucidation was carried out using known UV, IR, MS and NMR analysis.

Fraction F70.3.6—Chemical Elucidation

One of the first compounds isolated in the current work was F70.3.6, which was obtained-in relatively large yield (152.6 mg). The following is a summary of the techniques and methods used to assign a structure to F70.3.6.

Materials and Methods.

The materials and methods used for the isolation and structural elucidation of F70.3.6 are presented in detail in Section B.

Hydrolysis was achieved by refluxing a 10 mg sample in 1M HCl (Ajax). The solution was cooled and extracted with three 5 mL volumes of dichloromethane (DCM). The aqueous layer was neutralised with $Ag_2CO_3$ and filtered. Several mobile phases were tried to give a separation of the sugars and a chloroform ($CHCl_3$):MeOH:acetic acid (AcOH):$H_2O$ (7:3: 1:0.5) mixture proved successful on silica TLC plates (FIG. 41). Standard sugar solutions used were βD-glucuronic acid, β-D-fucose, β-D-glucose, ∀-L-arabinose, β-galactose, ∀-L-rhamnose, β-D-galacturonic acid and β-D-xylose.

The TLC plates were developed with a phenol-sulphuric acid solution (dissolve 3 g phenol and 5 mL 97% $H_2SO_4$ in 95 mL ethanol). The plates were dipped in the solution and heated at 110° C. for until spots visualise (10-15 minutes).

Instrumentation.

The methods and instrumentation used for NMR and ESMS are presented in detail in Section B. Compound F70.3.6 was also subjected to fast atom bombardment (FAB) MS in both positive and negative ion mode (Kratos Concept ISQ High Resolution/Quadrupole Tandem Mass Spectrometer, Central Science Laboratory University of Tasmania). The matrix used was meta-nitro benzyl alcohol (MNBA).

Sub-fractions from 70.2.5 were analysed and assigned structures through the use of spectra, in particular the $^1$H, $^{13}$C and $^1$H, $^{13}$CgHSQC (gHSQC), in a manner similar to that used above for fraction 70.3.60. The resultant structures fall within three categories, aglycones, monodesmosides and bidesmosides. The description of their structures begins with the aglycones. Where sugar residues in the mono- and bi-desmosides had identical structures and relative stereochemistry to F70.3.6, the absolute stereochemistry was also assumed to be the same.

UV Spectrum.

Little structural information could be determined from the UV (FIG. 42) or the FTIR (FIG. 43) spectra. The UV spectrum shows two strong absorbances at 205.9 nm (Abs.=1.78, e=11226) and 229.8 nm (Abs.=2.28, e=14430) and two weaker absorbances at 274.6 nm (Abs.=0.17, e=1076) and 280.0 nm (Abs.=0.14, e=886) (FIG. 41). These absorbances are consistent with K bands (B→B* transitions) and B bands in an aromatic system.

FTIR Spectrum.

The FTIR of a thin film of neat compound is shown in FIG. 43. The broad band centred at 3400 $cm^{-1}$ indicates O—H stretch and the group of peaks between 2820 and 3000 $cm^{-1}$ suggest C—H stretch. Ester carbonyl stretch was shown by the strong peaks at 1723 and 1709 $cm^{-1}$, while C—O stretch was seen between 1275 and 1039 $cm^{-1}$.

NMR Methods.

Initially it was decided to use NMR solvents which were reported in the literature, principally methanol (MeOH-$d_4$) and pyridine-$d_5$. However it soon became apparent that both solvents presented problems with the saponins isolated in the current work. The two problems encountered with MeOH-$d_4$ were solubility and the loss of exchangeable protons. Several of the saponins which were isolated were not soluble in MeOH-$d_4$ and of those that were, several precipitated in the NMR tube over time. The presence of a large number of overlapping signals in the $^1$H-NMR spectrum did not allow for assignment of many signals, in particular those which were due to the carbohydrate moiety.

Signals due to exchangeable protons may contribute to or complicate the overall structural information. However in this instance it was decided that exchangeable protons may assist in the final structural assignment, although more information was added to an already complex spectrum. Therefore pyridine-$d_5$, which seems to be the solvent of choice in the literature, was investigated. However the solvent signals tended to overlap the aromatic signals in the spectrum. Removal of the solvent also proved problematic. The solvent was removed in vacuo by freeze drying, however a substantial amount remained, even after several days. The solvent also appeared to react with some of the compounds to produce a bright pink complex. It was not clear from the $^1$H-NMR whether the compound itself had undergone any changes but it could be seen that a significant amount of pyridine remained. The addition of a small amount of benzene or toluene to azeotrope the pyridine, either by rotavap or freeze drying, did not resolve the problem.

Finally it was decided to use dimethyl sulfoxide (DMSO-$d_6$) as the NMR solvent, although little literature information was available for comparative purposes. The $^1$H-NMR spectrum of compound F70.3.6 in DMSO-$d_6$ can be seen in FIG. 44. The spectrum can be broadly divided into three regions. The first most shielded region (*0.00-*2.20) is predominantly associated with methyl signals. Six methyl singlets are evident in this region at chemical shifts of *0.71 (3H), *0.79 (3H), *0.84 (3H), *0.94 (3H), *0.97 (6H) and *1.33 (3H).

The second region (*2.20-*6.00) contains protons in close proximity to carbons bearing oxygen, notably four doublets characteristic of anomeric protons at *7.43, *7.52, *7.59, *7.66, *7.89 and *7.94. Finally the third, most deshielded region (*7.40-*8.00), indicates six aromatic protons at *7.43, *7.52, *7.59, *7.66, *7.89 and *7.94.

The $^{13}$C spectrum (FIG. 45) was less crowded than the $^1$H spectrum and readily allowed identification of several carbon types. These included five carbonyl carbons (*164.2, *164.3, *168.5, *169.6 and *171.9), two olefinic carbons (*121.6 and *141.7), eight aromatic carbons (*127.8, *127.9, *128.4, *128.5, *129.1, *129.5, *132.5 and *132.8) and four anomeric carbons (*101.8, *102.4, *102.8 and vi03.4).

Each region of the compound of F70.3.6 was analysed using $^1$H, $^1$H-dqfCOSY (dqfCOSY) and $^3$C-gHMBC (gHMBC) spectral analysis.

The assignment of chemical structures, including stereochemistry, were based on the NMR and other spectra obtained were carried out using known techniques. The fraction of F70.3.6 was assigned the structure of FIG. 46, shown below.

Mass Spectrometry.

The structure of F70.3.6 was determined by 1D and 2D NMR techniques, however supporting evidence for the structure was necessary. Although the UV and FTIR spectra gave some support for the assignment by indicating the functional groups present in the molecule, mass spectrometry (MS) better enabled confirmation of the assignment. This was possible by comparing the mass of the molecule as determined by high resolution MS and structure as assigned by NMR. Furthermore the mass of fragments produced in the MS also supported the NMR based structure.

Information in both positive and negative ion modes was obtained using electrospray (ES) as the ionisation source. Electrospray is a soft ionisation technique and use of ES ensured that minimal fragmentation of the molecule occurred under normal running conditions. The determination of an accurate mass was also possible using high resolution ES-MS. It was found that in positive ion mode the molecular ion was not as pronounced as in negative ion mode however more fragmentation was observed in positive ion mode. It is not uncommon for compounds in ES to form adducts, in particular with sodium in positive ion and chlorine in negative ion mode. This needed to be considered when assigning any peaks in the MS to fragments.

The literature reports most MS in negative ion mode for saponins and therefore this was the first mode investigated. The negative ion high resolution (HR) ES-MS showed all peaks as pairs indicating the monoisotopic mass and the mass of the compound containing one $^{13}$C (FIG. 47). The parent ion presented as two peaks at m/z values of 1441.6472 and 1442.6529. This mass is consistent with a molecular formula of $C_{73}H_{102}O_{29}$ (calculated 1442.6507) which supported the structure as assigned by NMR methods.

Structural Elucidation of Other Fractions

Other fractions where analysed in a similar manner to F70.3.6 above and the following compound structures were elucidated.

Aglycones.

Compound F70.2.5.2:—This compound was isolated as 7.2 mg of an amorphous white powder.

A compound related to F70.2.5.2,2α,3β,19α-trihydroxy-olean-12-ene-23,28-dioic acid 28-O-β-D-glucopyranoside, was previously isolated from *Barringtonia acutangula* [1]. This compound differs from F70.2.5.2 in that the acid at $C_{28}$ has a glucopyranoside moiety. Therefore the present compound is 2α3β,19α-trihydroxy-olean-12-ene-23,28-dioic acid (FIG. 48).

A second aglycone (F70.2.5.3) was isolated in the current project as 1.4 mg of a white substance. The mass of the compound was m/z 485.2912 ([M−1]$^-$), which is consistent with the molecular formula $C_{30}H_{46}O_5$ (calculated m/z 486.3345). This suggests the loss of two hydroxyl groups from F70.2.5.2, however insufficient material could be obtained to provide further structural information.

Monodesmosides—The monodesmosidic compounds described in the following section are grouped according to the functionalities present at $C_{21}$ and $C_{22}$ of the aglycone.

Benzoate at $C_{21}$ and Hydroxyl at $C_{22}$.

Compounds F70.2.3.2 and F70.3.2 were shown to have a benzoate moiety at $C_{21}$ and a hydroxyl group at $C_{22}$. Both were isolated as amorphous white solids in low yield (8.5 and 26.3 mg respectively).

Benzoate at $C_{21}$ and iso-butyrate $C_{22}$.

Compound F70.3.4.2—This compound was isolated as 11.7 mg of an amorphous white powder.

Benzoate at both $C_{21}$ and $C_{22}$: Compounds in this group each had a benzoate functionality at both $C_{22}$ and $C_{22}$. Four such compounds were isolated in the current project. Each of the four compounds were isolated as amorphous white substances and the weights were F70.4.3.5.2 (2.7 mg), F70.4.2.4.2 (4.9 mg), F80.6.4 (11.7 mg) and F80.6.7 (3.9 mg).

Benzoate at $C_{21}$ and tiglate at $C_{22}$.—The compounds in this group were characterised by a benzoate at $C_{21}$ and a tiglate at $C_{22}$. Four such compounds were isolated in the current project, each as an amorphous white mass, F70.4.2.3-42.7 mg; F70.4.3.4.2-6.4 mg; F80.6.3-25.8 mg; F80.6.6-4.3 mg.

Tiglate at both $C_{21}$ and $C_{22}$—The two compounds isolated in this series, F70.4.3.2.2 (2.8 mg) and F80.6.2 (7.4 mg) were characterised by tiglate groups at both $C_{21}$ and $C_{22}$.

Additional Compounds:

Fraction F70.3.3 was isolated as 47.8 mg of an amorphous white mass which was shown to contain several compounds by 1D and 2D NMR. Several attempts to resolve these compounds resulted in the collection of 6.6 mg of fraction F70.3.3.2.2, which still contained three compounds by 1D and 2D NMR. However it was possible to assign the structure of one of these compounds using a similar approach as for the other compounds.

Bidesmosides—Several compounds which had a sugar moiety at $C_{21}$ were isolated in the current project. In all instances this sugar was assigned as an arabinose.

Compound F70.2.6.2: In comparison to the other compounds isolated in the current project a relatively high yield was obtained for F70.2.6.2. This compound was isolated as 38.5 mg of an amorphous white powder.

Compound F70.3.4.5: A small quantity (2.7 mg) of F70.3.4.5 was isolated as an amorphous white compound. The structure of F70.3.4.5 is shown in FIG. 60.

Compound F70.3.5.2:

This compound was isolated as 12.2 mg of an amorphous white compound.

Compound F70.3.7.2:

Compounds F80.4.5.2 and F80.5.2:

These compounds were isolated as 2.8 mg (F80.4.5.2) and 20.1 mg (F80.5.2) of amorphous white masses.

Summary

This section summarises the structural assignment of the compounds isolated in the current project. In all one aglycone, ten monodesmosides and six bidesmosides were isolated and characterised. A search of the available literature based on either structure or molecular weight failed to find any of the mono- or bi-desmosides and they are at the time of writing assumed to be novel structures. The aglycone is, as mentioned a known structure from *Barringtonia acutangula*. There were many minor compounds in the extracts which also need to be characterised (see previous section). This would be facilitated by the collection of a substantial amount of bark and large scale preparative chromatography.

Section D—Analgesic Activity of F70.3.2 and F70.3.6

Preliminary investigation into whether intravenous administration of the test compounds F70.3.2 and F70.3.6, produce pain-relieving effects in a rat model of inflammatory pain.

Methods

Animals

Adult male Sprague-Dawley rats were housed in a temperature controlled room (21±2° C.) with a 12 h/12 h light/dark cycle and free access to both food and water. Ethical approval for this study was obtained from the Animal Experimentation Ethics Committee of The University of Queensland.

Reagents and Materials

Isoflurane (Forthane®) was obtained from Abbott Australasia Pty Ltd (Sydney, Australia). Sodium benzylpenicillin vials (600 mg) were purchased from CSL Ltd (Melbourne, Australia). Normal saline ampoules were obtained from Delta West Pty Ltd (Perth, Australia) and heparinised saline (50 IU/5 ml) was purchased from Astra Pharmaceuticals Pty Ltd (Sydney, Australia).

Single lumen polyethylene tubing (I.D. 0.5 mm, O.D. 1.00 mm) was purchased from Auburn Plastics and Engineering Pty Ltd (Sydney, Australia). Sterile siliconized silk sutures (Dysilk™) were obtained from Dynek Pty Ltd (Adelaide, South Australia).

Induction of Hindpaw Inflammation

Inflammation of the rat hindpaw was induced by intraplantar (i.pl.) injection of Freund's Complete Adjuvant (FCA, 0.15 mL) whilst rats were under brief 3% isoflurane: 97% oxygen inhalational anaesthesia. Inflammatory pain was assessed using the paw pressure test (see below for details). The test compounds were administered on either day 5 or day 6 following i.pl. FCA administration.

Paw Volume Measurement

The volume of each of the left and right hindpaws was measured using a plethysmometer on the day prior to i.pl. FCA administration, as well as immediately prior to i.v. drug (or saline) injection on day 5 post-FCA administration.

Surgery

Jugular Vein Cannulation

Jugular vein cannulation was performed whilst rats were anaesthetised with 3% isoflurane: 97% $O_2$ inhalational anaesthesia maintained using a calibrated Trilene vapouriser. Polyethylene cannulae (previously filled with heparinised saline) were implanted into the right common jugular vein for i.v. drug dosing. Cannulae were exteriorized by subcutaneous (s.c.) tunneling to an incision made in the interscapular area, and protected by a stainless steel spring, the base of which was positioned in a subcutaneous pocket between the scapulae. Incisions were closed with sterile silk sutures. After surgery, rats were housed singly in metabolic cages and were allowed to recover post-operatively for a minimum of 2 h before further experimentation. Food and water were available ad libitum during the recovery period.

Drugs Administered

Each of the compounds F70.3.2 and F70.3.6 were dissolved in sterile saline. The compounds of interest were administered initially in a dose of 0.01 mg/kg in an injection volume of 0.5 mL. The other i.v. doses administered in this preliminary study were as follows:

| | |
|---|---|
| F70.3.2 | 0.002 mg/kg, 0.005 mg/kg, 0.01 and 0.02 mg/kg |
| F70.3.6 | 0.002 mg/kg, 0.005 mg/kg, 0.01 mg/kg, 0.02 mg/kg and 0.05 mg/kg |

Control rats received bolus doses of i.v. saline.

Antinociceptive Testing: Paw Pressure Test

For the paw pressure test, rats were gently restrained under a towel, and incremental mechanical pressure (maximum=250 g) was applied to the dorsal surface of the hindpaw. The pressure required to elicit paw withdrawal, the paw pressure threshold (PPT), was determined. The mean of 3 consecutive measurements, separated by 10 s, was determined. The same procedure was then performed on the contralateral side with the sequence of sides being alternated to preclude order effects. Similarly, rats were gently restrained under a towel for the quantification of paw volumes using a plethysmometer.

Data Analysis

Following administration of i.v. bolus doses of each of the test compounds (F70.3.2 and F70.3.6), paw withdrawal thresholds (g) were normalized by subtraction of the individual baseline PWT values quantified immediately prior to drug administration. The area under the normalized PWT versus time (AUC) was calculated using the trapezoidal rule. Dose-response curves were constructed by plotting the AUC values versus the i.v. dose for each of F70.3.2 and F70.3.6.

FIG. 65 shows that for the ipsilateral hindpaw, there was a dose-related increase in the antinociceptive potency of F70.3.2. By contrast, there was an absence of antinociception in the contralateral hindpaw.

FIG. 66 shows that the ipsilateral hindpaw, there was a dose-related increase in the antinociceptive potency of F70.3.6 in the dose range, 0.002-0.01 mg/kg. However, further increases in the dose magnitude resulted in a decreased rather than an increased antinociceptive response. Similar to compound F70.3.2, there was an absence of antinociception in the contralateral hindpaw.

The results summarised in FIG. 67 in which rats where injected with saline only show that the experimental procedures themselves did not evoke significant antinociception The is a distinct increase and then plateau of the antinocieptive effect of compounds F70.3.6 and F70.3.2 using the above techniques, as shown in FIG. 68.

FIG. 69 shows that by 5 days post-FCA administration, the mean (±SEM) volume of the ipsilateral hindpaw increased approximately 2-fold from 3.3 (±0.1) mL to 6.0 (±0.1) mL. By contrast, the mean (±SEM) volume of the contralateral hindpaw at day 5 post-FCA administration (3.3 i 0.1 mL) did not differ significantly from that ((3.2)±0.1 mL) measured prior to induction of inflammation in the ipsilateral hindpaw.

A range of side effect were observed for the compounds F70.3.2 and F70.3.6 as summarized below in TABLE 19 and 20.

Throughout the specification the aim has been to describe the preferred embodiments of the invention without limiting the invention to any one embodiment or specific collection of features.

Throughout this specification, unless the context requires otherwise, the word "comprises", and variations such as "comprise" or "comprising", will be understood to imply the inclusion of a stated interger or group of integers or steps but not to the exclusion of any other interger or group of integers.

Reference may also be made to FIGS. 70 and 71 which show the structures of further compounds of the invention. FIG. 70 shows compounds (1) to (7) characterized by inclusion of groups A, B, C and D as shown. These compounds have been prepared from water extracts of the dried bark of *B acutangula* as described previously and have had their structure assigned as also described previously. Similar comments apply to the compounds of FIG. 71.

REFERENCES

1. Payens, J. P. D. W. (1967). A monograph of the genus *Barringtonia* (Lecythidaceae). *Blumea* 15(2):157-263.
2. Everist, E. L. (1974) *Poisonous plants of Australia*. Angus & Robertson
3. Quisumbing, E. (1978) *Medicinal plants of the Philippines*. Quezon City. Katha Publishing.
4. Carr, T. (1947). *Barringtonia acutangula* as fish poison. A practical application. *North Queensland Naturalist* 15: 3-4.
5. Cox, P. A. (1979). Use of indigenous plants as fish poisons in Samoa. *Economic Botany* 33(4): 397-399.
6. Lahil, J. K. and Ghosh, S. (1942). Chemical examination of the seeds of *Barringtonia acutangula* Gaertn. *Journal of the American Pharmaceutical Association* 31(7): 193-194.
7. Webb, L. J. (1959). The use of plant medicines and poisons by Australian Aborigines. *Mankind* 7:137-146.
8. Barua, A. K., Dufta, S. P. and Pal, S. K. (1967). Chemical examination of *Baffingtonia acutangula* Gaertn.
9. Sharma, B. M. and Singh, P. (1976). Pharmacognostic study of fruits of *Barringtonia acutangula* Gaertn. *Herba Hungarica* 15(3): 7-14.
10. Cribb, A. B. and Cribb, J. W. (1982). *Useful wild plants in Australia*. Sydney. Fontana Books.
11. Webb, L. J. (1948). Guide to the medicinal and poisonous plants of Queensland. *Council for Scientific and Industrial Research* Bulletin no. 232.
12. Watt, J. M. and Breyer-Brandwijk, M. G. (1962). *The medicinal and poisonous plants of Southern and Eastern Africa. Being an account of their medicinal and other uses, chemical composition pharmacological effects and toxicology in man and animal*. 2nd ed. Edinburgh and London. E and S Livingstone Ltd.
13. Uphof, J. C. T. (1968). *Dictionary of economic plants*. 2nd edition ed. Würzburg. Richard Mayr.
14. Jebb, M. (1992). Edible *Barringtonias*. *Kew Magazine* 9(4): 164-180.
15. Tanaka, T. (1976). *Tanaka's cyclopedia of edible plants of the world*. ed. S. Nakao. Tokyo. Keigaku Publishing Company.
16. Cribb, A. B. and Cribb, J. W. (1981). *Wild medicine in Australia*. Sydney. Fontana Books.
17. Worseley, R. R. L. (1934). The insecticidal properties of some East African plants. *Annals of Applied Biology* 21: 649-669.
18. Lassak, E. V. and McCarthy, T. (1990). *Australian medicinal plants*. Port Melbourne. Mandarin Australia.
19. Ahmad, K. J. (1969). Pharmacognosy of the leaf and root of *Barringtonia acutangula*, Gaertn. *Planta Medica* 17(4): 338-345.
20. Kincl, F. A. and Gedeon, J. (1957). About saponins and sapogenins of *Barringtonia* species. *Archiv der Pharmazie Berlin* 289(61): 140-143.
21. Nozoe, T. (1934). Polyterpenoids and their glycosides. I. Saponins from the seeds of *Barringtonia asiatica* Kurtz. *Journal of the Chemical Society of Japan* 55: 1106-1114.
22. Nozoe, T. (1934). Polyterpenoids and their glycosides. II. Constituents of the sugar part of $A_1$-barrinin. *Journal of the Chemical Society of Japan* 55: 1115-1123.
23. Nozoe, T. (1935). Polyterpenoids and their glycosides. III. $A_1$- and $A_2$-barrigenol. *Journal of the Chemical Society of Japan* 56: 689-703.
24. Cole, A. R. H., Downing, D. T., Watkins, J. C. and White, D. E. (1955). The constitution of $A_1$-Barrigenol. *Chemistry and Industry:* 254-255.
25. Anantaraman, R. and Pillai, K. S. M. (1956). Barringtogenol and barringtogenic acid, two new triterpenoid sapogenins. *Journal of the Chemical Society:* 4369-4373.
26. Barua, A. K., Maiti, P. C. and Chakraborti, S. K. (1961). Triterpenoids XI. New triterpenoid sapogenins from the fruits of *Barringtonia acutangula*. *Journal of Pharmaceutical Sciences* 50(11): 937-940.
27. Barua, A. K., Dutta, S. P. and Das, B. C. (1968). Triterpenoids—XXIX. The structure of Barringtogenol B—A new triterpenoid sapogenin from *Barringtonia acutangula* Gaertn. *Tetrahedron* 24: 1113-1117.
28. Barua, A. K., Dutta, S. P. and Pal, S. K. (1967). Triterpenoids—XXX.

The structure of Barringtogenol E—A new triterpenoid sapogenol from *Barringtonia acutangula* Gaertn. *Journal of the Indian Chemical Society* 44(11): 991-993.
29. Chakraborti, S. K. and Barua, A. K. (1962). Triterpenoid XIII. The constitution of Barringtogenol D. *Experientia* 18: 66-67.
30. Chakraborti, S. K. and Barua, A. K. (1963). Triterpenes— XVI. The constitution of Barringtogenol D—A new triterpenoid sapogenin from *Barringtonia acutangula* Gaertn. *Tetrahedron* 19: 1727-1732.

31. Barua, A. K. and Chakrabarti, P. (1965). Triterpenoids—XIX. The constitution of Barringtogenol C—A new triterpenoid sapogenin from *Barringtonia acutangula* Gaertn. *Tetrahedron* 21: 381-387.
32. Barua, A. K. and Chakrabarti, P. (1964). Triterpenoids XVIII. The constitution of Barringtogenol C. *Science and Culture* 30(7): 332-334.
33. Barua, A. K., Chakrabarti, S. K., Chakrabarti, P. and Maiti, P.C. (1963). Triterpenoids. Part XIV. Studies on the constitution of Barringtogenol C—A new triterpenoid sapogenin from *Barringtonia acutangula* Gaertn. *Journal of the Indian Chemical Society* 40(6): 483-485.
34. Chakrabarti, P., Pal, S. K. and Barua, A. K. (1967). Terpenoids. Some reactions of Barringtogenol C. *Proceedings of the Indian Science Congress* 54(3): 149.
35. Barua, A. K., Basak, A. and Chakravarti, S. (1976). Triterpenoids. XLIV. The revised structure of Barringtogenol B. *Journal of the Indian Chemical Society LIII:* 209-210.
36. Barua, A. K., Chakrabarti, P., Gupta, A. S. D., Pal, S. K., Basak, A., Banerjee, S. K. and Basu, K. (1976). The structure and stereochemistry of barrigenic acid, a new triterpene acid from *Barringtonia acutangula. Phytochemistry* 15: 1780-1781.
37. Barua, A. K., Pal, S. K. and Dutta, S. P. (1968). Triterpenoids—XXXI. Studies on a triterpene isolated from *Barringtonia acutangula* Gaertn. *Science and Culture* 34(6: 259-260.
38. Narayan, G. K. A. S. S., Row, L. R. and Sastry, C. S. (1976). Chemical examination of leaves of *Barringtonia acutangula* Gaertn. *Current Science* 45(14): 518-519.
39. Dhaveji, K., Narayan, G. K. A. S. S., Rao, D. S. and Row, L. R. (1984). 13C NMR spectra of Acutangulic and Tangulic acids from *Barringtonia acutangula* Gaertn. *Journal of the Indian Chemical Society* LXI: 1032-1033.
40. Anjaneyulu, A. S. R., Sastry, C. S. P., Narayan, G. K. A. S. S. and Row, L. R. (1978). New triterpenes from *Barringtonia acutangula* Gaertn. *Journal of the Indian Chemical Society* LV(11):1169-1174.
41. Pal, B. C., B, A. and Price, K. R. (1991). A triterpenoid glucoside from *Barringtonia acutangula. Phytochemistry* 30(12): 4177-4179.
42. Pal, B. C., Chaudhuri, T., Yoshikawa, K. and Arihara, S. (1994). Saponins from *Barringtonia acutangula. Phytochemistry* 35(5): 1315-1318.
43. Gupta, M.B., Bhalla, T. N., Gupta, G. P., Mitra, C. R. and Bhargava, K. P. (1969). Anti-inflammatory activity of natural products (I) Triterpenoids. *European Journal of Pharmacology* 6: 67-70.
44. Aquino, R., De Feo, V., De Simone, F., Pizza, C. and Cirino, G. (1991). Plant metabolites. New compounds from and anti-inflammatory activity of *Uncaria tomentosa. Journal of Natural Products* 54(2): 453-459.
45. Scalbert, A. (1991). Antimicrobial properties of tannins. *Phytochemistry* 30(12): 3875-3883.
46. Hiller, K. (1987). *New results on the structure and biological activity of triterpenoid saponins*, in Biologically active natural products. K. Hostettmann and P. J. Lea Editors. Clarendon Press. Oxford.
47. Hostettmann, K. and Marston, A. (1995). *Saponins. Chemistry and pharmacology of natural products.* ed. J. D. Phillipson, D. C. Ayres, and H. Baxter. Cambridge. Cambridge University Press.
48. Chen, S. and Snyder, J. K. (1993). *General strategy for the determination of saponins: Molluscicidal saponins from Allium vineale,* in Bioactive natural products. Detection, isolation and structural determination. S. M. Colegate and R. J. Molyneux Editors. CRC Press. Boca Raton.
49. Massiot, G. and Lavaud, C. (1995). Structural elucidation of saponins. *Studies in Natural Product Chemistry* 15: 187-224.
50. Maillard, M., Marston, A. and Hostettmann, K. (1993). *Search for molluscicidal and larvicidal agents from plants,* in Human medicinal agents from plants. A. D. Kinghom and M. F. Balandrin Editors. American Chemical Society. Washington DC.
51. van Middlesworth, F. and Cannell, R. J. P. (1998). *Dereplication and partial identification of natural products,* in Natural products isolation. R. J. P. Cannell Editors. Humana Press. Totowa.
52. Cordell, G. A., Lyon, R. L., Fong, H. S., Benoit, P. S. and Farnsworth, N. R. (1977). Biological and phytochemical investigations of *Dianthus barbatus* cv. "China Doll" (Caryophyllaceae). *Lloydia* 40(4): 361-363.
53. Huang, H., Huang, N. and Li, S. (1982). Analgesic effect of saponin from *Dolichos falcatus. Yaoxue Tongbao* 17(2): 122 (Ch).
54. Racz-Kotilla, E., Petre, M. and Racz, G. (1982). Antinociceptive effect of *Platycodon grandiflorum* extracts. Reviews of Medicine 28(2): 180-182.
55. Lei, W., Shi, Q. and Yu, S. (1984). Analgesic and CNS inhibitory effects of total saponins from the leaves of *Panax notoginseng. Zhongyao Tongbao* 9(3): 134-137.
56. Oshima, Y., Ohsawa, T., Oikawa, K., Konno, C. and Hikino, H. (1984). Structures of dianosides A and B, analgesic principles of *Dianthus superbus* var. *longicalycinus* herbs. *Planta Medica* 50(40-43).
57. Oshima, Y., Ohsawa, T. and Hikino, H. (1984). Structure of dianosides C, D, E and F, triterpenoid saponins of *Dianthus superbus* var. *longicalycinus* herb. *Planta Medica* 50: 43-47.
58. Oshima, Y., Ohsawa, T. and Hikino, H. (1984). Structures of dianosides G, H and I, triterpenoid saponins of *Dianthus superbus* var. *longicalycinus* herbs. *Planta Medica* 50: 254-258.
59. Gomes, A., Sharma, R. M. and Ghatak, B. J. R. (1987). Pharmacological investigation of a glycosidal fraction isolated from *Maesa chisia* D. Don var *augustifolia* Hook F and Th. Indian Journal of Experimental Biology 25: 826-831.
60. Dubuisson, D. and Dennis, S. G. (1977). The formalin test: A quantitative study of the analgesic effects of morphine, meperidine, and brain stem stimulation in rats and cats. *Pain* 4: 161-174.
61. Hunskaar, S. and Hole, K. (1987). The formalin test in mice:
dissociation between inflammatory and non-inflammatory pain. *Pain* 30: 103-114.
62. Hunskaar, S., Fasmer, O. B. and Hole, K. (1985). Formalin test in mice, a useful technique for evaluating mild analgesics. *Journal of Neuroscience Methods* 14: 69-76.Cohen, H. (1944).
63. Murray, C. W., Porreca, F. and Cowan, A. (1988). Methodological refinements to the mouse paw formalin test. An animal model of tonic pain. *Journal of Pharmacological Methods* 20:175-186.
64. Shibata, M., Ohkubo, T., Takahashi, H. and Inoki, R. (1989). Modified formalin test: characteristic biphasic pain response. *Pain* 38: 347-352.
65. Covino, B. G., Dubner, R., Kosterlitz, H. W., Liebsekind, J. C., Sternbach, R. A., Vyklicky, L., Yamamura, H. and Zimmermann, M. (1980). Ethical standards for the investigation of experimental pain in animals. *Pain* 9: 141-143.

66. Zimmermann, M. (1983). Ethical guidelines for investigations of experimental pain in conscious animals. *Pain* 16: 109-110.
67. Hostettmann, K. and Marston, A. (1995). *Saponins. Chemistry and pharmacology of natural products*. ed. J. D. Phillipson, D. C. Ayres, and H. Baxter. Cambridge. Cambridge University Press.
68. Cannell, R. J. P., ed. *Natural products isolation. Methods in biotechnology*, ed. J. M. Walker. Vol. 4. 1998, Humana Press: Totowa.
69. Chen, S. and Snyder, J. K. (1993). *General strategy for the determination of saponins: Molluscicidal saponins from Allium vineale*, in Bioactive natural products. Detection, isolation and structural determination. S. M. Colegate and R. J. Molyneux Editors. CRC Press. Boca Raton.

TABLE 1

Assay results for various solvent extractions.

| Extraction solvent | Pain inhibition (%) |
|---|---|
| CHCl$_3$: MeOH | 52 |
| MeOH | 46 |
| EtOAc | 57 |
| NH$_4$OH | 45 |
| DMSO | 64 |
| DMSO control | 57 |
| DMF | 47 |
| MeOH/TFA (0.5%) | 46 |
| CHCl$_3$ | 52 |

TABLE 2

TSK fractions - yields and activities.

| Fraction number | Weight assayed (mg/kg) | Pain Inhibition (%) | Inhibition (%/mg) |
|---|---|---|---|
| TSK-1 | 0.37 | 0 | 0 |
| TSK-2 | 15.82 | 74 | 4.7 |
| TSK-3 | 23.16 | 45 | 1.9 |
| TSK-4 | 0.70 | 32 | 44.9 |
| TSK-5 | 20.97 | 16 | 0.8 |

TABLE 3

C18 preliminary separation of TSK-4a.

| Fraction (% MeOH) | Weight assayed (mg/kg) | Pain Inhibition (%) | Inhibition (%/mg) |
|---|---|---|---|
| 0 | 1.3 | 80.40 | 61.85 |
| 35 | 0.27 | 80.85 | 303.93 |
| 70 | 0.21 | 97.23 | 469.72 |
| 100 | 0.24 | 91.81 | 377.81 |

TABLE 4

Activity of TSK-4a C18 fractions.

| Fraction (% MeOH) | Weight assayed (mg/kg) | Pain inhibition (%) | Inhibition (%/mg) |
|---|---|---|---|
| 0 | 1.28 | 4.9 | 4 |
| 10 | 0.25 | 52.5 | 210 |
| 20 | 0.38 | 91.6 | 241 |
| 30 | 0.098 | 71.6 | 730 |
| 40 | 0.21 | 58.9 | 281 |
| 50 | 0.12 | 70.1 | 584 |
| 60 | 0.09 | 67.6 | 751 |

TABLE 4-continued

Activity of TSK-4a C18 fractions.

| Fraction (% MeOH) | Weight assayed (mg/kg) | Pain inhibition (%) | Inhibition (%/mg) |
|---|---|---|---|
| 70 | 0.04 | 55.3 | 1381 |
| 80 | 0.047 | 53.1 | 1129 |
| 90 | 0.035 | 55.4 | 1582 |
| 100 | 0.047 | 46.3 | 985 |

TABLE 5

C18 preparative chromatography of H$_2$O extract.

| Fraction Identification | | Yields (%) | |
|---|---|---|---|
| Fraction (% MeOH) | Fraction Name | Laboratory prepared C18 | Davisil C18 |
| Insoluble | Insoluble | 32 | 42 |
| 0 | F0 | 40 | 32 |
| 10 | F10 | 1.3 | 2.4 |
| 20 | F20 | 1.8 | 2.9 |
| 30 | F30 | 1.5 | 1.2 |
| 40 | F40 | 0.5 | 0.4 |
| 50 | F50 | 0.4 | 0.5 |
| 60 | F60 | 0.7 | 1.3 |
| 70 | F70 | 1.1 | 2.1 |
| 80 | F80 | 0.8 | 2 |
| 90 | F90 | 0.2 | 0.2 |
| 100 | F100 | 0.01 | 0.01 |
| Total yield | | 80.31 | 87.01 |

Yields are with respect to the H$_2$O extract starting material.

TABLE 6

Separation of fraction F70.

| Starting material | Fractions obtained | Preliminary $^1$H-NMR |
|---|---|---|
| F70 | | Mixture |
| | F70.1-26.8% | " |
| | F70.2-18.3% | " |
| | F70.3-26.9% | " |
| | F70.4-17.4% | " |
| | F70.5-8.6% | " |
| Total Yield (%) | 98.0% | |

TABLE 7

Separation of fraction F70.2.

| Starting material | Fractions obtained | Preliminary $^1$H-NMR |
|---|---|---|
| F70.2 | | Mixture |
| | 70.2.1-10.0% | " |
| | 70.2.2-6.6% | " |
| | 70.2.3-8.4% | Pure |
| | 70.2.4-11.7% | " |
| | 70.2.5-17.1% | Mixture |
| | 70.2.6-11.7% | Pure |
| | 70.2.7-8.6% | " |
| | 70.2.8-23.7% | Mixture |
| Total Yield (%) | 97.8% | |

TABLE 8

Separation of fraction F70.2

| Starting material | Fractions obtained | Preliminary $^1$H-NMR |
|---|---|---|
| F70.2.2 | | Mixture |
| | 70.2.2.1-16.5% | " |
| | 70.2.2.2-10.2% | " |
| | 70.2.2.3-13.7% | PSC |
| | 70.2.2.4-9.2% | Mixture |
| | 70.2.2.5-30.5% | " |
| | 70.2.2.6-5.7% | PSC |
| | 70.2.2.7-6.6% | " |
| | 70.2.2.8-5.4% | Mixture |
| Total Yield (%) | 97.8% | |

(PSC = Predominantly single compound).

TABLE 9

Separation of fraction F70.2.5

| Starting material | Fractions obtained | Preliminary $^1$H-NMR |
|---|---|---|
| F70.2.2.5 | | Mixture |
| | 70.2.5.1-13.7% | " |
| | 70.2.5.2-10.0% | Pure |
| | 70.2.5.3-3.5% | PSC |
| | 70.2.5.4-9.6% | Mixture |
| | 70.2.5.5-4.4% | PSC |
| | 70.2.5.6-8.1% | " |
| | 70.2.5.7-5.0% | Mixture |
| | 70.2.5.8-7.0% | " |
| Total Yield (%) | 61.3% | |

(PSC = Predominantly single compound).

TABLE 10

Separation of fraction F70.3

| Starting material | Fractions obtained | Preliminary $^1$H-NMR |
|---|---|---|
| F70.3 | | Mixture |
| | 70.3.1-24.8% | " |
| | 70.3.2-5.5% | Pure |
| | 70.3.3-4.7% | Three compounds |
| | 70.3.4-9.3% | Mixture |
| | 70.3.5-9.7% | PSC |
| | 70.3.6-14.9% | Pure |
| | 70.3.7-6.3% | PSC |
| | 70.3.8-22.1% | Mixture |
| Total Yield (%) | 97.3% | |

(PSC = Predominantly single compound).

TABLE 11

Separation of fraction F70.3.4

| Starting material | Fractions obtained | Preliminary $^1$H-NMR |
|---|---|---|
| F70.3.4 | | |
| | 70.3.4.1-33.6% | M |
| | 70.3.4.2-13.9% | PSC |
| | 70.3.4.3-8.9% | M |
| | 70.3.4.4-9.1% | PSC |
| | 70.3.4.5-3.6% | M |
| Total Yield (%) | 69.1% | |

(PSC = Predominantly single compound).

TABLE 12

Separation of fraction F70.4

| Starting material | Fractions obtained | Preliminary $^1$H-NMR |
|---|---|---|
| F70.4 | | Mixture |
| | 70.4.1-7.8% | " |
| | 70.4.2-62.5% | PSC |
| | 70.4.3-16.5% | " |
| Total Yield (%) | 86.8% | |

(PSC = Predominantly single compound).

TABLE 12A

Separation of fraction F70.4.2

| Starting material | Fractions obtained | Preliminary $^1$H-NMR |
|---|---|---|
| F70.4.2 | | |
| | 70.4.2.1-34.1% | Mixture |
| | 70.4.2.2-11.3% | PSC |
| | 70.4.2.3-34.3% | " |
| | 70.4.2.4-9.4% | Two compounds |
| Total Yield (%) | 89.1% | |

(PSC = Predominantly single compound).

TABLE 13

Separation of fraction F70.4.3

| Starting material | Fractions obtained | Preliminary $^1$H-NMR |
|---|---|---|
| F70.4.3 | | Mixture |
| | 70.4.3.1-31.6% | " |
| | 70.4.3.2-6.1% | PSC |
| | 70.4.3.3-6.6% | Mixture |
| | 70.4.3.4-22.3% | " |
| | 70.4.3.5-18.3% | " |
| Total Yield (%) | 84.9% | |

(PSC = Predominantly single compound).

TABLE 14

Separation of fraction F70.4.3

| Starting material | Fractions obtained | Preliminary $^1$H-NMR |
|---|---|---|
| F80 | | Mixture |
| | 80.1-27.7% | " |
| | 80.2-1.3% | " |
| | 80.3-1.3% | " |
| | 80.4-21.9% | " |
| | 80.5-14.3% | PSC |
| | 80.6-25.8% | Mixture |
| Total Yield (%) | 92.3% | |

(PSC = Predominantly single compound).

TABLE 15

Separation of fraction F80.4

| Starting material | Fractions obtained | Preliminary $^1$H-NMR |
|---|---|---|
| F80.4 | | Mixture |
| | 80.4.1-25.9% | " |
| | 80.4.2-7.9% | " |
| | 80.4.3-13.4% | " |
| | 80.4.4-27.5% | " |
| | 80.4.5-6.6% | PSC |
| | 80.4.6-16.0% | " |
| Total Yield (%) | 97.3% | |

(PSC = Predominantly single compound).

TABLE 16

Separation of fraction F80.6

| Starting material | Fractions obtained | Preliminary $^1$H-NMR |
|---|---|---|
| F80.6 | | Mixture |
| | 80.6.1-19.3% | " |
| | 80.6.2-11.7% | PSC |
| | 80.6.3-28.4% | " |
| | 80.6.4-13.4% | " |
| | 80.6.5-9.7% | Mixture |
| | 80.6.6-4.7% | PSC |
| | 80.6.7-2.6% | " |
| Total Yield (%) | 89.8% | |

(PSC = Predominantly single compound).

TABLE 17

Compounds isolated in the current project.

| Compound | Weight isolated (mg) | Compound | Weight isolated (mg) |
|---|---|---|---|
| F70.2.3.2 | 8.4 | F70.4.2.4.2 | 4.9 |
| F70.2.5.2 | 5.4 | F70.4.3.2.2 | 3.0 |
| F70.2.6.2 | 19.2 | F70.4.3.4.2 | 6.4 |
| F70.3.2 | 26.3 | F70.4.3.5.2 | 3.1 |
| F70.3.3.2.2 | 6.2 | F80.4.5.2 | 3.4 |
| F70.3.4.2 | 12.2 | F80.5.2 | 20.1 |
| F70.3.4.5 | 2.7 | F80.6.2 | 7.4 |
| F70.3.5 | 21.0 | F80.6.3 | 25.8 |
| F70.3.6 | 152.6 | F80.6.4 | 12.1 |
| F70.3.7 | 10.3 | F80.6.6 | 4.3 |
| F70.4.2.3 | 24.1 | F80.6.7 | 3.9 |

TABLE 18

Fractions collected in the current work with some information about the compounds in those fractions.

| Number | Weight (mg) | Major ESMS peaks +ve ion | Major ESMS peaks −ve ion | Comments |
|---|---|---|---|---|
| F70.2.1.2 | 6.8 | | 1504, 1156, 1042, 927, 809, 363 | M |
| F70.2.1.3 | 1.1 | | 1471, 1396, 908, 793, 363 | US |
| F70.2.1.4 | 1.0 | | 1286, 1076, 907, 794 | US |
| F70.2.1.5 | 4.8 | | 961, 831, 697, 616, 539, 403 | M |
| F70.2.2.2 | 3.2 | | 1601, 1422, 1216, 909, 776, 652 | M, B, T |
| F70.2.2.3 | 4.3 | | 1443, 1328, 1127, 1056, 403, 363, 249 | PSC, 2B |
| F70.2.2.4 | 2.9 | | 1140, 953, 777, 538, 403 | M |
| F70.2.2.5 | 9.6 | | | M |
| F70.2.2.6 | 1.8 | | | PSC, 2B |
| F70.2.2.7 | 2.1 | | | PSC, 1B |
| F70.2.2.8 | 1.7 | | | 2B |
| F70.2.3.3 | 2.8 | | 1337, 1197, 1083, 1046, 931, 517 | M, B's |
| F70.2.3.4 | 2.8 | | 1334, 1198, 1083, 363, 249 | US |
| F70.2.4.2 | 10.5 | 1230, 1108, 361 | 1198, 1084, 516, 363 | PSC, T |
| F70.2.4.3 | 13.3 | | 1197, 1036, 807, 632, 517 | M, PS |
| F70.2.5.3 | 7.7 | | 1060, 1035, 517 | 2 compounds |
| F70.2.5.4 | 12.3 | | | M |
| F70.2.5.5 | 2.4 | | | PSB, 2B |
| F70.2.5.6 | 4.4 | | | PSC, 1B |
| F70.2.5.7 | 2.7 | | | M |
| F70.2.5.8 | 3.8 | | | M, 3B |

TABLE 18-continued

Fractions collected in the current work with some information about the compounds in those fractions.

| Number | Weight (mg) | Major ESMS peaks +ve ion | Major ESMS peaks −ve ion | Comments |
|---|---|---|---|---|
| F70.2.6.3 | 5.3 | | | US, PS |
| F70.2.7.2 | 5.3 | 1346, 1324, 1234 | 1322, 1299, 1210 | M, B's |
| F70.3.4.3 | 7.8 | 1444, 1421, 733, 361 | 1398 | PSC, 2T |
| F70.3.4.4 | 8.0 | | | M, 2B, T |
| F70.3.5.3 | 16.3 | | 1420, 403 | US, PS |
| F70.4.2.2 | 28.1 | 1170, 1147, 361 | 1146, 1124 | PSC, 2T |
| F70.4.2.4 | 23.2 | | | M, B's, T's |
| F70.4.3.3 | 8.3 | | | M, 1B, 1T |
| F70.4.4 | 160.0 | | | M, B's, T's |
| F80.2.2 | 15.5 | | 1169, 1146, 1124, 462 | PSC, 2B |
| F80.2.3 | 7.9 | | | M, 1B |
| F80.3.2 | 13.6 | | | M, B's |
| F80.3.3 | 6.4 | | | US |
| F80.4.2.2 | 2.4 | | | PSC, 1B |
| F80.4.3 | 23.4 | | | M, B's, T's |
| F80.4.4 | 58.1 | | | M, B's, T's |
| F80.4.6 | 13.9 | | | M, B's |
| F80.6.5 | 12.0 | | 1442, 1252, 1168, 363 | M, B's, T's |
| F80.6.8 | 8.4 | | 1168, 1145 | M, B's |
| F80.7 | 153.0 | | | M, B's |

(M = Mixture, B = Benzoate, T = Tiglate, PSC = Predominantly Single Compound, US = Insufficient material for clear spectrum, PS = Plasticiser present).

TABLE 19

Side effects of F70.3.2

| Dose (mg/kg) | Side effect | Onset | Duration | Intensity 0 = none; 1 = mild; 2 = moderate; 3 = severe; 4 = extreme | Temporal Intensity 0 = Absent 1 = Intermittent 2 = Continuous | No of rats observed with side-effect |
|---|---|---|---|---|---|---|
| 0.005 | Apnoea | 3 h | 30 sec | 1 | I | 1/3 |
| 0.02 | Apnoea | 30 min | 15 min | 1 | I | 1/3 |
| | Staring | 30 min | 15 min | 1 | I | 1/3 |

TABLE 20

Side effects of F70.3.6

| Dose (mg/kg) | Side effect | Onset | Duration | Intensity 0 = none 1 = mild 2 = moderate 3 = severe 4 = extreme | Temporal Intensity 0 = Absent 1 = Intermittent 2 = Continuous | No of rats observed with side-effect |
|---|---|---|---|---|---|---|
| 0.005 | Body shaking | 15 min | 5 min | 1 | I | 1/3 |
| 0.01 | Body shaking | 30 min | 5 min | 1 | I | 1/3 |
| 0.02 | Staring | 45 min | 15 min | 1 | I | 1/3 |
| 0.05 | Staring | 30 min | 15 min | 1 | I | 1/1 |
| | Apnoea | 5 min | 30 min | 1 | C | 1/1 |

The claims defining the invention are as follows:

1. A compound of the formula (I):

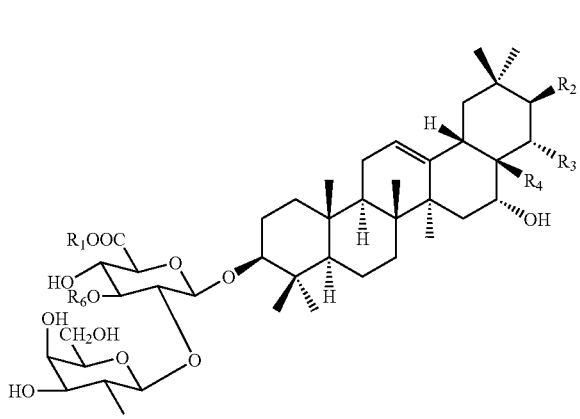

wherein:

$R_2$ is selected from hydrogen, hydroxyl, O-alkyl, O-alkenyl, O-benzoyl, O-alkanoyl, O-alkenoyl, O-aryl, O-heterocyclic, O-heteroaryl or

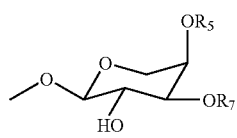

wherein $R_5$ and $R_7$ are independently be selected from hydrogen, alkanoyl, alkenoyl, benzoyl or benzoyl alkyl substituted alkanoyl;

$R_3$ is selected from hydroxyl, O-alkanoyl, O-alkenoyl, O-benzoyl, O-alkyl, O-alkenyl, O-aryl, O-heterocyclic or O-heteroaryl;

$R_4$ is selected from —$CH_2OH$, COOH, $CH_2OCOCH_3$, COO alkyl, COO aryl, $CH_2COO$ alkyl, COO-heterocyclic, COO-heteroaryl, $CH_2$—O aryl, $CH_2O$ heterocyclic or $CH_2O$ heteroaryl;

$R_6$ is selected from hydrogen or

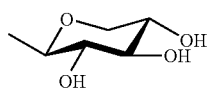

$R_1$ is selected from hydrogen or alkyl; or pharmaceutically acceptable salts thereof, with the provisos that when:

$R_2$ is OH, $R_3$ is OH, $R_4$ is $CH_2OH$, and $R_6$ is xylopyranosyl, $R_1$ is not H;

$R_4$ is $CH_2OH$ and $R_3$ is O-alkanoyl $R_2$ is not O-acetyl;

$R_4$ is $CH_2OH$ and $R_2$ is O-alkenoyl $R_3$ is not hydroxyl; and $R_4$ is $CH_2OH$ and $R_3$ is hydroxyl then $R_2$ is not hydroxyl.

2. A compound as claimed in claim 1 wherein $R_2$ is hydrogen, O-benzoyl, O-tigloyl or

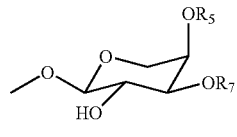

wherein $R_5$ and $R_7$ are selected from hydrogen, tigloyl, benzoyl or benzoyl alkyl substituted alkanoyl.

3. A compound as claimed in claim 1 wherein $R_3$ is selected from hydroxyl, O-acetyl, O-benzoyl, O-isobutyryl or O-tigloyl.

4. A compound as claimed in claim 1 wherein $R_4$ is selected from —$CH_2OH$, and $CH_2OCOCH_3$.

5. A compound as claimed in claim 1 wherein $R_2$ is arabino pyranosyl, 3-(3-benzoyl-2-methylbutanoyl)-4-benzoyl-α-L-arabinopyranosyl, O-benzoyl, O-dibenzoyl, O-tigloyl, 3,4 dibenzoyl α-L-arabinopyranosyl, 3-(3-benzoyl-2 methylbutyryl-4-tigloyl-α-L-arabinopyranosyl, 3-tigloyl-4-(3-benzoyl-2 methylbutyryl)-α-L-arabinopyranosyl, 3-(3-benzoyl-2 methyl butanoyl-4-benzoyl-α-L-arabinopyranosyl or 3-(3-benzoyl-2 methylbutyryl)-4-benzoyl-α-L-arabinopyranosyl.

6. A compound as claimed in claim 1 comprising 3-O-β-D-xylopyranosyl(1→3)-[β-D-galactopyranosyl(1→2)]-β-D-glucuronopyranosyl-21-O-[3-(3-benzoyl-2methylbutanoyl)-4-benzoyl-α-L-arabinopyranosyl]-22-O-acetyl barringtogenol C.

7. A compound as claimed in claim 1 comprising 3-O-β-D-xylopyranosyl(1→3)-[β-D-galactopyranosyl(1→2)] β-D-glucuronopyranosyl-21-O-benzoyl-barringtogenol C.

8. A compound as claimed in claim 1 comprising 3-O-β-D-galactopyranosyl(1→3)-[β-D-galactopyranosyl(1→2)]-β-D-glucuronopyranosyl-21-O-benzoyl-28-O-acetyl barringtogenol C.

9. A compound as claimed in claim 1 comprising 3-O-β-D-xylopyranosyl(1→3)-[β-D-galactopyranosyl(1→2)]-β-D-glucuronopyranosyl-21-O-benzoyl-22-O-isobutyryl barringtogenol C.

10. A compound as claimed in claim 1 comprising 3-O-β-D-xylopyranosyl(1→3)-[β-D-galactopyranosyl(1→2)]-β-D-methylglucuronopyranosyl-21,22-O-dibenzoyl barringtogenol C.

11. A compound as claimed in claim 1 comprising 3-O-β-D-xylopyranosyl(1→3)-[β-D-galactopyranosyl(1→2)]-β-D-glucuronopyranosyl-21,22-O-dibenzoyl barringtogenol C.

12. A compound as claimed in claim 1 comprising 3-O-β-D-xylopyranosyl(1→3)-[β-D-galactopyranosyl(1→2)]-β-D-methylglucuronopyranosyl-21-O-benzoyl-22-O-tigloyl barringtogenol C.

13. A compound as claimed in claim 1 comprising comprising 3-O-β-D-xylopyranosyl (1→3)-[β-D-galactopyranosyl(1→2)]-β-D-glucuronopyranosyl-21-O-benzoyl-22-O-tigloyl barringtogenol C.

14. A compound as claimed in claim 1 comprising 3-O-β-D-xylopyranosyl(1→3)-[β-D-galactopyranosyl(1→2)]-β-D-methylglucuronopyranosyl-21-22-O-tigloyl barringtogenol C.

15. A compound as claimed in claim 1 comprising 3-O-β-D-xylopyranosyl(1→3)-[β-D-galactopyranosyl(1→2)]-β-D-glucuronopyranosyl-21-22-O-tigloyl barringtogenol C.

16. A compound as claimed in claim 1 comprising 3-O-β-D-xylopyranosyl(1→3)-[β-D-galactopyranosy (1→2)]-β-D-glucuronopyranosyl-22-O-benzoyl barringtogenol C.

17. A compound as claimed in claim 1 comprising 3-O-β-D-xylopyranosyl(1→3)-[β-D-galactopyranosyl(1→2)]-β-D-glucuronopyranosyl-21-O-[3,4-dibenzoyl-α-L-arabinopyranosyl]-22-O-acetyl barringtogenol C.

18. A compound as claimed in claim 1 comprising 3-O-β-D-xylopyranosyl(1→3)-[β-D-galactopyranosyl(1→2)]-β-D-glucuronopyranosyl-21-O-[3,4-dibenzoyl-α-L-arabinopyranosyl]-28-O-acetyl barringtogenol C.

19. A compound as claimed in claim 1 comprising 3-O-β-D-xylopyranosyl(1→3)-[β-D-galactopyranosyl(1→2)]-β-D-glucuronopyranosyl-21-O-[3-(3-benzoyl-2-methylbutyryl)-4-tigloyl-α-L-arabinopyranosyl]-22-O-acetyl barringtogenol C.

20. A compound as claimed in claim 1 comprising 3-O-β-D-xylopyranosyl(1→3)-[β-D-galactopyranosyl(1→2)]-β-D-glucuronopyranosyl-21-O-[3-tigloyl-4-(3-benzoyl-2-methylbutyryl)-α-L-arabinopyranosyl]-22-O-acetyl barringtogenol C.

21. A compound as claimed in claim 1 comprising 3-O-β-D-galactopyranosyl(1→2)-β-D-glucuronopyranosyl-21-O-[3-(3-benzoyl-2-methylbutyryl)-4-benzoyl-α-L-arabinopyranosyl]-22-O-acetyl barringtogenol C.

22. A compound as claimed in claim 1 comprising 3-O-β-D-xylopyranosyl(1→3)-[β-D-galactopyranosyl(1→2)]-β-D-glucuronopyranosyl-21-O-[3-(3-benzoyl-2-methylbutyryl)-4-benzoyl-α-L-arabinopyranosyl]-28-O-acetyl barringtogenol C.

23. A pharmaceutical composition for treatment and/or control of pain comprising a therapeutically effective amount of a compound of claim 1 and a pharmaceutical carrier.

24. A pharmaceutical composition as claimed in claim 23 wherein the carrier is a pharmaceutically acceptable excipient.

25. A method of treating and/or controlling nociceptive pain which includes the step of administering to a subject in need of such treatment at least one compound as claimed in claim 1.

* * * * *

UNITED STATES PATENT AND TRADEMARK OFFICE
CERTIFICATE OF CORRECTION

PATENT NO.       : 7,618,946 B2
APPLICATION NO.  : 10/580805
DATED            : November 17, 2009
INVENTOR(S)      : Quinn et al.

It is certified that error appears in the above-identified patent and that said Letters Patent is hereby corrected as shown below:

In col. 41, line 5, please replace the formula (1) structure with the following:

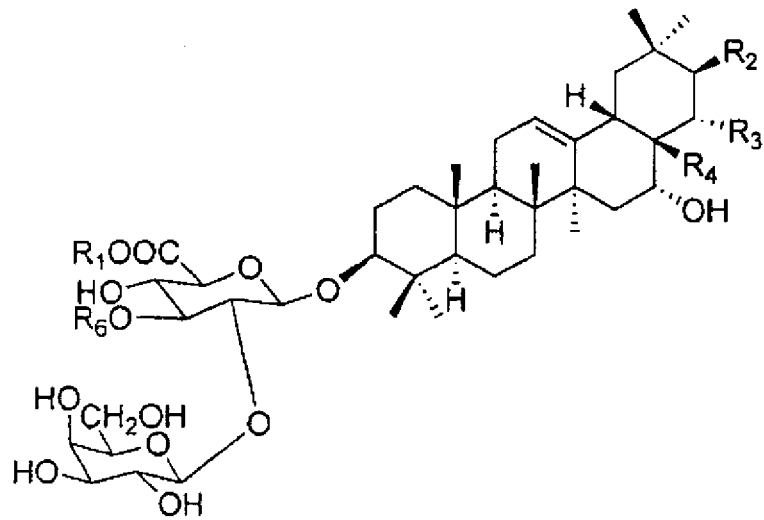

Signed and Sealed this

Second Day of February, 2010

David J. Kappos
*Director of the United States Patent and Trademark Office*